United States Patent
Dunn et al.

(10) Patent No.: US 7,241,794 B2
(45) Date of Patent: Jul. 10, 2007

(54) NONNUCLEOSIDE REVERSE TRANSCRIPTASE INHIBITORS

(75) Inventors: James Patrick Dunn, Los Altos, CA (US); Joan Heather Hogg, Foster City, CA (US); Taraneh Mirzadegan, Los Altos, CA (US); Steven Swallow, Los Altos, CA (US)

(73) Assignee: RochePalo Alto LLC, Palo Alto, CA (US)

(*) Notice: Subject to any disclaimer, the term of this patent is extended or adjusted under 35 U.S.C. 154(b) by 473 days.

(21) Appl. No.: 10/781,373

(22) Filed: Feb. 18, 2004

(65) Prior Publication Data
US 2004/0192666 A1    Sep. 30, 2004

Related U.S. Application Data

(60) Provisional application No. 60/447,974, filed on Feb. 18, 2003.

(51) Int. Cl.
*A61K 31/415* (2006.01)
*C07D 231/18* (2006.01)

(52) U.S. Cl. .................. 514/407; 548/370.1
(58) Field of Classification Search .............. 514/407; 548/370.1
See application file for complete search history.

(56) References Cited

U.S. PATENT DOCUMENTS

| | | | |
|---|---|---|---|
| 6,538,015 B1 * | 3/2003 | Dymock et al. | 514/407 |
| 7,109,228 B2 * | 9/2006 | Jones et al. | 514/407 |
| 2002/0032184 A1 | 3/2002 | Corbau et al. | |
| 2002/0107272 A1 | 8/2002 | Dymock et al. | |
| 2003/0008841 A1 | 1/2003 | Devos et al. | |
| 2003/0018197 A1 | 1/2003 | Dymock et al. | |

FOREIGN PATENT DOCUMENTS

| | | |
|---|---|---|
| EP | 0 786 455 A1 | 7/1997 |
| WO | WO 02/04424 A1 | 1/2002 |
| WO | WO 02/30907 A1 | 4/2002 |
| WO | WO 02/085860 A1 | 10/2002 |
| WO | WO 02/100853 A1 | 12/2002 |

* cited by examiner

*Primary Examiner*—Kamal A. Saeed
(74) *Attorney, Agent, or Firm*—Brian L. Buckwalter

(57) ABSTRACT

This invention relates to novel pyrazole derivatives of formula I wherein R1 to R4 are as defined in the summary and pharmaceutically acceptable salts and solvates thereof, methods to inhibit or modulate Human Immunodeficiency Virus (HIV) reverse transcriptase with compounds of formula I and pharmaceutical compositions containing of formula I admixed with at least one solvent, carrier or excipient. The compounds are useful for treating disorders in which HIV and genetically related viruses are implicated

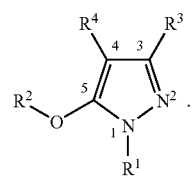

I

5 Claims, No Drawings

NONNUCLEOSIDE REVERSE TRANSCRIPTASE INHIBITORS

CROSS REFERENCE TO PRIOR APPLICATIONS

This application claims benefit under Title 35 U.S.C. 119(e) of U.S. Provisional Application No. 60/447,974 filed Feb. 18, 2003 which is hereby incorporated by reference in its entirety.

FIELD OF THE INVENTION

The invention relates to the field of antiviral therapy and, in particular, to non-nucleoside reverse transcriptase inhibitors for treating Human Immunodeficiency Virus (HIV) mediated diseases. The invention provides novel pyrazole compounds, pharmaceutical compositions comprising these compounds, methods for treatment or prophylaxis of HCV mediated diseases employing said compounds in monotherapy or in combination therapy.

BACKGROUND OF THE INVENTION

The human immunodeficiency virus (HIV) is the causative agent of acquired immunodeficiency syndrome (AIDS), a disease characterized by the destruction of the immune system, particularly of the CD4$^+$ T-cell, with attendant susceptibility to opportunistic infections. HIV infection is also associated with a precursor AIDs-related complex (ARC), a syndrome characterized by symptoms such as persistent generalized lymphadenopathy, fever and weight loss.

In common with other retroviruses, the HIV genome encodes protein precursors known as gag and gag-pol which are processed by the viral protease to afford the protease, reverse transcriptase (RT), endonuclease/integrase and mature structural proteins of the virus core. Interruption of this processing prevents the production of normally infectious virus. Considerable efforts have been directed towards the control of HIV by inhibition of virally encoded enzymes.

Currently available chemotherapy targets two crucial viral enzymes: HIV protease and HIV reverse transcriptase. (J. S. G. *Montaner et al. Antiretroviral therapy: "The State of the Art", Biomed. & Pharmacother.* 1999 53:63-72; R. W. Shafer and D. A. Vuitton, *Highly active antiretroviral therapy(HAART) for the treatment of infection with human immunodeficiency virus type 1, Biomed & Pharmacother.* 1999 53:73-86; E. De Clercq, *New Developments in Anti-HIV Chemotherap. Curr. Med. Chem.* 2001 8:1543-1572). Two general classes of reverse transcriptase inhibitors (RTIs) have been identified: nucleoside reverse transcriptase inhibitors (NRTIs) and non-nucleoside reverse transcriptase inhibitors (NNRTIs). NRTIs typically are 2',3'-dideoxynucleoside (ddN) analogs that must be phosphorylated prior to interacting with viral RT. The corresponding triphosphates function as competitive inhibitors or alternative substrates for viral RT. After incorporation into nucleic acids the nucleoside analogs terminate the chain elongation process. HIV reverse transcriptase has DNA editing capabilities which enable resistant strains to overcome the blockade by cleaving the nucleoside analog and continuing the elongation. Currently clinically used NRTIs include zidovudine (AZT), didanosine (ddI), zalcitabine (ddC), stavudine (d4T), lamivudine (3TC) and tenofovir (PMPA).

NNRTIs were first discovered in 1989. NNRTI are allosteric inhibitors which bind reversibly at a nonsubstrate binding site on the HIV reverse transcriptase thereby altering the shape of the active site or blocking polymerase activity. (R. W. Buckheit, Jr., *Non-nucleoside reverse transcriptase inhibitors: perspectives for novel therapeutic compounds* and *strategies for treatment of HIV infection, Expert Opin. Investig. Drugs* 2001 10(8)1423-1442; E. De Clercq *The role of non-nucleoside reverse transcriptase inhibitors (NNRTIs) in the therapy of HIV-1 infection, Antiviral Res.* 1998 38:153-179; G. Moyle, *The Emerging Roles of Non-Nucleoside Reverse Transcriptase Inhibitors in Antiviral Therapy, Drugs* 2001 61(1):19-26) Although over thirty structural classes of NNRTIs have been identified in the laboratory, only three compounds have been approved for HIV therapy: efavirenz, nevirapine and delavirdine. Although initially viewed as a promising class of compounds, in vitro and in vivo studies quickly revealed the NNRTIs presented a low barrier to the emergence of drug resistant HIV strains when used in monotherapy as well as having and class-specific toxicity. Drug resistance frequently develops with only a single point mutation in the RT.

While combination therapy with NRTIs, PIs and NNRTIs has, in many cases, dramatically lowered viral loads and slowed disease progression, significant therapeutic problems remain. The cocktails are not effective in all patients, potentially severe adverse reactions often occur and the rapidly reproducing HIV virus has proven adroit at creating mutant drug-resistant variants of wild-type protease and reverse transcriptase.

There remains a need for safer drugs with activity against wild type and commonly occurring resistant strains of HIV.

WO 02/100852 (B. W. Dymock et al.) discloses novel pyrazole derivatives, processes for preparing the novel pyrazoles, pharmaceutical compositions containing the pyrazoles and the use of pyrazoles as inhibitors of human immunodeficiency virus reverse transcriptase enzyme which is involved in viral replication. WO 02/30907 (B. W. Dymock et al.) also teaches novel pyrazoles useful for inhibiting HIV reverse transcriptase. These patents are hereby incorporated by reference in their entirety.

U.S. Pat. No. 6,005,109 (W. S. Faraci) EP 0 691 128 (G. M. Bright et al.) and EP 0 959 074 (G. M. Bright et al.) disclose pyrazole derivatives which have corticotropin releasing factor antagonist activity.

EP 1 072 597 (Banks, B. J. et al.) disclose pyrazole derivatives with endothelin antagonist activity. WO 97/04773 (J. I. Luengo et al.) discloses phenyl pyrazoles as endothelin receptor antagonists for treating cardiovascular or renal disease.

WO 02/04424 (R. G. Corbau et al.) discloses the use of pyrazole derivatives in the manufacture of reverse transcriptase inhibitor or modulator, to novel pyrazole derivatives and to processes for the preparation pyrazole derivatives and for compositions containing novel pyrazole derivatives. WO 02/085860 (L. H. Jones, et al) disclose pyrazole compounds, processes for the preparation of the pyrazole compounds and uses for the compounds to inhibit or modulate viral enzyme reverse transcriptase. The use of the pyrazoles for the treatment diseases caused Human Immuno-deficiency Virus (HIV) also is taught.

WO 00/66562 (V. B. Lohray et al.) disclose phenylsulfinyl-, phenylsulfonyl- and phenylthio-substituted pyrazole compounds which inhibit r-hu COX-2 useful for inhibiting prostaglandin biosynthesis, and treating pain fever and inflammation. WO 01/16138 (T. Kolasta and M. V. Patel) and WO 01/64669 (H. Cheng et al.) also disclose sulfonylphenyl substituted pyrazole compounds which inhibit COX-2.

Hydroxypyrazole derivatives have been disclosed to have agrochemical pesticide activity. WO 99/33813 (P. Desbordes et al.) discloses fungicidal aryloxypyrazoles.

SUMMARY OF THE INVENTION

The present invention relates to a compounds according to formula I, methods for treating diseases mediated by human immunodeficiency virus by administration of a compound according to formula I and pharmaceutical compositions for treating diseases mediated by human immunodeficiency virus containing a compound according to formula I,

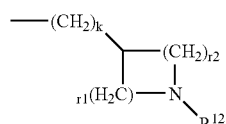
(IIa)

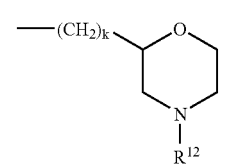
(IIb)

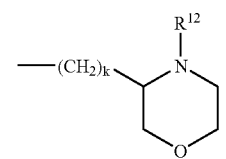
(IIc)

wherein
R$^1$ is selected from the group consisting of C$_{1-6}$alkyl, C$_{1-6}$haloalkyl, C$_{3-6}$alkenyl, C$_{3-6}$alkynyl, C$_{3-7}$cycloalkyl, C$_{1-3}$alkoxy-C$_{1-3}$ alkyl, phenyl and benzyl, wherein,
said phenyl and said benzyl optionally substituted with one to three substituents independently selected from the group consisting of C$_{1-6}$alkyl, C$_{1-6}$haloalkyl, C$_{1-6}$alkoxy, C$_{1-6}$haloalkoxy, C$_{1-6}$alkylthio, nitro, halogen and cyano;
R$^2$ is phenyl or pyridyl optionally substituted with one to three groups independently selected from the group consisting of halogen, cyano, C$_{1-6}$alkyl, C$_{1-6}$alkoxy, C$_{1-6}$alkoxycarbonyl, and CONR$^6$R$^7$;
R$^3$ is substituted C$_{1-6}$alkyl, substituted C$_{1-3}$alkoxy-C$_{1-3}$ alkyl, substituted C$_{3-6}$alkenyl, C$_{3-7}$ cycloalkyl, optionally substituted C$_{1-6}$alkoxy, —(CH$_2$)$_n$R$^5$, —CH(OH)R$^5$, —(CH$_2$)$_o$—O—(CH$_2$)$_p$R$^5$, NR$^6$R$^7$, C(=Y)Z, —X(C=Y)Z or IIa-c;

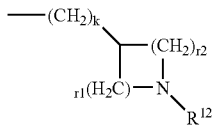
(IIa)

-continued

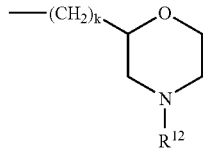
(IIb)

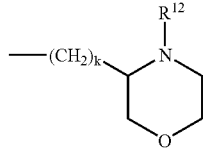
(IIc)

wherein,
said alkyl, said C$_{1-3}$alkoxy-C$_{1-3}$alkyl and said alkenyl are substituted by —OH, —NR$^6$R$^7$, —C(=Y)Z, —X(C=Y)Z, CN, —S(O)$_q$—C$_{1-6}$alkyl; —SO$_2$NR$^6$R$^7$, —SO$_2$NHNH$_2$, or —NR$^6$SO$_2$-C$_{1-6}$alkyl;
said alkoxy is optionally substituted by —OH, —NR$^6$R$^7$, —C(=Y)Z, —X(C=Y)Z, —S(O)$_q$—C$_{1-6}$alkyl; —SO$_2$NR$^6$R$^7$ or —SO$_2$NHNH$_2$;
R$^{12}$ is hydrogen, C$_{1-6}$alkyl or —C(=Y)Z;
R$^5$ is a phenyl or a heteroaryl ring according to formula IIIa-IIIh;

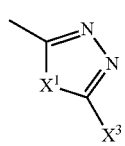
(IIIa)

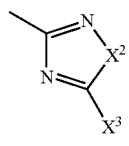
(IIIb)

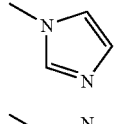
(IIIc)

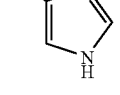
(IIId)

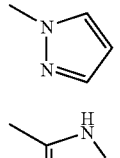
(IIIe)

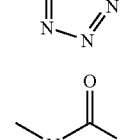
(IIIf)

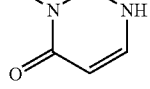
(IIIg)

-continued

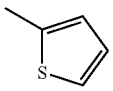

(IIIh)

wherein
- $X^1$ is selected from the group consisting of $-R^{10}C=CR^{10a}-$, $-O-$, $-S-$, $-NR^6-$ and $-CHR^6-$;
- $X^2$ is selected from the group consisting of $-R^{10}C=CR^{10a}-$, $-O-$, $-S-$, and $-CHR^6-$;
- $X^3$ is selected from the group consisting of hydrogen, hydroxyl and thiol; said phenyl and said heteroaryl ring optionally substituted with halo, $OR^6$, $NR^6R^7$, $C(=O)Z$, $-X(C=O)Z$
- $R^{10}$ and $R^{10a}$ are independently are selected from the group consisting of hydrogen or $C_{1-6}$alkyl optionally substituted with one or two substituents independently selected from the group consisting of hydroxy, $C_{1-6}$alkoxy, thiol, $C_{1-6}$alkylthio, $C_{1-6}$alkylsulfinyl, $C_{1-6}$ alkylsulfonyl, halogen, amino, $C_{1-6}$ alkylamino, $C_{1-3}$ dialkylamino, amino-$C_{1-3}$ alkyl, $C_{1-3}$ alkylamino-$C_{1-3}$ alkyl and $C_{1-3}$ dialkylamino-$C_{1-3}$ alkyl;
- $R^4$ is $C_{1-6}$ alkyl, $C_{2-6}$ alkenyl, $C_{2-6}$ alkynyl, $C_{3-7}$ cycloalkyl, $C_{1-3}$ alkoxy-$C_{1-3}$ alkyl, $(CH_2)_nR^{11}$ or $-(CH_2)_o-O-(CH_2)_pR^{11}$; wherein,
  - said alkyl, said alkenyl, said alkynyl and said cycloalkyl are optionally substituted by $-OH$, $-OR^6$, $-NR^8R^9$, $-C(=Y)Z$, $-X(C=Y)Z$, $-S(O)_q-C_{1-6}$alkyl, $-SO_2NR^6R^7$ or $-SO_2NH$ $NH_2$;
- $R^{11}$ is a phenyl or a heteroaryl ring selected from the group consisting of pyridinyl, pyrimidinyl pyrazinyl, pyrrole, imidazole, pyrazole and thiophene, said heteroaryl ring and said phenyl optionally substituted with one to three groups independently selected from the group consisting of halogen, cyano, $C_{1-3}$ alkyl, $C_{1-3}$ haloalkyl and $C_{1-3}$ alkoxy; or $R^{11}$ is $N[(CH_2)_2]_2W$ wherein W is selected from the group consisting of $NR^6$, $(CH_2)_s$, $-N(C=O)Z$, $CHOR^6$, $CHR^6$ $CHNHC(=O)Z$ and $CHNR^6R^7$;
- n, o and p are as defined below and s is 0 or 1;
- $R^6$, $R^7$, $R^8$ and $R^9$ (i) taken independently are selected from the group consisting of hydrogen, $C_{1-6}$ alkyl, $C_{1-6}$ hydroxyalkyl, $C_{1-3}$ alkoxy-$C_{1-3}$ alkyl $C_{1-3}$ alkylamino-$C_{1-3}$ alkyl and $C_{1-3}$ dialkyl or (ii) when both $R^6$ and $R^7$ are attached to the same nitrogen atom they may be taken together, along with the nitrogen, to form a pyrrolidine, piperidine, piperazine or morpholine;
- X, and Y are independently O or $NR^6$;
- Z is hydrogen, hydroxyl, $C_{1-6}$ alkoxy, $NR^6R^{13}$, $C_{1-6}$ alkyl, $C_{1-3}$alkoxy-$C_{1-3}$alkyl wherein $R^{13}$ is $R^7$ or phenyl optionally substituted with one to three groups independently selected from the group consisting of halogen, cyano, $C_{1-3}$ alkyl, $C_{1-3}$ haloalkyl and $C_{1-3}$ alkoxy;
- n is 0 to 3;
- o and p are independently 0 to 4 and o+p$\leq$5;
- q is 0 to 2;
- k, r1 and r2 are independently 0 to 4, and 5$\geq$(r1+r2)$\geq$2; and, acid addition salts, hydrates and solvates thereof;

with the proviso that when $R^4$ is $(CH_2)_nR^{11}$, n is 1 and $R^{11}$ is substituted phenyl, $R^2$ is other than unsubstituted phenyl.

DETAILED DESCRIPTION OF THE INVENTION

In one embodiment of the invention there is provided a compound according to formula I,

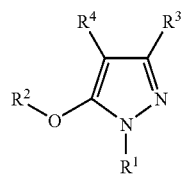

I wherein $R^1$, $R^2$, $R^3$ and $R^4$ are as defined hereinabove; and, hydrates, solvates and acid addition salts thereof.

In another embodiment of the present invention there is provided a compound according to formula I wherein $R^1$ is selected from the group consisting of $C_{1-6}$alkyl, $C_{1-6}$haloalkyl, $C_{3-7}$cycloalkyl, $C_{1-3}$alkoxy-$C_{1-3}$ alkyl and optionally substituted phenyl; $R^2$ is optionally substituted phenyl; $R^4$ is $C_{1-6}$ alkyl, $C_{3-7}$ cycloalkyl, $-(CH_2)_nR^{11}$ or $-(CH_2)_o-O-(CH_2)_pR^{11}$ wherein said alkyl and said cycloalkyl are optionally substituted by $-OH$, $-OR^6$, $-NR^8R^9$, $-C(=Y)Z$, $-X(C=Y)Z$; $R^{11}$ is an optionally substituted phenyl; and, $R^3$ and other groups are as defined hereinabove.

In another embodiment of the present invention there is provided a compound according to formula I wherein $R^1$ is selected from the group consisting of $C_{1-6}$alkyl, $C_{1-6}$haloalkyl, $C_{3-7}$cycloalkyl, $C_{1-3}$alkoxy -$C_{1-3}$alkyl and optionally substituted phenyl; $R^2$ is optionally substituted phenyl; $R^3$ is substituted $C_{1-6}$ alkyl, $-(CH_2)_nR^5$ wherein $R^5$ is IIIa-IIIh, or IIa-c; $R^4$ is $C_{1-6}$ alkyl, $C_{3-7}$ cycloalkyl, $(CH_2)_n$ $R^{11}$ or $-(CH_2)_o-O-(CH_2)_pR^{11}$ wherein said alkyl and said cycloalkyl are optionally substituted by $-OH$, $-OR^6$, $-NR^8R^9$, $-C(=Y)Z$, $-X(C=Y)Z$; $R^{11}$ is an optionally substituted phenyl; and other groups are as defined hereinabove.

In another embodiment of the present invention there is provided a compound according to formula I wherein $R^1$ is selected from the group consisting of $C_{1-6}$alkyl, $C_{1-6}$haloalkyl, $C_{3-7}$cycloalkyl, $C_{1-3}$alkoxy-$C_{1-3}$alkyl and phenyl; $R^2$ is optionally substituted phenyl; $R^3$ is $-(CH_2)_nNR^6R^7$, $-(CH_2)_nC(=O)Z$ or $(CH_2)_nXC(=O)Z$; $R^4$ is $C_{1-6}$ alkyl, $C_{3-7}$ cycloalkyl, $(CH_2)_nR^{11}$ or $-(CH_2)_o-)-(CH_2)_pR^{11}$ wherein said alkyl and said cycloalkyl are optionally substituted by $-OH$, $-OR^6$, $-NR^8R^9$, $-C(=Y)Z$, $-X(C=Y)Z$; $R^{11}$ is an optionally substituted phenyl other groups are as defined hereinabove.

In another embodiment of the present invention there is provided a compound according to formula I wherein $R^1$ is selected from the group consisting of $C_{1-6}$alkyl, $C_{1-6}$haloalkyl, $C_{3-7}$cycloalkyl, $C_{1-3}$alkoxy-$C_{1-3}$alkyl and optionally substituted phenyl; $R^2$ is optionally substituted phenyl; $R^4$ is $C_{1-6}$alkyl, $C_{3-7}$ cycloalkyl, $-(CH_2)_nR^{11}$ or $-(CH_2)_o-O-(CH_2)_pR^{11}$ wherein said alkyl and said cycloalkyl are optionally substituted by $-OH$, $-OR^6$, $-NR^8R^9$, $-C(=Y)Z$, $-X(C=Y)Z$; $R^{11}$ is an optionally substituted heteroaryl ring selected from the group consisting of pyridinyl, pyrimidinyl, pyrazinyl, pyrrole, imidazole, pyrazole and thiophene; and $R^3$ and other groups are as defined hereinabove.

In another embodiment of the present invention there is provided a compound according to formula I wherein $R^1$ is selected from the group consisting of $C_{1-6}$alkyl, $C_{1-6}$haloalkyl, $C_{3-7}$cycloalkyl, $C_{1-3}$alkoxy-$C_{1-3}$alkyl and optionally substituted phenyl; $R^2$ is optionally substituted phenyl; $R^3$ is substituted $C_{1-6}$ alkyl, —$(CH_2)_nR^5$ wherein $R^5$ is IIIa-IIIh or IIa-c; $R^4$ is $C_{1-6}$alkyl, $C_{3-7}$cycloalkyl, —$(CH_2)_nR^{11}$ or —$(CH^2)_o$—O—$(CH_2)_pR^{11}$ wherein said alkyl and said cycloalkyl are optionally substituted by —OH, —$OR^6$, —$NR^8R^9$, —C(=Y)Z, —X(C=Y)Z; $R^{11}$ is an optionally substituted heteroaryl ring; and other groups are as defined hereinabove.

In another embodiment of the present invention there is provided a compound according to formula I wherein $R^1$ is selected from the group consisting of $C_{1-6}$alkyl, $C_{1-6}$haloalkyl, $C_{3-7}$cycloalkyl, $C_{1-3}$alkoxy-$C_{1-3}$alkyl and optionally substituted phenyl; $R^2$ is optionally substituted phenyl; $R^3$ is —$(CH_2)_nNR^6R^7$, —$(CH_2)_nC(=O)Z$ or —$(CH_2)_nXC(=O)Z$; and, $R^4$ is $C_{1-6}$alkyl, $C_{3-7}$cycloalkyl, —$(CH_2)_nR^{11}$ or —$(CH^2)_o$—O—$(CH_2)_pR^{11}$ wherein said alkyl and said cycloalkyl are optionally substituted by —OH, —$OR^6$, —$NR^8R^9$, —C(=Y)Z, —X(C=Y)Z, $R^{11}$ is an optionally substituted heteroaryl ring selected from the group consisting of pyridinyl, pyrimidinyl, pyrazinyl, pyrrole, imidazole, pyrazole and thiophene; and other groups are as defined hereinabove.

In another embodiment of the present invention there is provided a compound according to formula I wherein $R^{11}$ is selected from the group consisting of $C_{1-6}$alkyl, $C_{1-6}$haloalkyl, $C_{3-7}$cycloalkyl, $C_{1-3}$alkoxy-$C_{1-3}$alkyl and optionally substituted phenyl; $R^2$ is optionally substituted phenyl; $R^4$ is $C_{1-6}$alkyl, $C_{3-7}$ cycloalkyl, —$(CH_2)_nR^{11}$ or —$(CH^2)_o$—O—$(CH_2)_pR^{11}$ wherein said alkyl and said cycloalkyl are optionally substituted by —OH, —$OR^6$, —$NR^8R^9$, —C(=Y)Z, —X(C=Y)Z; $R^{11}$ is $N[(CH_2)_2]_2W$ wherein W is selected from the group consisting of $NR_6$, $(CH_2)_s$, $N(C=O)Z$, $CHOR^6$, $CHR^6 CHNHC(=O)Z$ and $CHNR^6R^7$; and, $R^3$ and other groups are as defined hereinabove.

In another embodiment of the present invention there is provided a compound according to formula I wherein $R^1$ is selected from the group consisting of $C_{1-6}$alkyl, $C_{1-6}$haloalkyl, $C_{3-7}$cycloalkyl, $C_{1-3}$alkoxy-$C_{1-3}$alkyl and optionally substituted phenyl; $R^2$ is optionally substituted phenyl; $R^3$ is substituted $C_{1-6}$alkyl, —$(CH_2)_nR^5$ wherein $R^5$ is IIIa-IIIh; or IIa-c; $R^4$ is $C_{1-6}$alkyl, $C_{3-7}$cycloalkyl, —$(CH_2)_nR^{11}$ or —$(CH^2)_o$—O—$(CH_2)_pR^{11}$ wherein said alkyl and said cycloalkyl are optionally substituted by —OH, —$OR^6$, —$NR^8R^9$, —C(=Y)Z, —X(C=Y)Z, $R^{11}$ is $N[(CH_2)_2]_2W$ wherein W is selected from the group consisting of $NR^6$, $(CH_2)_s$, $N(C=O)Z$, $CHOR^6$, $CHR^6 CHNHC(=O)Z$ and $CHNR^6R^7$; and, other groups are as defined hereinabove.

In another embodiment of the present invention there is provided a compound according to formula I wherein $R^1$ is selected from the group consisting of $C_{1-6}$ alkyl, $C_{1-6}$ haloalkyl, $C_{3-7}$ cycloalkyl, $C_{1-3}$ alkoxy-$C_{1-3}$ alkyl and optionally substituted phenyl; $R^2$ is optionally substituted phenyl; $R^3$ is $(CH_2)_nNR^6R^7$, $(CH_2)_nC(=O)Z$ or $(CH_2)_nXC(=O)Z$; $R^4$ is $C_{1-6}$ alkyl, $C_{3-7}$ cycloalkyl, $(CH_2)_nR^{11}$ or —$(CH^2)_o$—O—$(CH_2)_pR^{11}$ wherein said alkyl and said cycloalkyl are optionally substituted by —OH, —$OR^6$, —$NR^8R^9$, —C(=Y)Z, —X(C=Y)Z; $R^{11}$ is $N[(CH_2)_2]_2W$ wherein W is selected from the group consisting of $NR^6$, $(CH_2)_s$, —$N(C=O)Z$, $CHOR^6$, $CHR^6 CHNHC(=O)Z$ and $CHNR^6R^7$ and other groups are as defined hereinabove.

In another embodiment of the present invention there is provided a method for treating an HIV infection, or preventing an HIV infection, or treating AIDS or ARC, comprising administering to a host in need thereof a therapeutically effective amount of a compound of formula I wherein $R^1$, $R^2$, $R^3$ and $R^4$ are as defined hereinabove; and, hydrates, solvates and acid addition salts thereof.

In another embodiment of the present invention there is provided a method for treating an HIV infection, or preventing an HIV infection, or treating AIDS or ARC, comprising co-administering to a host in need thereof a therapeutically effective amount of a compound of formula I wherein $R^1$, $R^2$, $R^3$ and $R^4$ are as defined hereinabove; and, hydrates, solvates and acid addition salts thereof, and at least one compound selected from the group consisting of HIV protease inhibitors, nucleoside reverse transcriptase inhibitors, non-nucleoside reverse transcriptase inhibitors, CCR5 inhibitors and viral fusion inhibitors.

In another embodiment of the present invention there is provided a method for treating an HIV infection, or preventing an HIV infection, or treating AIDS or ARC, comprising co-administering to a host in need thereof a therapeutically effective amount of a compound of formula I wherein $R^1$, $R^2$, $R^3$ and $R^4$ are as defined hereinabove; and, hydrates, solvates and acid addition salts thereof; and a reverse transcriptase inhibitor selected from the group consisting of zidovudine, lamivudine, didanosine, zalcitabine and stavudine, rescriptor, sustiva and viramune and/or a protease inhibitor is selected from the group consisting of saquinavir, ritonavir, nelfinavir, indinavir, amprenavir, lopinavirat and atazanavir.

In another embodiment of the present invention there is provided a method for inhibiting a retrovirus reverse transcriptase comprising administering to a host in need thereof a therapeutically effective amount of a compound of formula I wherein $R^1$, $R^2$, $R^3$ and $R^4$ are as defined hereinabove; and, hydrates, solvates and acid addition salts thereof.

In another embodiment of the present invention there is provided a method for treating an HIV infection, or preventing an HIV infection, or treating AIDS or ARC, wherein the host is infected with a strain of HIV expressing a reverse transcriptase with at least one mutation, comprising administering to a host in need thereof a therapeutically effective amount of a compound of formula I wherein $R^1$, $R^2$, $R^3$ and $R^4$ are as defined hereinabove; and, hydrates, solvates and acid addition salts.

In another embodiment of the present invention there is provided a method for treating an HIV infection, or preventing an HIV infection, or treating AIDS or ARC, wherein said strain of HIV exhibits reduced susceptibility to efavirenz, delavirdine or nevirapine comprising administering to a host in need thereof a therapeutically effective amount of a compound of formula I wherein $R^1$, $R^2$, $R^3$ and $R^4$ are as defined hereinabove; and, hydrates, solvates and acid addition salts thereof.

In another embodiment of the present invention there is provided a pharmaceutical composition comprising a therapeutically effective quantity of a compound of formula I wherein $R^1$, $R^2$, $R^3$ and $R^4$ are as defined hereinabove; and, hydrates, solvates and acid addition salts thereof in admixture with at least one pharmaceutically acceptable carrier or diluent sufficient upon administration in a single or multiple dose regimen for treating diseases mediated by human immunodeficiency virus or to inhibit Definitions The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined hereinabove" refers to the first definition provided in the Summary of the Invention.

The term "alkyl" as used herein denotes an unbranched or branched chain, saturated, monovalent hydrocarbon residue containing 1 to 6 carbon atoms. Examples of alkyl groups include, but are not limited to, lower alkyl groups include methyl, ethyl, propyl, i-propyl, n-butyl, i-butyl, t-butyl or pentyl, isopentyl, neopentyl and hexyl.

The term "alkylene" as used herein means a divalent unbranched or branched saturated hydrocarbon radical consisting solely of carbon and hydrogen atoms, having from 1 to 6 carbon atoms inclusive, unless otherwise indicated. Examples of alkylene radicals include, but are not limited to, methylene, ethylene, propylene, 2-methylethylene, 3-methylpropylene, 2-ethylethylene, pentylene, hexylene, and the like.

The term "haloalkyl" as used herein denotes an unbranched or branched chain alkyl group as defined above wherein 1, 2, 3 or more hydrogen atoms are substituted by a halogen. Examples are 1-fluoromethyl, 1-chloromethyl, 1-bromomethyl, 1-iodomethyl, trifluoromethyl, trichloromethyl, tribromomethyl, triiodomethyl, 1-fluoroethyl, 1-chloroethyl, 1-bromoethyl, 1-iodoethyl, 2-fluoroethyl, 2-chloroethyl, 2-bromoethyl, 2-iodoethyl, 2,2-dichloroethyl, 3-bromopropyl or 2,2,2-trifluoroethyl. The term "fluoroalkyl" refers to a "haloalkyl" wherein the halogen is fluorine The term "cycloalkyl" as used herein denotes a saturated carbocyclic ring containing 3 to 7 carbon atoms, i.e. cyclopropyl, cyclobutyl, cyclopentyl, cyclohexyl or cycloheptyl.

The term "alkenyl" as used herein denotes an unsubstituted hydrocarbon chain radical having from 2 to 6 carbon atoms and having one or two olefinic double bonds. Examples are vinyl, 1-propenyl, 2-propenyl (allyl) or 2-butenyl (crotyl).

The term "alkynyl" as used herein denotes an unsubstituted hydrocarbon chain radical having from 2 to 6 carbon atoms and having one or where possible two triple bonds. Examples are ethynyl, 1-propynyl, 2-propynyl, 1-butynyl, 2-butynyl or 3-butynyl.

The term "alkoxy" as used herein denotes an unsubstituted unbranched or branched chain alkyloxy group wherein the "alkyl" portion is as defined above such as methoxy, ethoxy, n-propyloxy, i-propyloxy, n-butyloxy, i-butyloxy, t-butyloxy, pentyloxy and hexyloxy including their isomers.

The term "haloalkoxy group" as used herein means an -O-haloalkyl group, wherein haloalkyl is as defined above. Examples of haloalkoxy groups include, but are not limited to, 2,2,2-trifluoroethoxy, difluoromethoxy and 1,1,1,3,3,3-hexafluoro-iso-propoxy.

The term "thioalkyl" or "alkylthio" as used herein refers to a group —SR where R is an alkyl group as defined herein such as methylthio, ethylthio, n-propylthio, i-propylthio and n-butylthio including their isomers.

The term "alkoxyalkyl" as used herein refers to the radical R'R"—, wherein R" is an alkoxy radical as defined herein, and R" is an alkylene radical as defined herein with the understanding that the attachment point of the alkoxyalkyl moiety will be on the alkylene radical. Examples are methoxymethyl, methoxyethyl, methoxypropyl, ethoxymethyl, ethoxyethyl, ethoxypropyl, propyloxypropyl, methoxybutyl, ethoxybutyl, propyloxybutyl, butyloxybutyl, t-butyloxybutyl, methoxypentyl, ethoxypentyl, propyloxypentyl including their isomers.

The terms "hydroxyalkyl" as used herein denotes the radical R'R" where R" is an hydroxy radical and R" is alkylene as defined herein and the attachment point of the hydroxyalkyl radical will be on the alkylene radical The term "acyl" as used herein denotes a group of formula C(=O)R ("alkylcarbonyl") wherein R is hydrogen, unbranched or branched alkyl containing 1 to 6 carbon atoms, cycloalkyl containing 3 to 7 carbon atoms, an aryl, an alkoxy, or a NR'R" group. The term acyl includes a group of formula C(=O)OR$^6$ ("alkoxycarbonyl") or C(=O)NR$^6$R$^7$ ("carbamoyl") where R is an alkyl group and R$^6$ and R$^7$ is defined hereinabove.

The term "acylating agent" as used herein refers to a reagent which is capable of transferring an acyl moiety as defined previously to another functional group capable of reacting with the acylating agent. Typically an alkylcarbonyl is introduced by reaction with an anhydride or an acyl halide. The term "anhydride" as used herein refers to compounds of the general structure RC(O)—O—C(O)R wherein is as defined in the previous paragraph. The term "acyl halide" as used herein refers to the group RC(O)X wherein X is bromo or chloro. Typically an alkoxycarbonyl is introduced by reaction with an alkoxycarbonyl chloride. The term "alkoxycarbonyl chloride" as used herein refers to compounds of the general structure ROC(=O)Cl. Typically a carbamoyl group is introduced by reaction with an isocyanate. The term "isocyanate" as used herein refers to compounds of the general structure RN=C=O.

The functional group depicted as "—XC(=Y)Z" wherein X and Y are independently O or NR$^6$ and Z is C$_{1-6}$ alkoxy, NR$^6$R$^7$, alkyl or alkoxyalkyl preferable refer to "guanidines" (—NR$^6$(=NR$^6$) NR$^6$R$^7$), "imidates" (—OC(=NR$^6$)alkyl), "amidines" (—NR$^6$C(=NR$^6$)alkyl), "carbonates" (—OC (=O)OR), "carbamates" (—OC(=O) NR$^6$R$^7$ or —NR$^6$C (=O)OR), "ureas" (—NR$^6$C(=O)NR$^6$R$^7$), "amides" (—NR$^6$C(=O)alkyl) or "esters" (—OC(=O)alkyl ) where R$^6$ and R$^7$ are as defined herein and R is an alkyl group.

The functional group "C(=Y)Z" as used herein refers to esters, amides, imidates and amidines.

The term "heterocyclylalkyl" as used herein means a radical —R'R" where R" is an alkylene radical and R" is a heterocyclyl radical as defined herein. Examples of heterocyclylalkyl radicals include, but are not limited to, tetrahydropyran-2-ylmethyl, 2-piperidinylmethyl, 3-piperidinylmethyl, morpholin-1-ylpropyl, and the like.

The term "alkylamino" as used herein means a radical —NR'R", wherein R" is hydrogen and R" is an alkyl radical as defined herein. The term "dialkylamino" as used herein means a radical —NR'R", wherein R' and R" are alkyl radicals as defined herein. Examples of alkylamino radicals include, but are not limited to, methylamino, ethylamino, cyclopropylmethylamino, dicyclopropylmethylamino, dimethylamino, methylethylamino, diethylamino, di(1-methylethyl)amino, and the like.

The term "aryl" as used herein denotes an optionally substituted monocyclic or polycyclic-aromatic group comprising carbon and hydrogen atoms. Examples of suitable aryl groups include, but are not limited to, phenyl and naphthyl (e. g. 1-naphthyl or 2-naphthyl). Suitable substituents for aryl are selected from the group consisting of C$_{1-6}$ alkyl, C$_{1-6}$ haloalkyl, C$_{1-6}$ alkoxy, C$_{1-6}$ haloalkoxy, C$_{1-6}$ alkylthio, alkoxycarbonyl, CONR$^6$R$^7$, nitro, halogen and cyano.

The term "heteroaryl" or "heteroaromatic" as used herein means a monocyclic or bicyclic radical of 5 to 12 ring atoms having at least one aromatic ring containing four to eight atoms per ring, incorporating one or more N, O, or S heteroatoms, the remaining ring atoms being carbon, with the understanding that the attachment point of said heteroaryl radical will be on said aromatic ring. As well known to those skilled in the art, heteroaryl rings have less aromatic character than their all-carbon counter parts. Thus, for the purposes of the invention, a heteroaryl group need only have some degree of aromatic character. Examples of heteroaryl moieties include monocyclic aromatic heterocycles having 5 to 6 ring atoms and 1 to 3 heteroatoms include, but is not limited to, including, and includes, but is not limited to, pyridinyl, pyrimidinyl, pyrazinyl, pyridazinone, pyrrolyl, pyrazolyl, imidazolyl, triazoline, and oxadiaxoline which can optionally be substituted with one or more, preferably one or two substituents selected from hydroxy, cyano, alkyl, alkoxy, thio, lower haloalkoxy, alkylthio, halo, haloalkyl, alkylsulfmyl, alkylsulfonyl, halogen, amino, alkylamino, dialkylamino, aminoalkyl, alkylaminoalkyl, and dialkylaminoalkyl, nitro, alkoxycarbonyl and carbamoyl, alkylcarbamoyl and dialkylcarbamoyl.

The term "heterocyclylalkyl" as used herein means a radical —R'R" where R" is an alkylene radical and R" is a heterocyclyl radical as defined herein. Examples of heterocyclylalkyl radicals include, but are not limited to, 2-piperidinylmethyl, 3-piperidinylmethyl, morpholin-1-ylpropyl, and the like.

The term "heterocycle" or "heterocyclic" as used herein means a non-aromatic monocyclic or polycyclic ring comprising carbon and hydrogen atoms and one or more N, S, or O heteroatoms. A heterocyclic group can have one or more carbon-carbon double bonds or carbon-heteroatom double bonds in the ring as long as the ring is not rendered aromatic by their presence. Examples of heterocycloalkyl groups include pyrrolidinyl, pyrrolidino, piperidinyl, piperidino, piperazinyl, piperazino, morpholinyl, morpholino, thiomorpholinyl, thiomorpholino. A heterocyclic group can be unsubstituted or substituted with one to three suitable substituents selected from hydroxy, cyano, alkyl, alkoxy, thio, lower haloalkoxy, alkylthio, halo, haloalkyl, alkylsulfinyl, alkylsulfonyl, halogen, amino, alkylamino, dialkylamino, aminoalkyl, alkylaminoalkyl, and dialkylaminoalkyl, nitro, alkoxycarbonyl and carbamoyl, alkylcarbamoyl and dialkylcarbamoyl.

The terms "amino", "alkylamino" and "dialkylamino" as used herein refer to —$NH_2$, —NHR and —$NR_2$ respectively and R is alkyl as defined above. The two alkyl groups attached to a nitrogen in a dialkylamine moiety can be the same or different. The terms "aminoalkyl", "alkylaminoalkyl" and "dialkylaminoalkyl" as used herein refer to $NH_2(CH_2)_n$—, $RHN(CH_2)_n$—, and $R_2N(CH_2)_n$— respectively wherein n is 1 to 6 and R is alkyl as defined above The term "acyl" or "alkylcarbonyl" as used herein denotes a radical of formula C(=O)R wherein R is hydrogen, unbranched or branched alkyl containing 1 to 6 carbon atoms or a phenyl group.

The term "acylamino" as used herein denotes a radical of formula —NH—C(=O)—R wherein R is hydrogen, unbranched or branched alkyl containing 1 to 6 carbon atoms, cycloalkyl containing 3 to 7 carbon atoms or an aryl.

The term "halogen" as used herein means fluorine, chlorine, bromine, or iodine. Correspondingly, the meaning of the term "halo" encompasses fluoro, chloro, bromo, and iodo.

The term "alkylthio" or "thioalkyl" means an —S-alkyl group, wherein alkyl is as defined above such as meththio, ethylthio, n-propylthio, i-propylthio, n-butylthio, hexylthio, including their isomers.

The term "alkylsulfinyl" as used herein means the radical —S(O)R', wherein R' is alkyl as defined herein. Examples of alkylaminosulfonyl include, but are not limited to methylsulfinyl and iso-propylsulfinyl.

The term "alkylsulfonyl" as used herein means the radical —$S(O)_2R'$, wherein R' is alkyl as defined herein. Examples of alkylaminosulfonyl include, but are not limited to methylsulfonyl and iso-propylsulfonyl.

The term "sulfonylating agent" as used herein refers to a reagent which is capable of transferring an alkyl sulfonyl moiety as defined previously to another functional group capable of reacting with the sulfonating agent such as a sulfonyl chloride Cl—$SO_2$—R.

The prefix "carbamoyl" as used herein means the radical —$CONH_2$ The prefix "N-alkylcabamoyl" and "N,N-dialkylcarbamoyl" as used herein means the radical CONHR' or CONR'R" respectively wherein the R' and R" groups are independently alkyl as defined herein.

The term "homologous" as used herein refers to a series of related compounds whose structure at some part of the molecule differs only by a —($CH_2$)— or —$(CH_2)_n$— from another member of the series Compounds of formula I exhibit tautomerism. Tautomeric compounds can exist as two or more interconvertable species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH—⇌—C(—OH)=CH—), amide/imidic acid (—C(=O)—NH—⇌—C(—OH)=N—) and amidine (—C(=NR)—NH—⇌—C(—NHR)=N—) tautomers. The latter two are particularly common in heteroaryl and heterocyclic rings and the present invention encompasses all tautomeric forms of the compounds.

Compounds of formula I which are basic can form pharmaceutically acceptable acid addition salts with inorganic acids such as hydrohalic acids (e.g. hydrochloric acid and hydrobromic acid), sulphuric acid, nitric acid and phosphoric acid, and the like, and with organic acids (e.g. with acetic acid, tartaric acid, succinic acid, fumaric acid, maleic acid, malic acid, salicylic acid, citric acid, methanesulphonic acid and p-toluenesulfonic acid, and the like).

The term "solvate" as used herein means a compound of the invention or a salt, thereof, that further includes a stoichiometric or non-stoichiometric amount of a solvent bound by non-covalent inter-molecular forces. Preferred solvents are volatile, non-toxic, and/or acceptable for administration to humans in trace amounts.

The term "hydrate" as used herein means a compound of the invention or a salt thereof that further includes a stoichiometric or non-stoichiometric amount of water bound by non-covalent intermolecular forces.

The term "wild type" as used herein refers to the HIV virus which possesses the dominant genotype which naturally occurs in the normal population which has not been exposed to reverse transcriptase inhibitors. The term "wild type reverse transcriptase" used herein has refers to the reverse transcriptase with an accession number P03366 deposited in the SwissProt database.

The term "reduced susceptibility" as used herein refers to about a 10 fold, or greater, change in sensitivity of a particular viral isolate compared to the sensitivity exhibited by the wild type virus in the same experimental system

| ABBREVIATIONS | |
|---|---|
| AIBN | azo-bis-isobutyrylnitrile |
| atm | atmospheres |
| BBN or 9-BBN | 9-borabicyclo[3.3.1]nonane |
| Boc | tert-butoxycarbonyl |
| $BOC_2O$ | Di-tert-butyl pyrocarbonate or boc anhydride |
| Bn | benzyl |
| Bu | butyl |
| cbz or Z | benzyloxycarbonyl |
| DABCO | diazabicyclooctane |
| DAST | diethylaminosulfur trifluoride |
| DBU | 1,8-diazabicyclo[5,4,0]undec-7-ene |
| DCE | 1,2-dicloroethane |
| DCM | dichloromethane |
| DEAD | diethyl azodicarboxylate |
| DIAD | di-iso-propylazodicarboxylate |
| DEIPA | diethyl iso-propylamine |
| DIBAL-H | di-iso-butylaluminumhydride |
| DMA | N,N-dimethyl acetamide |
| DMAP | 4-N,N-dimethylaminopyridine |
| DMF | N,N-dimethylformamide |
| dppf | 1,1'-Bis(diphenylphosphino)ferrocene |
| EDCI | 1-(3-dimethylaminopropyl)-3-ethylcarbodiimide hydrochloride |
| EtOAc | ethyl acetate |
| $Et_2O$ | diethyl ether |
| Et | ethyl |
| EtOH | ethanol |
| HPLC | high pressure liquid chromatography |
| LiHMDS | lithium hexamethyl disilazane |
| HOAc | acetic acid |
| i-Pr | iso-propyl |
| Me | methyl |
| MeCN | acetonitrile |
| MeOH | methanol |
| mp | melting point |
| ms | mass spectrum |
| MTBE | methyl t-butyl ether |
| NCA | N-carboxyanhydride |

| ABBREVIATIONS -continued | |
|---|---|
| NBS | N-bromosuccinimide |
| NMP | N-methylpyrrolidone |
| PCC | pyridinium chlorochromate |
| PDC | pyridinium dichromate |
| Pr | propyl |
| psi | pounds per square inch |
| pyr | pyridine |
| rt or RT | room temperature |
| TEA or $Et_3N$ | triethylamine |
| Tf | triflate $CF_3SO_2$— |
| TFA | trifluoroacetic acid |
| THF | tetrahydrofuran |
| TLC | thin layer chromatography |
| TMHD | 2,2,6,6-tetramethylheptane-2,6-dione |
| TsOH | p-toluenesulfonic acid monohydrate |

Compounds

Examples of representative compounds within the scope of the invention are provided in the following table. These examples and preparations are provided to enable those skilled in the art to more clearly understand and to practice the present invention. They should not be considered as limiting the scope of the invention, but merely as being illustrative and representative thereof.

In general, the nomenclature used in this Application is based on AUTONOM™ v.4.0, a Beilstein Institute computerized system for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

TABLE 1

| CPD # | STRUCTURE | NAME | MW [M + H]+ | melting point |
|---|---|---|---|---|
| 1 | (structure) | [5-(3,5-Dichloro-phenoxy)-1-isopropyl-4-methyl-1H-pyrazol-3-yl]-methanol | 315.20 315 | |
| 2 | (structure) | Carbamic acid 5-(3,5-dichloro-phenoxy)-1-isopropyl-4-methyl-1H-pyrazol-3-ylmethyl ester | 358.23 358 | |
| 3 | (structure) | [5-(3-Chloro-phenoxy)-1-isopropyl-4-methyl-1H-pyrazol-3-yl]-methanol | 280.76 281 | |

TABLE 1-continued

| CPD # | STRUCTURE | NAME | MW [M + H]+ | melting point |
|---|---|---|---|---|
| 4 | 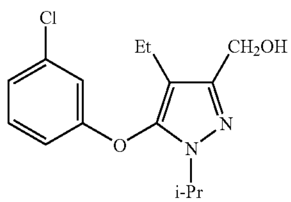 | [5-(3-Chloro-phenoxy)-1-isopropyl-4-ethyl-1H-pyrazol-3-yl]-methanol | 294.78 295 | |
| 5 | 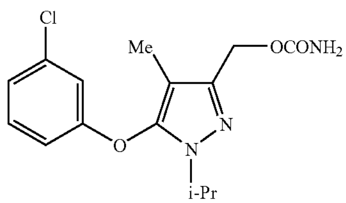 | Carbamic acid 5-(3-chloro-phenoxy)-1-isopropyl-4-methyl-1H-pyrazol-3-ylmethyl ester | 323.78 324 | |
| 6 | 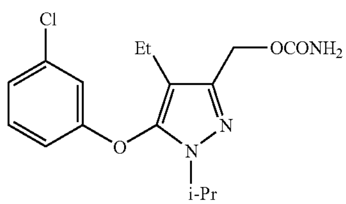 | Carbamic acid 5-(3-chloro-phenoxy)-1-isopropyl-4-ethyl-1H-pyrazol-3-ylmethyl ester | 337.81 338 | |
| 7 | 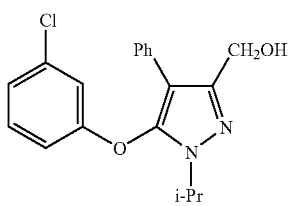 | 4-Benzyl-5-(3-chloro-phenoxy)-1-isopropyl-1H-pyrazol-3-yl]-methanol | 356.86 357 | |
| 8 | 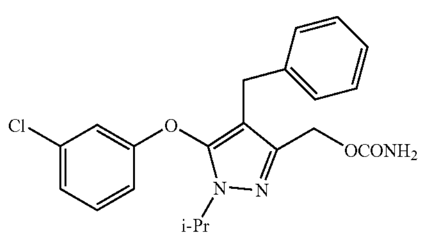 | Carbamic acid 4-benzyl-5-(3-chloro-phenoxy)-1-isopropyl-1H-pyrazol-3-ylmethyl ester | 399.88 400 | |
| 9 | 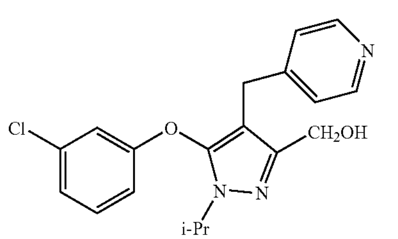 | [5-(3-Chloro-phenoxy)-1-isopropyl-4-pyridin-4-ylmethyl-1H-pyrazol-3-yl]-methanol | 357.84 358 | |
| 10 | 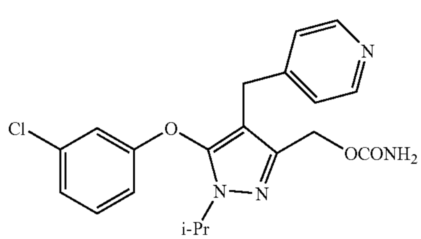 | Carbamic acid 5-(3-chloro-phenoxy)-1-isopropyl-4-pyridin-4-ylmethyl-1H-pyrazol-3-ylmethyl ester | 400.89 401 | |

TABLE 1-continued

| CPD # | STRUCTURE | NAME | MW [M + H]⁺ | melting point |
|---|---|---|---|---|
| 11 | 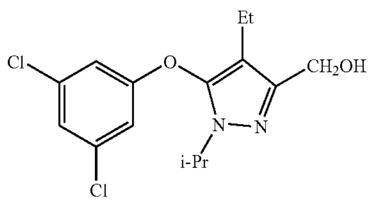 | [5-(3,5-Dichloro-phenoxy)-4-ethyl-1-isopropyl-1H-pyrazol-3-yl]-methanol | 329.23 329 | |
| 12 | 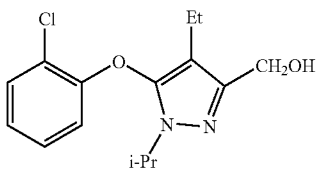 | [5-(2-Chloro-phenoxy)-4-ethyl-1-isopropyl-1H-pyrazol-3-yl]-methanol | 294.78 295 | |
| 13 | 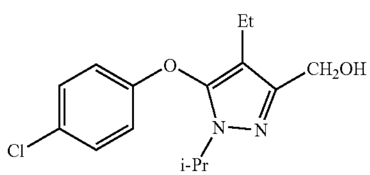 | [5-(4-Chloro-phenoxy)-4-ethyl-1-isopropyl-1H-pyrazol-3-yl]-methanol | 294.78 295 | |
| 14 | 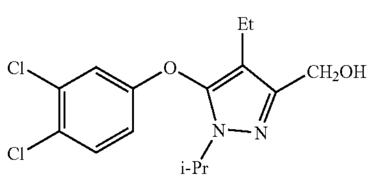 | [5-(3,4-Dichloro-phenoxy)-4-ethyl-1-isopropyl-1H-pyrazol-3-yl]-methanol | 329.23 329 | |
| 15 | 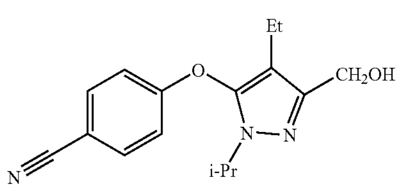 | 4-(4-Ethyl-5-hydroxymethyl-2-isopropyl-2H-pyrazol-3-yloxy)-benzonitrile | 285.35 286 | |
| 16 | 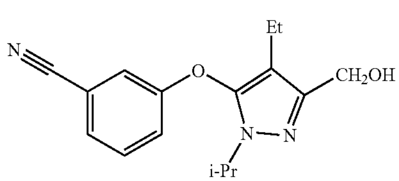 | 3-(4-Ethyl-5-hydroxymethyl-2-isopropyl-2H-pyrazol-3-yloxy)-benzonitrile | 285.35 286 | |
| 17 | 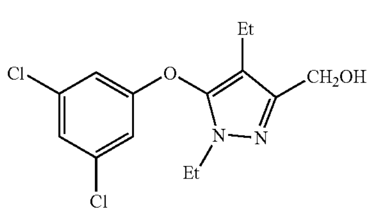 | [5-(3,5-Dichloro-phenoxy)-1,4-diethyl-1H-pyrazol-3-yl]-methanol | 315.20 | |
| 18 | 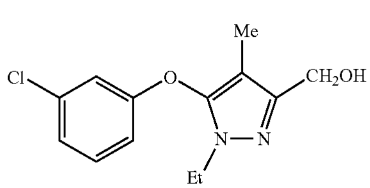 | [5-(3-Chloro-phenoxy)-1-ethyl-4-methyl-1H-pyrazol-3-yl]-methanol | 266.73 267 | |

TABLE 1-continued

| CPD # | STRUCTURE | NAME | MW [M + H]+ | melting point |
|---|---|---|---|---|
| 19 | 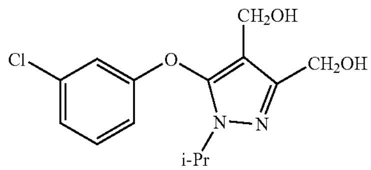 | [5-(3-Chloro-phenoxy)-4-hydroxymethyl-1-isopropyl-1H-pyrazol-3-yl]-methanol | 296.76 297 | |
| 20 | 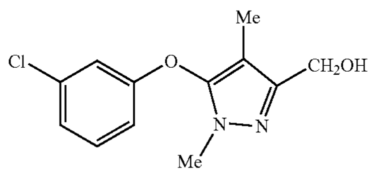 | [5-(3-Chloro-phenoxy)-1,4-dimethyl-1H-pyrazol-3-yl]-methanol | 252.70 253 | |
| 21 | 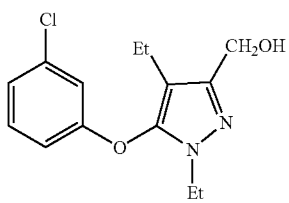 | [5-(3-Chloro-phenoxy)-1,4-diethyl-1H-pyrazol-3-yl]-methanol | 280.76 281 | |
| 22 | 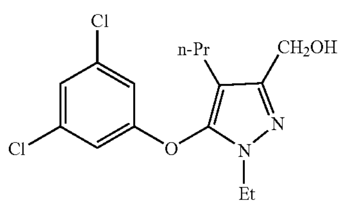 | [5-(3,5-Dichloro-phenoxy)-1-ethyl-4-propyl-1H-pyrazol-3-yl]-methanol | 329.23 329 | |
| 23 | 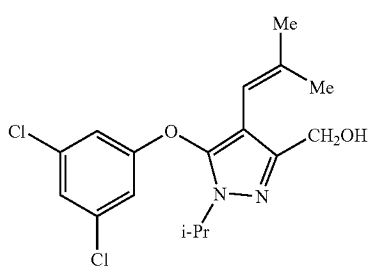 | [5-(3,5-Dichloro-phenoxy)-1-isopropyl-4-(2-methyl-propenyl)-1H-pyrazol-3-yl]-methanol | 355.27 355 | |
| 24 | 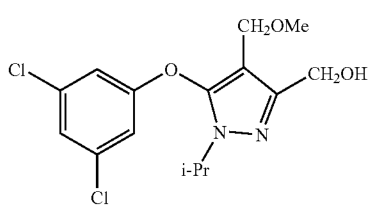 | [5-(3,5-Dichloro-phenoxy)-1-isopropyl-4-methoxymethyl-1H-pyrazol-3-yl]-methanol | 345.23 345 | |
| 25 | 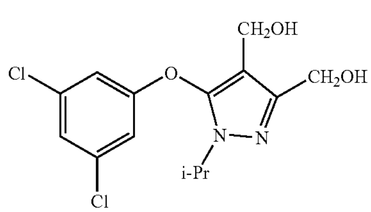 | [5-(3,5-Dichloro-phenoxy)-4-hydroxymethyl-1-isopropyl-1H-pyrazol-3-yl]-methanol | 331.20 331 | |

TABLE 1-continued

| CPD # | STRUCTURE | NAME | MW [M + H]+ | melting point |
|---|---|---|---|---|
| 26 | 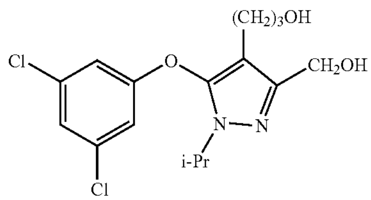 | 3-[5-(3,5-Dichloro-phenoxy)-3-hydroxymethyl-1-isopropyl-1H-pyrazol-4-yl]-propan-1-ol | 359.26 359 | |
| 27 | 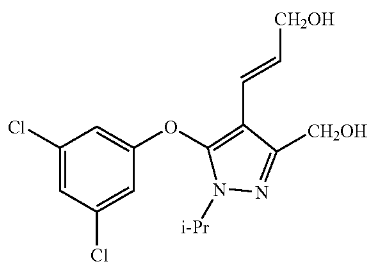 | 3-[5-(3,5-Dichloro-phenoxy)-3-hydroxymethyl-1-isopropyl-1H-pyrazol-4-y]-propenol | 357.24 357 | |
| 28 | 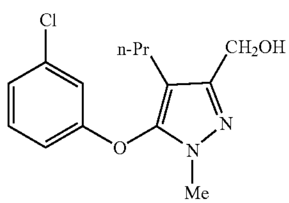 | [5-(3-Chloro-phenoxy)-1-methyl-4-propyl-1H-pyrazol-3-yl]-methanol | 280.76 281 | |
| 29 | 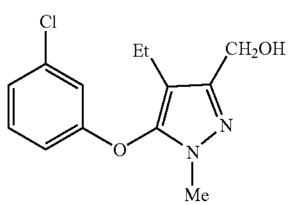 | [5-(3-Chloro-phenoxy)-4-ethyl-1-methyl-1H-pyrazol-3-yl]-methanol | 266.73 267 | |
| 30 | 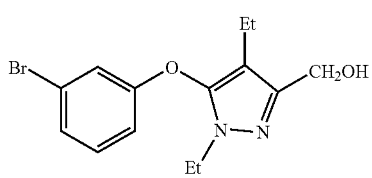 | [5-(3-Bromo-phenoxy)-1,4-diethyl-1H-pyrazol-3-yl]-methanol | 325.21 325 | |
| 31 | 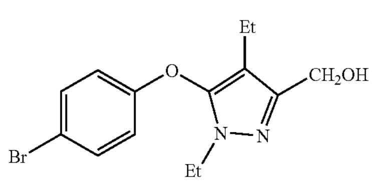 | [5-(4-Bromo-phenoxy)-1,4-diethyl-1H-pyrazol-3-yl]-methanol | 325.21 325 | |
| 32 | 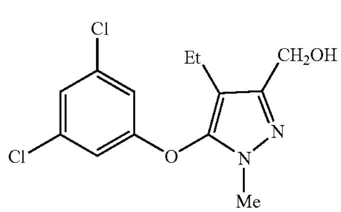 | [5-(3,5-Dichloro-phenoxy)-4-ethyl-1-methyl-1H-pyrazol-3-yl]-methanol | 301.17 [M]+ = 300 | |

TABLE 1-continued

| CPD # | STRUCTURE | NAME | MW [M + H]+ | melting point |
|---|---|---|---|---|
| 33 | 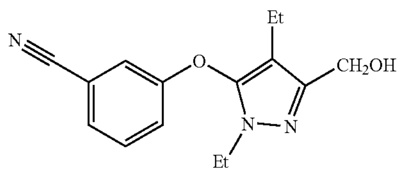 | 3-(2,4-Diethyl-5-hydroxymethyl-2H-pyrazol-3-yloxy)-benzonitrile | 271.32 272 | |
| 34 | 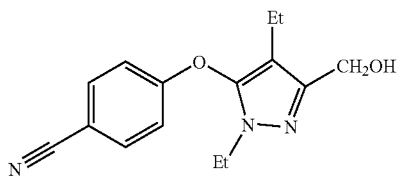 | 4-(2,4-Diethyl-5-hydroxymethyl-2H-pyrazol-3-yloxy)-benzonitrile | 271.32 272 | |
| 35 | 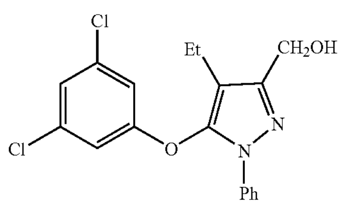 | [5-(3,5-Dichloro-phenoxy)-4-ethyl-1-phenyl-1H-pyrazol-3-yl]-methanol | 363.25 363 | |
| 36 | 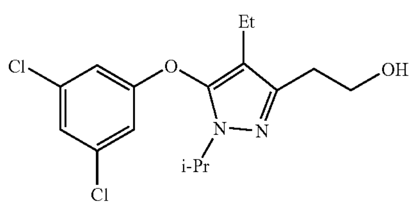 | 2-[5-(3,5-Dichloro-phenoxy)-4-ethyl-1-isopropyl-1H-pyrazol-3-yl]-ethanol | 343.26 343 | |
| 37 | 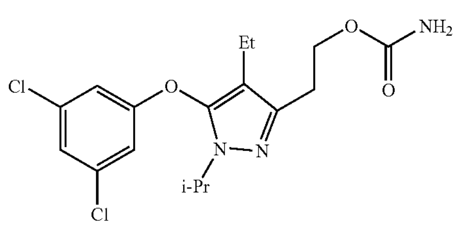 | Carbamic acid 2-[5-(3,5-dichloro-phenoxy)-4-ethyl-1-isopropyl-1H-pyrazol-3-yl]-ethyl ester | 386.28 386 | |
| 38 | 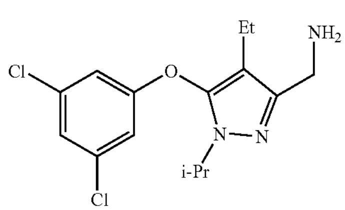 | C-[5-(3,5-Dichloro-phenoxy)-4-ethyl-1-isopropyl-1H-pyrazol-3-yl]-methylamine | 328.24 328 | |
| 39 | 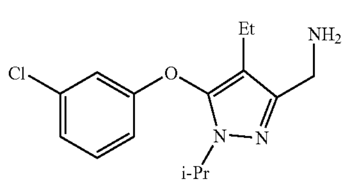 | C-[5-(3-chloro-phenoxy)-4-ethyl-1-isopropyl-1H-pyrazol-3-yl]-methylamine | 293.80 294 | |

TABLE 1-continued

| CPD # | STRUCTURE | NAME | MW [M + H]+ | melting point |
|---|---|---|---|---|
| 40 | 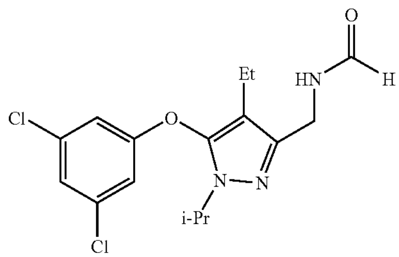 | N-[5-(3,5-Dichloro-phenoxy)-4-ethyl-1-isopropyl-1H-pyrazol-3-ylmethyl]-formamide | 356.25 356 | |
| 41 | 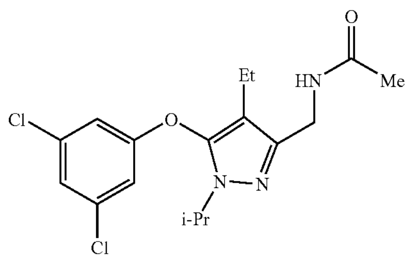 | N-[5-(3,5-Dichloro-phenoxy)-4-ethyl-1-isopropyl-1H-pyrazol-3-ylmethyl]-acetamide | 370.28 370 | |
| 42 | 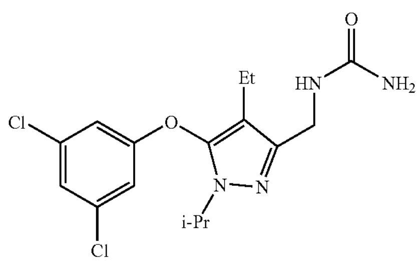 | [5-(3,5-Dichloro-phenoxy)-4-ethyl-1-isopropyl-1H-pyrazol-3-ylmethyl]urea | 371.27 371 | |
| 43 | 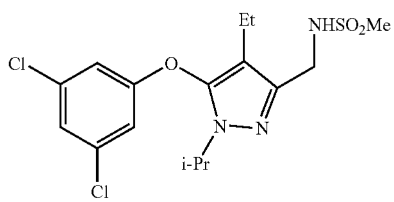 | N-[5-(3,5-Dichloro-phenoxy)-4-ethyl-1-isopropyl-1H-pyrazol-3-ylmethyl]-methanesulfonamide | 406.33 406 | |
| 44 | 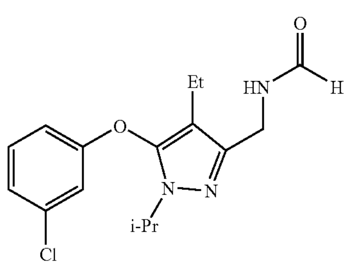 | N-[5-(3-chloro-phenoxy)-4-ethyl-1-isopropyl-1H-pyrazol-3-ylmethyl]-formamide | 321.81 322 | |
| 45 | 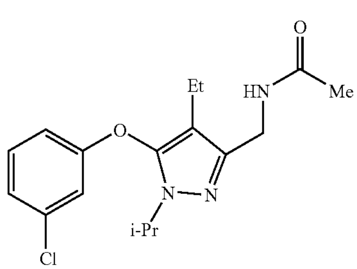 | N-[5-(3-chloro-phenoxy)-4-ethyl-1-isopropyl-1H-pyrazol-3-ylmethyl]-acetamide | 335.84 336 | |

TABLE 1-continued

| CPD # | STRUCTURE | NAME | MW [M + H]+ | melting point |
|---|---|---|---|---|
| 46 | 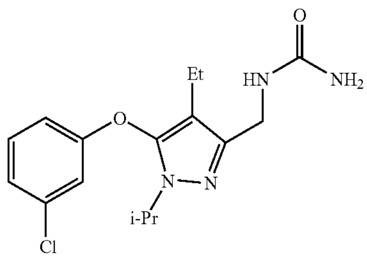 | [5-(3-chloro-phenoxy)-4-ethyl-1-isopropyl-1H-pyrazol-3-ylmethyl]urea | 336.82 337 | |
| 47 | 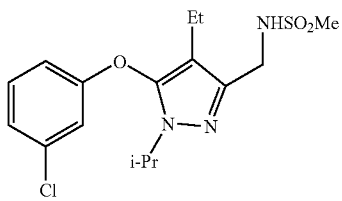 | N-[5-(3-chloro-phenoxy)-4-ethyl-1-isopropyl-1H-pyrazol-3-ylmethyl]-methanesulfonamide | 371.89 372 | |
| 48 | 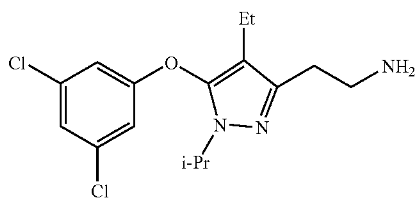 | 2-[5-(3,5-Dichloro-phenoxy)-4-ethyl-1-isopropyl-1H-pyrazol-3-yl]-ethylamine | 342.27 342 | |
| 49 | 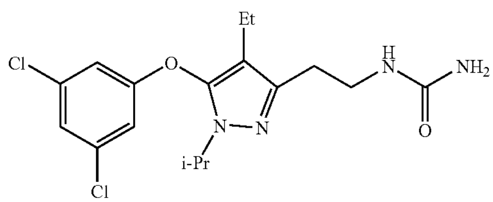 | {2-[5-(3,5-Dichloro-phenoxy)-4-ethyl-1-isopropyl-1H-pyrazol-3-yl]-ethyl}-urea | 385.30 385 | |
| 50 | 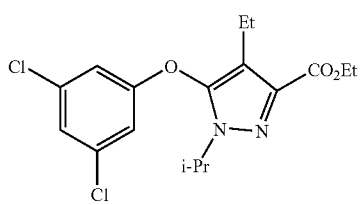 | 5-(3,5-Dichloro-phenoxy)-4-ethyl-1-isopropyl-1H-pyrazole-3-carboxylic acid ethyl ester | 371.27 371 | |
| 51 | 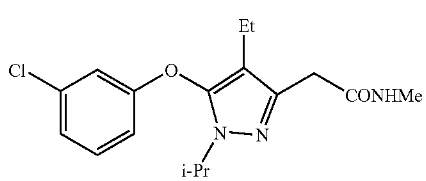 | 2-[5-(3-Chloro-phenoxy)-4-ethyl-1-iso-propyl-1H-pyrazol-3-yl]-N-methyl-acetamide | 321.81 | |
| 53 | 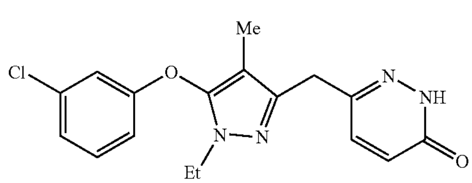 | 6-[5-(3-Chloro-phenoxy)-4-methyl-1-ethyl-1H-pyrazol-3-ylmethyl]-2H-pyridazin-3-one | 344.80 345 | |

TABLE 1-continued

| CPD # | STRUCTURE | NAME | MW [M + H]+ | melting point |
|---|---|---|---|---|
| 54 | 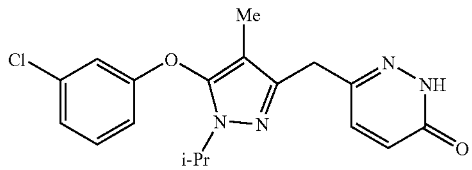 | 6-[5-(3-Chloro-phenoxy)-4-methyl-1-isopropyl-1H-pyrazol-3-ylmethyl]-2H-pyridazin-3-one | 358.83 359 | |
| 55 | 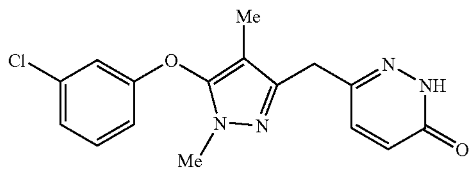 | 6-[5-(3-Chloro-phenoxy)-4-methyl-1-methyl-1H-pyrazol-3-ylmethyl]-2H-pyridazin-3-one | 330.78 331 | |
| 56 | 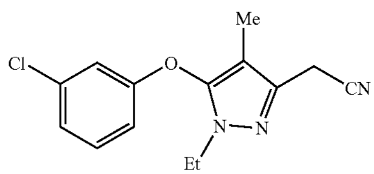 | 5-(3-Chloro-phenoxy)-1-isopropyl-4-methyl-1H-pyrazol-3-yl]-acetonitrile | 275.74 276 | |
| 57 | 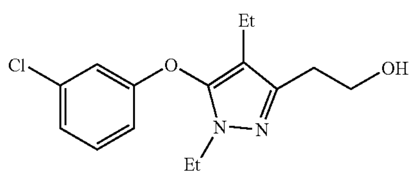 | 2-[5-(3-chloro-phenoxy)-1,4-diethyl-1H-pyrazol-3-yl]-ethanol | 294.8 | |
| 58 | 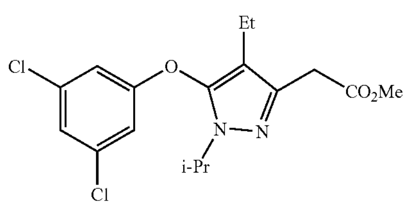 | [5-(3,5-Dichloro-phenoxy)-4-ethyl-1-isopropyl-1H-pyrazol-3-yl]-acetic acid methyl ester | 371.3 | |
| 59 | 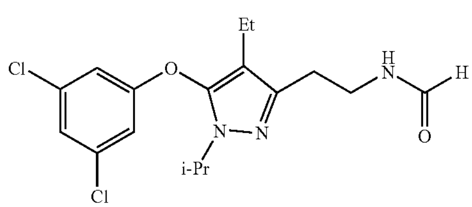 | N-[5-(3,5-Dichloro-phenoxy)-4-ethyl-1-isopropyl-1H-pyrazol-3-ylmethyl]-formamide | 370.3 | |
| 60 | 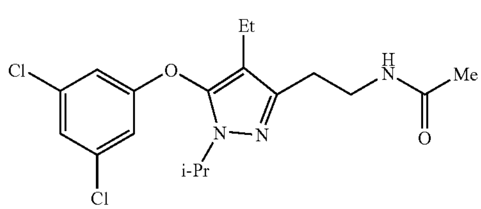 | N-[5-(3,5-Dichloro-phenoxy)-4-ethyl-1-isopropyl-1H-pyrazol-3-ylmethyl]-acetamide | 384.3 | |
| 61 | 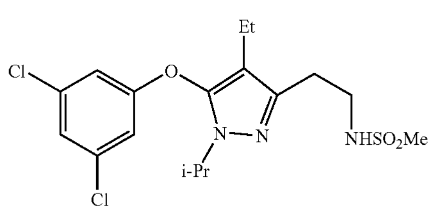 | N-[5-(3,5-Dichloro-phenoxy)-4-ethyl-1-isopropyl-1H-pyrazol-3-ylmethyl]-methanesulfonamide | 420.4 | |

TABLE 1-continued

| CPD # | STRUCTURE | NAME | MW [M + H]+ | melting point |
|---|---|---|---|---|
| 62 | 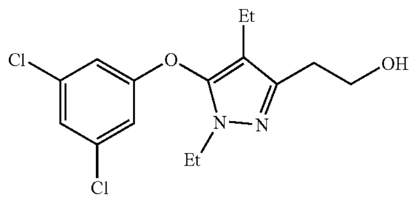 | 2-[5-(3,5-Dichloro-phenoxy)-1,4-diethyl-1H-pyrazol-3-yl]-ethanol | 329.2 | |
| 63 | 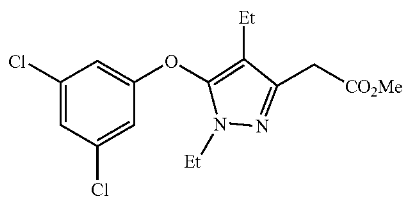 | [5-(3,5-Dichloro-phenoxy)-1,4-diethyl-1H-pyrazol-3-yl]-acetic acid methyl ester | 357.2 | |
| 64 | 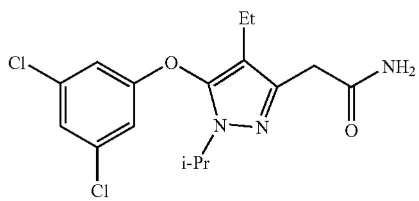 | 2-[5-(3,5-Dichloro-phenoxy)-4-ethyl-1-isopropyl-1H-pyrazol-3-yl]-acetamide | 356.2 | |
| 65 | 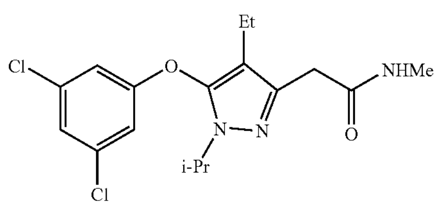 | 2-[5-(3,5-Dichloro-phenoxy)-4-ethyl-1-isopropyl-1H-pyrazol-3-yl]-N-methyl-acetamide | 370.3 | |
| 66 | 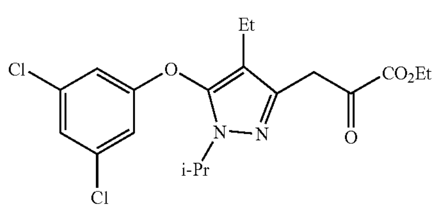 | [5-(3,5-Dichloro-phenoxy)-4-ethyl-1-isopropyl-1H-pyrazol-3-yl]-acetic acid ethyl ester | 385.2 385 | |
| 67 | 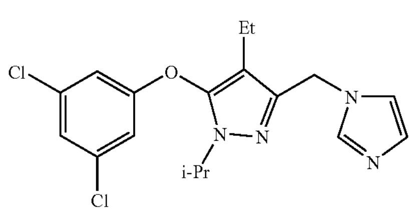 | 5-(3,5-Dichloro-phenoxy)-4-ethyl-3-imidazol-1-ylmethyl-1-isopropyl-1H-pyrazole | 379.3 379 | |
| 68 | 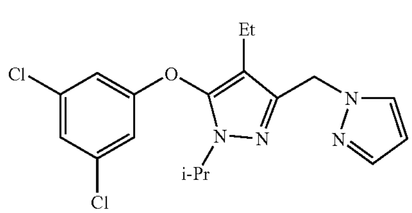 | 5-(3,5-Dichloro-phenoxy)-4-ethyl-1-isopropyl-3-pyrazol-1-ylmethyl-1H-pyrazole | 379.3 379 | |

TABLE 1-continued

| CPD # | STRUCTURE | NAME | MW [M + H]+ | melting point |
|---|---|---|---|---|
| 69 | 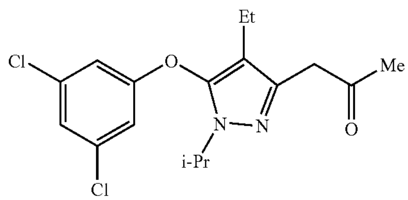 | 1-[5-(3,5-Dichloro-phenoxy)-4-ethyl-1-isopropyl-1H-pyrazol-3-yl]-propan-2-one | 355.3 355 | |
| 70 | 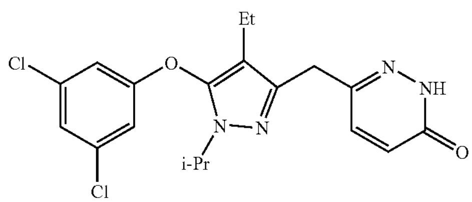 | 6-[5-(3,5-Dichloro-phenoxy)-4-ethyl-1-isopropyl-1H-pyrazol-3-ylmethyl]-2H-pyridazin-3-one | 407.3 407 | |
| 71 | 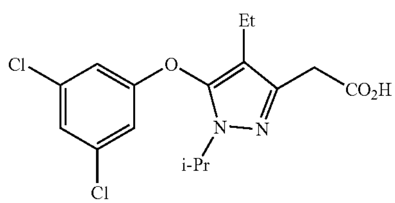 | [5-(3,5-Dichloro-phenoxy)-4-ethyl-1-isopropyl-1H-pyrazol-3-yl]-acetic acid | 357.2 357 | |
| 72 | 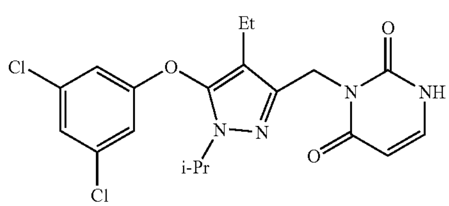 | 3-[5-(3,5-Dichloro-phenoxy)-4-ethyl-1-isopropyl-1H-pyrazol-3-ylmethyl]-1H-pyrimidine-2,4-dione | 423.3 M+ = 423 | |
| 73 | 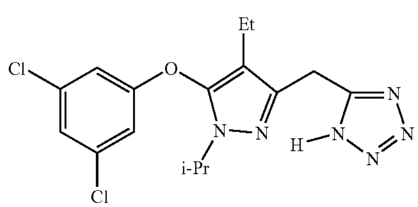 | 5-[5-(3,5-Dichloro-phenoxy)-4-ethyl-1-isopropyl-1H-pyrazol-3-ylmethyl]-2H-tetrazole | 381.3 381 | |
| 74 | 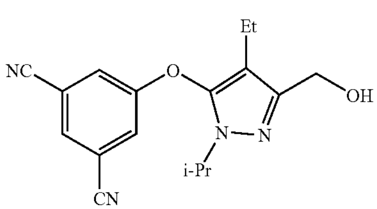 | 5-(4-Ethyl-5-hydroxymethyl-2-isopropyl-2H-pyrazol-3-yloxy)-isophthalonitrile | 310.4 311 | |
| 76 | 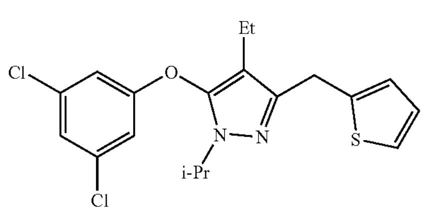 | 5-(3,5-Dichloro-phenoxy)-4-ethyl-1-isopropyl-3-thiophen-2-ylmethyl-1H-pyrazole | 395.4 M+ = 395 | |

TABLE 1-continued

| CPD # | STRUCTURE | NAME | MW [M + H]+ | melting point |
|---|---|---|---|---|
| 78 | 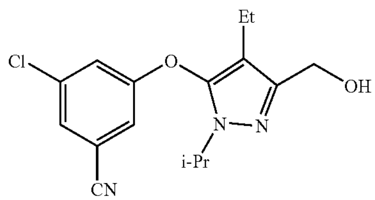 | 3-Chloro-5-(4-ethyl-5-hydroxymethyl-2-isopropyl-2H-pyrazol-3-yloxy)-benzonitrile | 319.8 320 | |
| 79 | 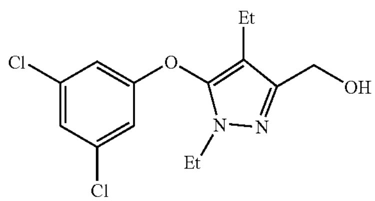 | 3-Chloro-5-(2,4-diethyl-5-hydroxymethyl-2H-pyrazol-3-yloxy)-benzonitrile | 305.8 306 | |
| 80 | 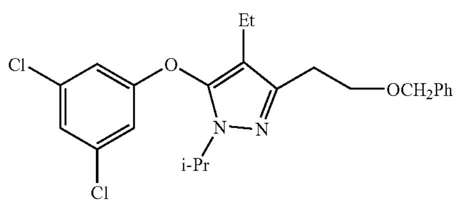 | 3-(2-Benzyloxy-ethyl)-5-(3,5-dichloro-phenoxy)-4-ethyl-1-isopropyl-1H-pyrazole | 433.4 433 | |
| 81 | 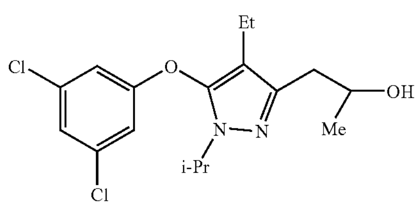 | 1-[5-(3,5-Dichloro-phenoxy)-4-ethyl-1-isopropyl-1H-pyrazol-3-yl]-propan-2-ol | 357.3 357 | |
| 82 | 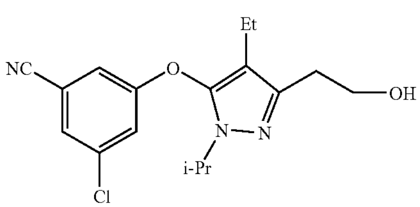 | 3-Chloro-5-[4-ethyl-5-(2-hydroxy-ethyl)-2-isopropyl-2H-pyrazol-3-yloxy]-benzonitrile | 333.8 334 | |
| 83 | 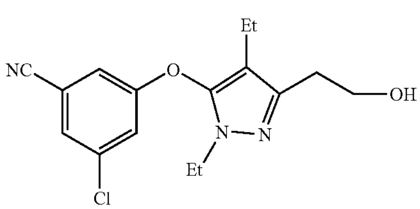 | 3-Chloro-5-[2,4-diethyl-5-(2-hydroxy-ethyl)-2H-pyrazol-3-yloxy]-benzonitrile | 319.8 320 | |
| 84 | 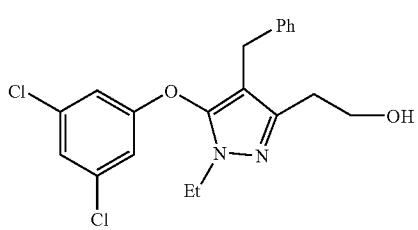 | 2-[4-Benzyl-5-(3,5-dichloro-phenoxy)-1-ethyl-1H-pyrazol-3-yl]-ethanol | 391.3 391 | |

TABLE 1-continued

| CPD # | STRUCTURE | NAME | MW [M + H]+ | melting point |
|---|---|---|---|---|
| 85 | 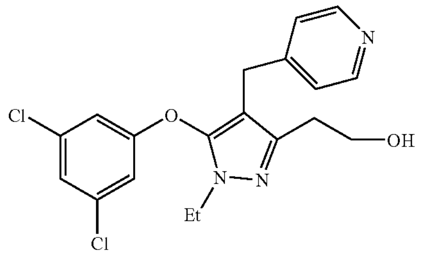 | 2-[5-(3,5-Dichloro-phenoxy)-1-ethyl-4-pyridin-4-ylmethyl-1H-pyrazol-3-yl]-ethanol | 392.3 392 | 103-105.8 |
| 86 | 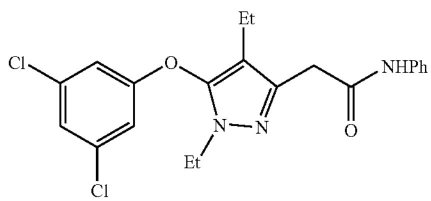 | 2-[5-(3,5-Dichloro-phenoxy)-1,4-iethyl-1H-pyrazol-3-yl]-N-phenyl-acetamide | 418.3 418 | 112.2-115.9 |
| 87 | 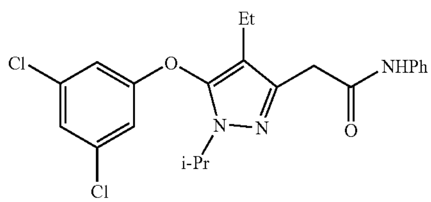 | 2-[5-(3,5-Dichloro-phenoxy)-4-ethyl-1-isopropyl-1H-pyrazol-3-yl]-N-phenyl-acetamide | 432.4 432 | 118.9-120.9 |
| 88 | 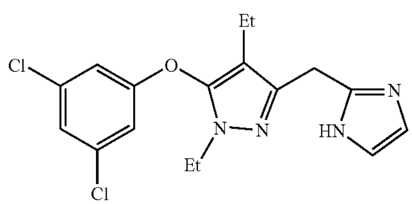 | 5-(3,5-Dichloro-phenoxy)-1,4-diethyl-3-(1H-imidazol-2-ylmethyl)-1H-pyrazole | 365.3 365 | 145-148 |
| 90 | 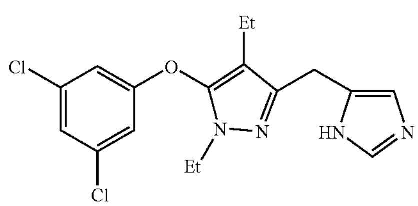 | 5-(3,5-Dichloro-phenoxy)-1,4-diethyl-3-(3H-imidazol-4-ylmethyl)-1H-pyrazole | 365.3 365 | 142-145.2 |
| 91 | 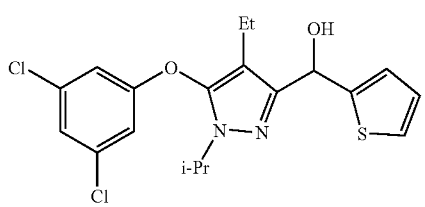 | [5-(3,5-Dichloro-phenoxy)-4-ethyl-1-isopropyl-1H-pyrazol-3-yl]-thiophen-2-yl-methanol | 411.4 411 | |
| 92 | 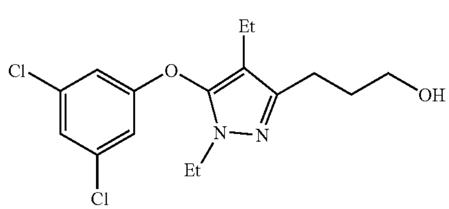 | 3-[5-(3,5-Dichloro-phenoxy)-1,4-diethyl-1H-pyrazol-3-yl]-propan-1-ol | 343.3 343 | |

TABLE 1-continued

| CPD # | STRUCTURE | NAME | MW [M + H]+ | melting point |
|---|---|---|---|---|
| 93 | 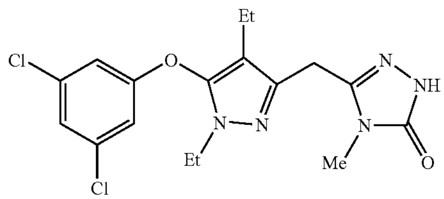 | 5-[5-(3,5-Dichloro-phenoxy)-1,4-diethyl-1H-pyrazol-3-ylmethyl]-4-methyl-2,4-dihydro-[1,2,4]triazol-3-one | 396.3 | |
| 94 | 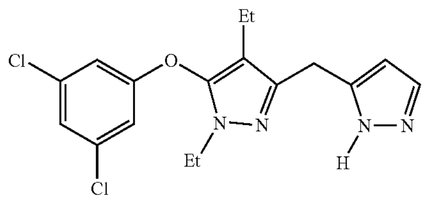 | 5-(3,5-Dichloro-phenoxy)-1,4-diethyl-3-(2H-pyrazol-3-ylmethyl)-1H-pyrazole | 365.3 | |
| 95 | 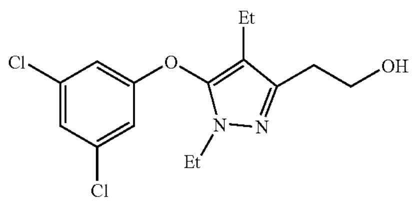 | 3-Chloro-5-[2,4-diethyl-5-(2-hydroxy-ethyl)-2H-pyrazol-3-yloxy]-benzonitrile | 319.8 | |

Preparation of Compounds

Compounds of the present invention can be made by a variety of methods depicted in the illustrative synthetic reaction schemes shown and described below. The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, Volumes 1-21; R. C. LaRock, *Comprehensive Organic Transformations*, 2$^{nd}$ edition Wiley-VCH, New York 1999; *Comprehensive Organic Synthesis*, B. Trost and I. Fleming (Eds.) vol. 1-9 Pergamon, Oxford, 1991; *Comprehensive Heterocyclic Chemistry*, A. R. Katritzky and C. W. Rees (Eds) Pergamon, Oxford 1984, vol. 1-9; *Comprehensive Heterocyclic Chemistry II*, A. R. Katritzky and C. W. Rees (Eds) Pergamon, Oxford 1996, vol. 1-11; and *Organic Reactions*, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Some compounds in following schemes are depicted with generalized substituents; however, one skilled in the art will immediately appreciate that the nature of the R groups can varied to afford the various compounds contemplated in this invention. Moreover, the reaction conditions are exemplary and alternative conditions are well known. The reaction sequences in the following examples are not meant to limit the scope of the invention as set forth in the claims.

The 2H-pyrazol-3-ols used as synthetic precursors for compounds of the present invention are prepared by cyclization of N-substituted hydrazines or hydrazine and an optionally substituted β-ketoester (scheme 1). (R. H. Wiley and P. Wiley, *Pyrazolines, Pyrazolidines* and *Derivatives* in *The Chemistry of Heterocyclic Compounds*, vol. 20, A. Weissberger (ed.), J. Wiley and Sons, New York, 1964, pp. 18-31 and 95-97; K. Kirschke, 1H-Pyrazoles, in *Houben-Weyl Methoden der Organischen Chemie* E8B Hetarene III Teil 2, George Thieme Verlag, Stuttgart, 1994 pp. 433-448).

Scheme 1

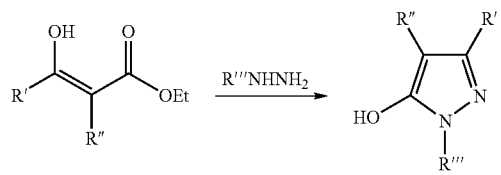

C-3 substituted carboethoxy pyrazoles were prepared by reacting sodium 1,2-bis-ethoxycarbonyl-ethenoxide and a substituted hydrazine or hydrazine hydrate in refluxing benzene to yield 2a and 3 respectively (Scheme 2). Alkylation of the N-1 of pyrazole 3 was accomplished by protecting the hydroxyl substituent, which can be accomplished conveniently as a silyl ether, e.g. 5, (other protecting groups are described in T. W. Greene and P. G. M. Wuts, *Protective Groups in Organic Synthesis*, Wiley Interscience, New York, N.Y., 3$^{rd}$ edition, 1999) followed by alkylation and deprotection to yield 6. Alkylation of the nitrogen is typically achieved by sequentially treating 5 with a base and an alkylating agent. Typical bases for the transformation are sodium carbonate, potassium carbonate, sodium hydride, potassium hydride, potassium t-butoxide in a solvent such as dimethylformamide (DMF), dimethylsulfoxide (DMSO), N-methyl pyrrolidinone (NMP), acetonitrile and tetrahydrofuran. Alternatively the cyclization can be carried out with a hydrazine substituted with a labile protecting group (e.g., p —$CH_2C_6H_4OMe$) which subsequently can be cleaved to yield 3.

by treatment with $POCl_3$. (K. Kirschke, 1H-Pyrazoles, in *Houben-Weyl Methoden der Organischen Chemie* E8B Hetarene III Teil 2, George Thieme Verlag, Stuttgart, 1994 pp. 638-641).

Displacement of the chloride with an optionally substituted sodium phenoxide or sodium pyridinoxide in DMF yields the 5-aryloxy pyrazole 7. The reaction is carried out in THF or other polar aprotic solvents such as dimethylsulfoxide (DMSO), dimethylacetamide (DMA) or N,N-dimethylformamide (DMF) in the presence of a base such as such as n-butyl lithium, sodium hydride, or sodium tert-butoxide. The reaction is conveniently carried out under an inert atmosphere such as nitrogen or argon atmosphere at a reaction temperature from 0° C. to boiling temperature of the reaction mixture, preferably at a reaction temperature between about 10° C. and about 180° C.

4-Alkyl pyrazoles were prepared by reacting the aldehyde with an alkyl Grignard reagent to produce a secondary carbinol 8 and subsequently reducing the secondary carbinol

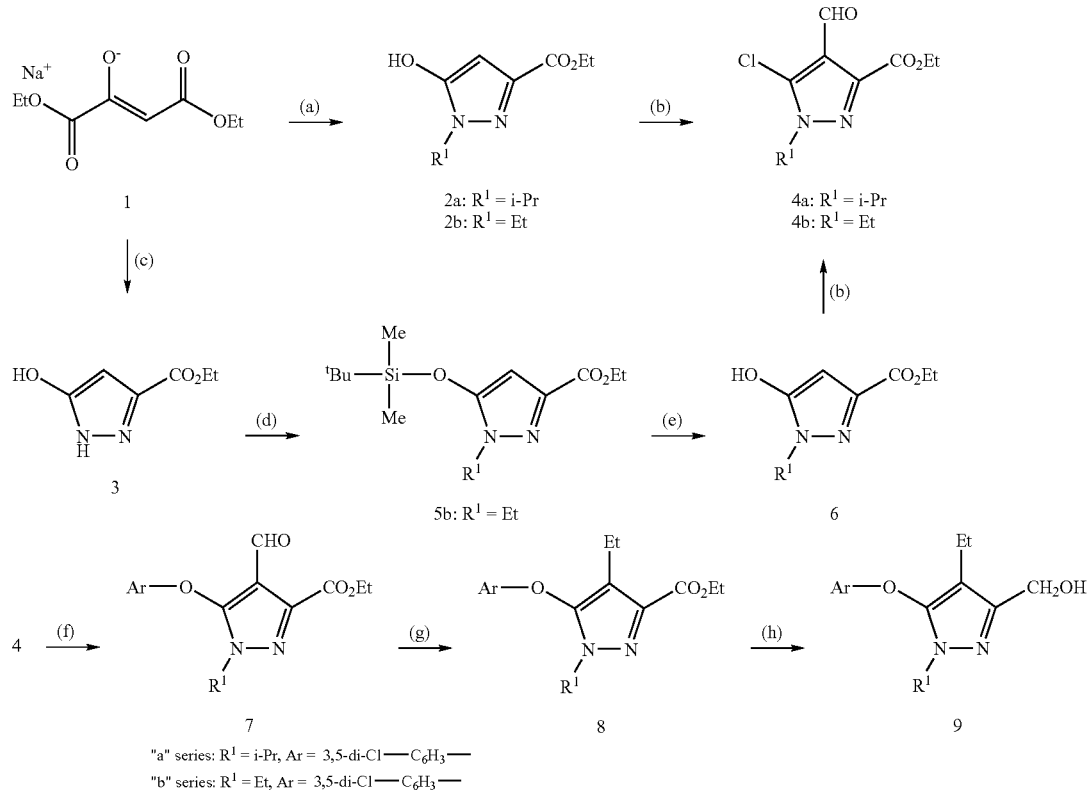

Introduction of a formyl group into the 4-position under Vilsmeyer conditions occurs with concomitant displacement of the hydroxy group by a chloride to yield functionalized pyrazole intermediate 4. (G. Jones and S. P. Stanforth, *Organic Reactions*, Wiley & Sons, New York, 1997, vol. 49, chapter 1). The C-5 hydroxy substituent is readily displaced by chlorine even in the absence of the C-4 formyl substituent with triethylsilane to yield 9. (Scheme 3) One skilled in the art will recognize that although the scheme is depicted with a methyl Grignard reagent other alkyl and alkenyl Grignard reagents as well as other organometallic derivatives commonly used in organic synthesis, including, but not limited to, lithium, zinc, cadmium, zirconium, sodium, potassium, also will suffice. The reaction is carried out at temperatures ranging from −78° C. to 0° C. in inert solvents which include diethyl ether, THF, 1,2-dimethoxyethane, hexane.

Reduction of aldehyde 7 to carbinol 12 is accomplished with a hydride reducing agent. Typical reducing agents include sodium borohydride, lithium borohydride, and sodium triacetoxyborohydride. Alternatively catalytic hydrogenation or other reducing agents known in the art can be applied. NaBH$_4$ reductions are conveniently carried out in an organic solvent for example alcoholic solvents such as methanol, ethanol, propanol or ethers such as THF, diethyl ether, or dimethoxyethane or a mixture of the mentioned solvents. Aprotic solvents are required for more reactive hydride transfer reagents. The reaction is carried out at a reaction temperature between about −10° C. and about 60° C., preferably at room temperature. The reduction reaction can also be carried out as described in textbooks about organic chemistry e.g. from J. March (1992), "Advanced Organic Chemistry: Reactions, Mechanisms, and Structure", 4$^{th}$ ed. John Wiley & Sons. The carbinol can then be further derivatized 13 (R$^{13}$=acyl, alkyl, aralkyl, aryl, carbamoyl).

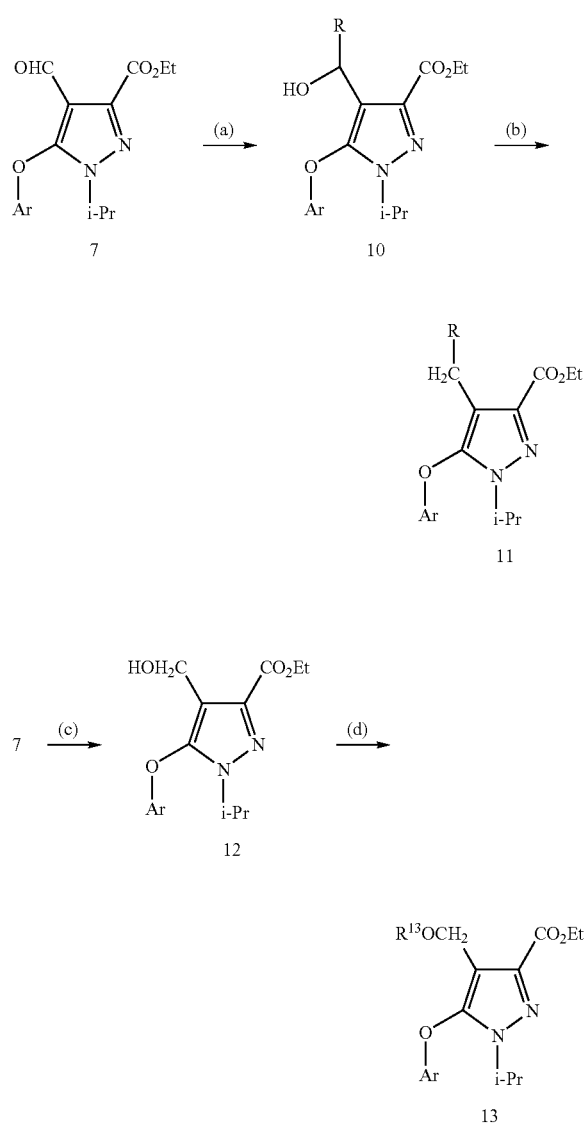

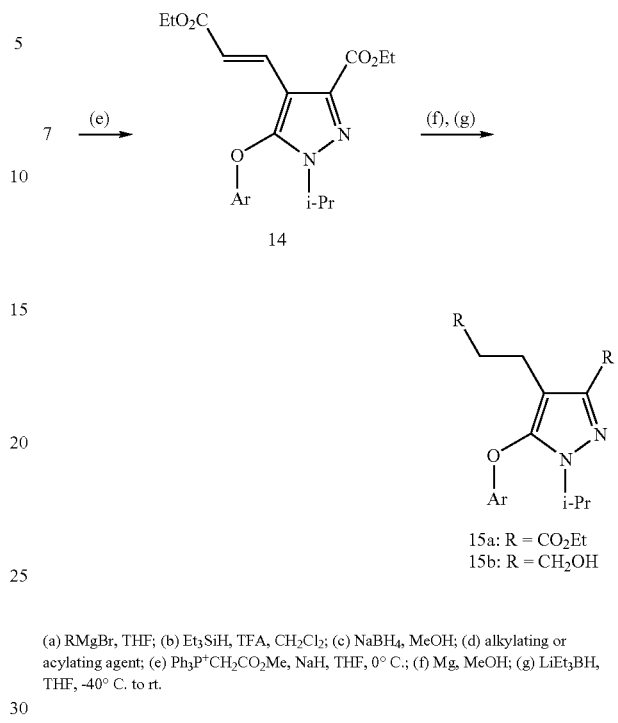

(a) RMgBr, THF; (b) Et$_3$SiH, TFA, CH$_2$Cl$_2$; (c) NaBH$_4$, MeOH; (d) alkylating or acylating agent; (e) Ph$_3$P$^+$CH$_2$CO$_2$Me, NaH, THF, 0° C.; (f) Mg, MeOH; (g) LiEt$_3$BH, THF, -40° C. to rt.

Alternatively, the C-4 aldehyde can be converted to an alkene 14 (Scheme 3) or substituted alkene with a Wittig reagent or Emmons-Wadsworth reagent (see J. W. Schulenberger and S. Archer, *Organic Reactions*, Wiley & Sons, New York 1965 vol. 14, chapter 1, pp. 1-51; J. March, *Advanced Organic Chemistry*, 4$^{th}$ ed., John Wiley & Sons, New York, 1992, pp. 956-963). The olefination reaction is carried out by procedures similar to those described in the literature, for example in the presence of a strong base such as n-butyl lithium or preferably sodium hydride in an organic solvent such as anhydrous ethers such as diethyl ether, dibutyl ether, dioxane, preferably anhydrous THF under inert atmosphere such as nitrogen or argon atmosphere at a reaction temperature from 0° C. to 80° C., preferably at a reaction temperature between about 5° C. and about 50° C. The olefination affords an efficient method for homologation of the C-4 substituent.

Optionally the resulting alkene may be reduced to 15a by catalytic hydrogenation with standard platinum, palladium and ruthenium catalyst on supporting materials such as activated carbon or alumina, or generally as described in textbooks about organic chemistry (e.g. J. March (1992), *Advanced Organic Chemistry: Reactions, Mechanisms, and Structure*, 4$^{th}$ ed. John Wiley & Sons, New York, 1992, pp. 771-780) under a pressure from 1-40 atmospheres; or, by dissolving metal reduction (Yuon et al., *Tetrahedron Lett* 1986 27:2409; Hudlicky et al. *Tetrahedron Lett*. 1987 28:5287) if desired. Appropriate solvents for the hydrogenation reaction are organic solvent such as alcohols (e.g. MeOH, EtOH), ethers (e.g. THF, 1,2-dimethoxyethane), esters (e.g. EtOAc), halogenated hydrocarbons (e.g dichloromethane) or hydrocarbons (e.g. hexane, cyclohexane and toluene). Dissolving metal reductions are carried out with magnesium in MeOH. Reduction of 15a with diisobutylaluminum hydride (DIBAL-H), lithium aluminum hydride or lithium triethylborohydride affords the diol 15b.

Introduction of substituents at the C-4 can also be accomplished by an acylation of the hydroxypyrazole (Scheme 4). The acyl derivative 16 (step a) wherein $R^{15}$ is alkyl, aryl or aralkyl is formed by reacting the corresponding acid chloride with a 5-hydroxy-pyrazole 2. The reaction is conveniently carried out under conditions known from acylation reactions for example in an inert solvent, such as ethers e.g. anhydrous THF, diethyl ether, dibutyl ether, dioxane, or a mixture of the mentioned solvents, at a reaction temperature from room temperature to boiling temperature of the reaction mixture in the presence of a catalyst such as $Ca(OH)_2$, $K_2CO_3$, $AlCl_3$, $BF_3$, $FeCl_3$, $SnCl_4$ or $ZnCl_2$.

The 5-hydroxy pyrazole 16 is easily converted to a 5-chloropyrazole derivative 17 with a chlorinating agent such as $(COCl)_2$, HCl, $PCl_5$, $PCl_3$, $SOCl_2$ or $POCl_3$. The reaction is conveniently carried out under an inert atmosphere such as nitrogen or argon atmosphere at a reaction temperature from room temperature to boiling temperature of the reaction mixture. Preferably, the reaction is carried out in the presence of phosphorus oxychloride ($POCl_3$) at a reaction temperature between about 50° C. and about 180° C. Optionally, the reaction can be carried out in an organic solvent such as halogenated hydrocarbons (e.g. dichloromethane or chloroform), hydrocarbons (e.g. cyclohexane, methyl cyclohexane, decalin, benzene, toluene, o-xylene, m-xylene or p-xylene) or a mixtures of the mentioned solvents.

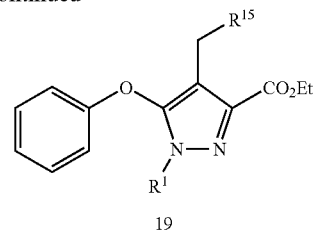

(a) $R^{15}COCl$, $Ca(OH)_2$, $Et_2O$; (b) $POCl_3$, $CH_2Cl_2$;
(c) Ar—OH, NaH, DMF; (d) $Et_3SiH$, TFA, $CH_2Cl_2$.

Reduction of the carbonyl 18 to alkane 19 (scheme 4, step d) is accomplished with alkylsilane in the presence of a protic or Lewis acid. The reaction is conveniently carried out with trimethylsilane, triethylsilane or tripropylsilane. Trifluoroacetic acid (TFA) is the preferred protic acid and $SnCl_4$ is the preferred Lewis acid (D. L. Comins et al., *Tetrahedron. Lett.*, 1986, 27:1869) at a reaction temperature from 0° C. to 80° C., preferably at a reaction temperature between about 5° C. and about 50° C. Option the oxo derivative 18 is directly reduced to the corresponding methylene 19 using other procedures known in the art, e.g., the Clemmensen reduction, the Wolff-Kischner reduction and hydogenolysis of thioacetals or reduction.

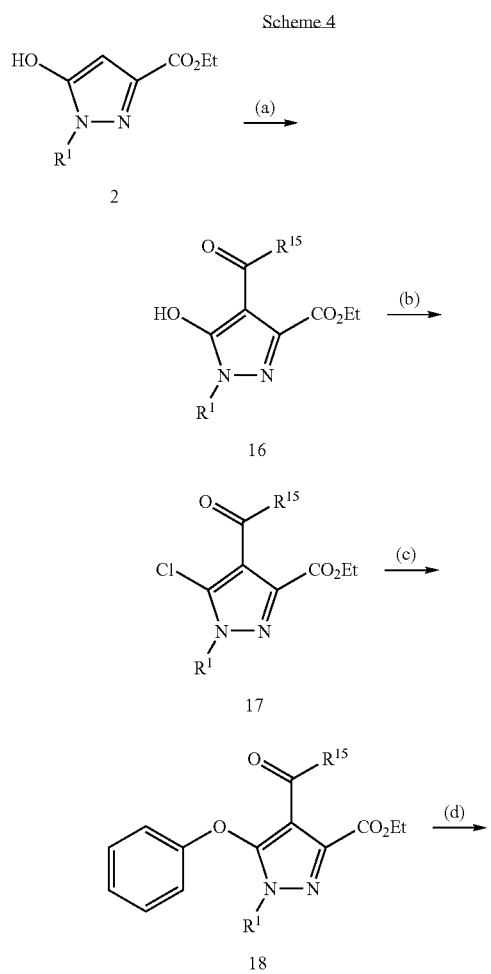

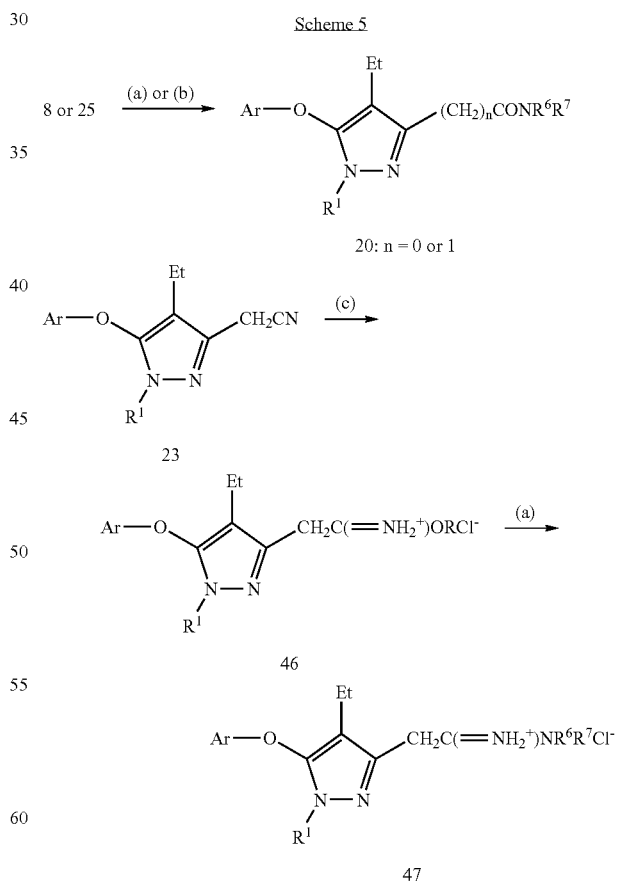

(a) $HNR^6R^7$, THF; (b) (i) NaOH, MeOH, (ii) $SOCl_2$, (iii) $HNR^6R^7$, pyridine, ether; (c) ROH, HCl (gas)

The C-3 ester or pyrazoles 8 and 25 (Scheme 5) are converted into the corresponding amides 45 by transamidation or by saponification of the ester which can be then be converted to the amide by standard methodology (J. March *Advanced Organic Chemistry*, 4th Ed J Wiley & Sons: New York, 1991; pp 419-424). A pyrazole with a nitrile 23 is converted to the corresponding imidate 46 by treating the nitrile with an alcohol in the presence of hydrochloric acid. R. Sandler and W. Karo, *Organic Functional Group Preparations*, 2nd Ed., Academic Press, New York, vol. 111, 1986, pp.314-330). Amidines 47 are prepared by treating an imidate with a ammonia or a substituted amine or, alternatively by sequential treatment of an amide 45 with phosphorus oxychloride and ammonia or a substituted amine.

The C-3 carbinol in 9 (Scheme 6) can be converted to esters (20; $R^{13}$=C(=O)$R^6$), carbonates (20; $R^{13}$=C(=O)O$R^6$) and carbamates (20; $R^{13}$=C(=O)NH$R^6$) by condensation of 9 with acid chlorides or anhydrides, alkylchloroformates, and isocyanates respectively (J. March *Advanced Organic Chemistry* 4th Ed J Wiley & Sons: New York, 1991; pp 392-396 and 891-892; S. R. Sandler and W. Karo, *Organic Functional Group Preparations*, 2nd Ed., Academic Press, New York, vol. I, 1983, pp. 299-304; vol. II, 1986, 260-271). Ethers (20; $R^{13}$=alkyl or aralkyl) can be prepared by the Williamson ether synthesis or Mitsunobu reaction (March supra. pp. 386-87; S. R. Sandler and W. Karo, *Organic Functional Group Preparations*, 2nd Ed., Academic Press, New York, vol. I, 1983, pp. 129-133). The Williamson ether synthesis may be preferably carried out in an organic solvent such as polar aprotic solvents like N,N-dimethylacetamide or N,N-dimethylformamide (DMF), acetonitrile or THF using a base such as sodium hydride, lithium hydride, potassium hydride, potassium tert-butoxide, lithium carbonate, sodium carbonate, potassium carbonate or organic amines such as triethylamine or an N-alkyl morpholine such as N-methylmorpholine at a reaction temperature between about -10° C. and about 60° C., preferably at room temperature. Alternatively, the carbinol can be converted to an alkyl halide and reacted with an alkali metal phenoxide.

Amines 21 were prepared from the alcohol 9 by the Mitsunobu condensation (March supra. pp. 414-415). Treatment of 21 with acylating agents provides amides (22; $R^{13}$=CO$R^6$), carbamates (22; $R^{13}$=CO$_2R^6$) and ureas (22; $R^{13}$=C(=O)NH$R^6$). Guanidines (22; $R^{13}$=C(=NH)N$R^6R^7$) are prepared from the thiourea (22; $R^{13}$=C(=S)NH$R^6$) by sequential treatment with dimethylsulfate and an amine. (Y. Yamamoto et al. *Synthesis and Chemistry of Guanidines in The Chemistry of Amidines and Imidates*, S. Patai and Z. Rappoport (Eds.), Wiley & Sons, Chichester 1991, Chapter 10, pps.489-492). Condensation of the amine with a sulfonylating agent produces the corresponding sulfonamide (22; $R^{13}$=SO$_2R^6$).

Scheme 6

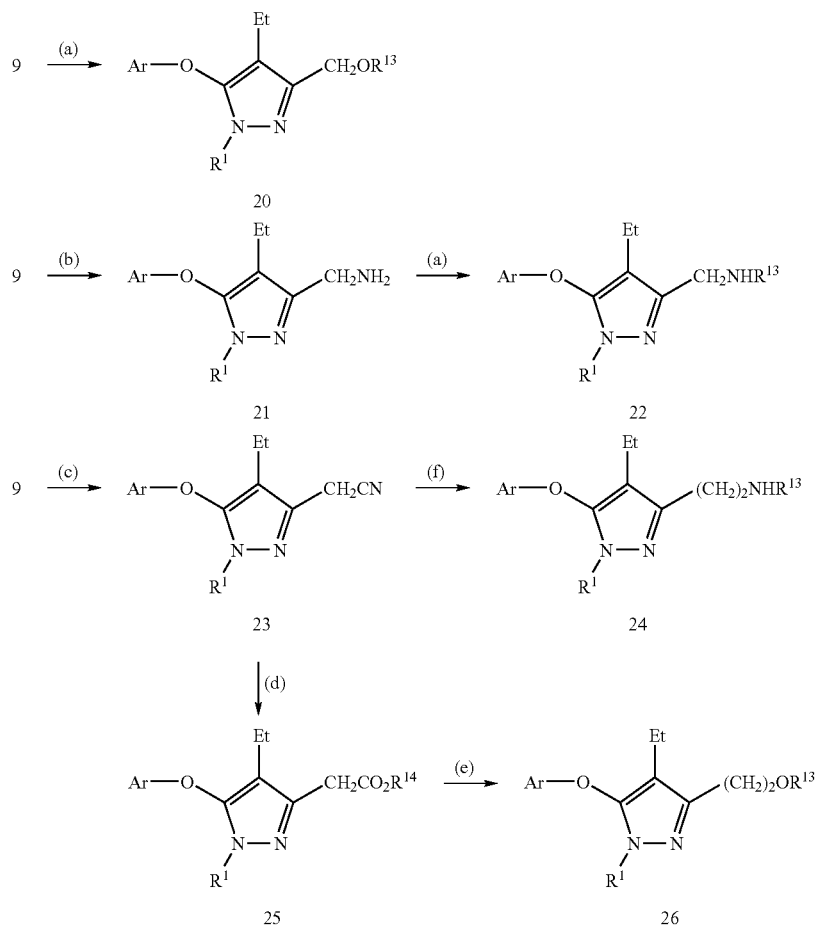

(a) acylating or alkylating agent; (b) (i) DEAD, Ph$_3$P, phthalimide, (ii) NH$_2$NH$_2$
(c) (i) SOCl$_2$, (ii) NaCN, DMF; (d) (i) HCl, HOAc, H$_2$O, (ii) MeOH, HCl; (e)
(i) LiEt$_3$BH, THF, (ii) NaBH$_4$, MeOH (e) acylating or alkylating agent; (f) (i)
DIBAL-H, (ii) NaBH$_4$, MeOH; CH$_2$Cl$_2$.

The homologous amine and carbinol derivatives are prepared by a two-step process comprising conversion of the primary alcohol to an alkyl halide and displacement of the halide with sodium cyanide. The resulting nitrile 23 can be reduced to the amine 24 ($R^{13}$=H) by sequential treatment with diisobutylaluminum hydride and sodium borohydride. The resulting amine 24 ($R^{13}$=H) can be treated with acylating, alkylating and sulfonylating agents. Hydrolysis and esterification of 23 yielded the corresponding ester 25 ($R^{14}$=Me) which was reduced to alcohol (26; $R^{13}$=H) and further derivatized with alkylating and acylating agents as described above.

under acidic conditions with aqueous hydrochloric acid and acetic acid resulted in hydrolysis, decarboxylation and concomitant hydrolysis of the chloropyridazine to produce pyridazinone 28. 2-Oxo-2,3-dihydro-1,3,4-oxadiazoles 30a was prepared by cyclization of an acyl hydrazide 29 with phosgene (or equivalents such as carbonyl diimidazole, alkyl chloroformates and the like) to directly produce the desired oxadiazole. (A. Hetzheim, 1,3,4 *Oxadiazoles in Houben-Weyl Methoden der Organischen Chemie*, Hetarene III/Teil 3, Band E8c; Verlag, Stuttgart; 1994, pp531-536) (Scheme 7) 2-Oxo-2,3-dihydro-1,3,4-thiadiazoles 30b are prepared by condensation of an 0-alkyl imidate 31 and

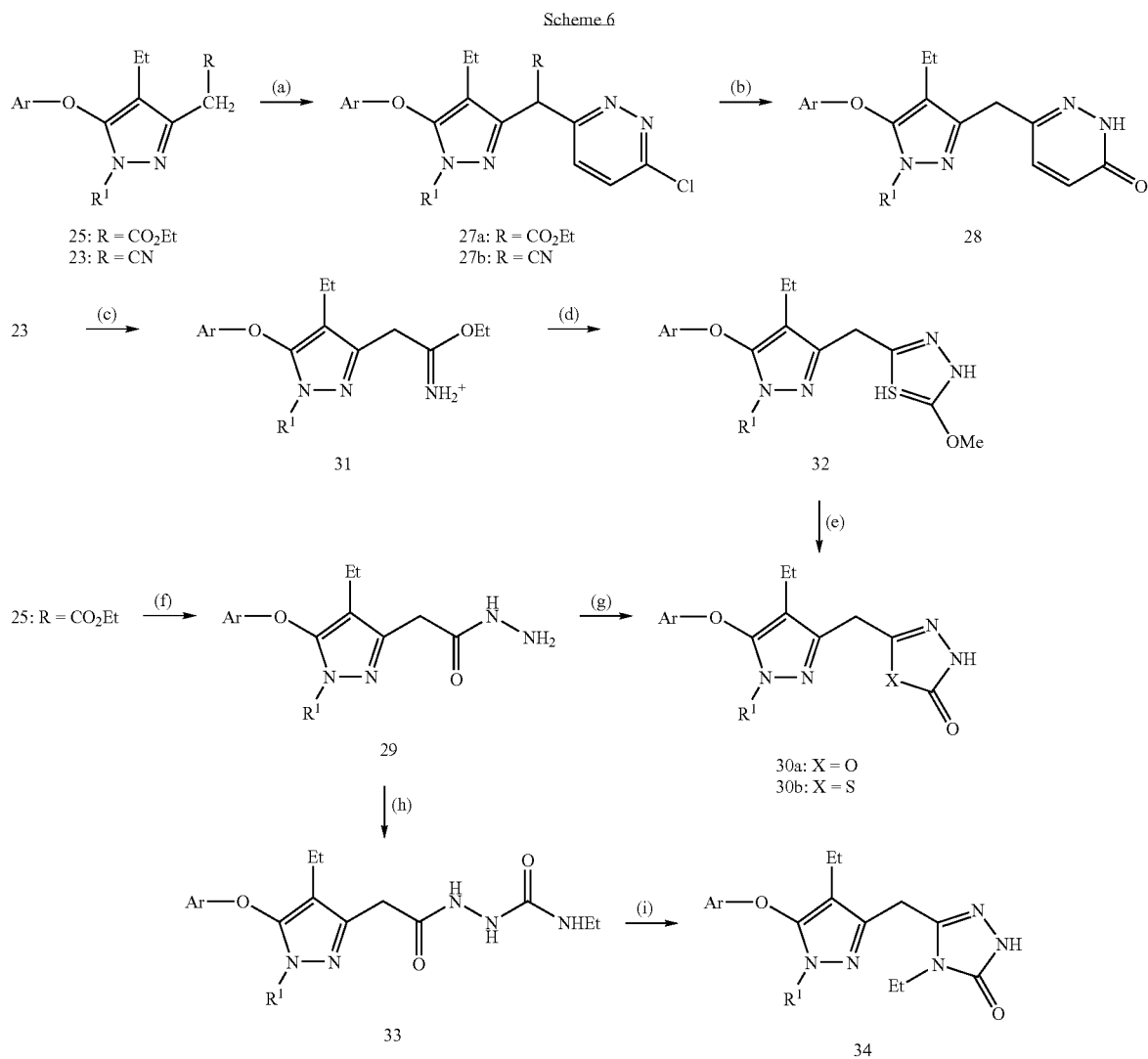

(a) 3,6-dichloropyrazine, NaH, DMF; (b) HOAc, HCl, $H_2O$; (c) HCl, EtOH; (d) $H_2$NNHC(=S)OMe; dioxane; (e) HOAc; (f) $NH_2NH_2$, EtOH; (g) ClC(=O)Cl, pyr, $CH_2Cl_2$; (h) EtNCO, THF; (i) KOH, MeOH.

Introduction of heterocyclylalkyl substituents onto the C-3 position of the pyrazole was accomplished by modification of the nitrile 23 or the ester 25. Pyridazinones 28 were prepared by base-catalyzed condensation of the appropriately substituted ester or nitrile and 3,6-dichloropyridazine (Scheme 7). The condensation is accomplished efficiently with sodium hydride and DMF. Hydrolysis of 27a or 27b methoxythiocarbonyl hydrazide which produce a 2-methoxy-3,4-thidiazole derivative 32 which was hydrolyzed to the corresponding 2-oxo-2,3-dihydro-1,3,4-thiadiazole 30b under acidic conditions (H. Kristinsson et al. *Helv. Chim. Acta* 1982 65:2606). Alternatively, cyclization of N-acyl-N'-alkoxycarbonyl hydrazides with Lawesson's reagent can directly produce the thiadiazole (B. P. Rasmussen et al. *Bull.*

Soc. Chim. Fr. 1985 62). Triazolones 34 can be prepared by carbamoylation of an acyl hydrazide 29 with ethyl isocyanate to yield an N-acyl-N-carbamoylhydrazide 33 cyclized to the triazolone 34 upon treatment with methanolic potassium hydroxide.

Other heteroaryl-containing side chains were accessible by exploiting variations readily accessible at the 3-position which. Halomethyl compounds (see, e.g., 37) are susceptible to nucleophilic displacement by heteroatoms which produced the imidazol-1-ylmethyl (67), pyrazol-1-ylmethyl (68) and N-substituted uracils (72) compounds. (see examples 41 and 42) Linkages to a carbon atom of heteroaryl substituents can be introduced by adding an appropriately protected organometallic compound to a pyrazole with aldehyde-containing side chains (e.g. 105) followed by reductive removal of the carbinol moiety and subsequent deprotection if appropriate (see examples 43-44, 46 and 47). Heteroaryl and heterocycles also can be introduced by [1,3]dipolar cycloadditions of 1,3-dipolar compounds and to multiple bonds (see, e.g, J. March *Advanced Organic Chemistry*, $4^{th}$ Ed J Wiley & Sons: New York, 1991; pp 836-839). Thus cycloaddition of azides to nitriles affords the tetrazole 73 (example 36).

Dosage and Administration

Compounds of the present invention are efficacious when administered by other routes of administration including continuous (intravenous drip) topical parenteral, intramuscular, intravenous, subcutaneous, transdermal (which may include a penetration enhancement agent), buccal, nasal and suppository administration, among other routes of administration. Oral administration can be in the form of tablets, coated tablets, dragées, hard and soft gelatine capsules, solutions, emulsions, syrups, or suspensions For the manufacture of pharmaceutical preparations, the compounds, as well as their pharmaceutically useable salts, can be formulated with a therapeutically inert, inorganic or organic excipient for the production of tablets, coated tablets, dragées, hard and soft gelatine capsules, solutions, emulsions or suspensions. The compounds of formula I can be formulated in admixture with a pharmaceutically acceptable carrier. For example, the compounds of the present invention can be administered orally as pharmacologically acceptable salts. Because the compounds of the present invention are mostly water soluble, they can be administered intravenously in physiological saline solution (e.g., buffered to a pH of about 7.2 to 7.5). Conventional buffers such as phosphates, bicarbonates or citrates can be used in the present compositions. Suitable excipients for tablets, coated tablets, dragées, and hard gelatin capsules are, for example, lactose, corn starch and derivatives thereof, talc, and stearic acid or its salts. If desired, the tablets or capsules may be enteric-coated or sustained release by standard techniques. Suitable excipients for soft gelatine capsules are, for example, vegetable oils, waxes, fats, semi-solid and liquid polyols. Suitable excipients for injection solutions are, for example, water, saline, alcohols, polyols, glycerin or vegetable oils. Suitable excipients for suppositories are, for example, natural and hardened oils, waxes, fats, semi-liquid or liquid polyols. Suitable excipients for solutions and syrups for enteral use are, for example, water, polyols, saccharose, invert sugar and glucose. The pharmaceutical preparations can also contain preservatives, solubilizers, stabilizers, wetting agents, emulsifiers, sweeteners, colorants, flavorants, salts for adjustment of the osmotic pressure, buffers, masking agents or antioxidants. The pharmaceutical preparations may also contain other therapeutically active agents known in the art.

Other suitable pharmaceutical carriers and their formulations are described in Remington: *The Science* and *Practice of pharmacy* 1995, edited by E. W. Martin, Mack Publishing Company, 19th edition, Easton, Pa. Representative pharmaceutical formulations containing a compound of the present invention are described in Examples 6-8. A skilled formulation scientist may modify the formulations within the teachings of the specification to provide numerous formulations for a particular route of administration without rendering the compositions of the present invention unstable or compromising their therapeutic activity.

In particular, the modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. That dosage can vary within wide limits and will, of course, be adjusted to the individual requirements in each particular case. For oral administration, a daily dosage of between about 0.01 and about 100 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 100 mg/kg body weight per day. A typical preparation will contain from about 5% to about 95% active compound (w/w). The daily dosage can be administered as a single dosage or in divided dosages, typically between 1 and 5 dosages per day.

In embodiments of the invention, the active compound or a salt can be administered in combination with another antiviral agent, such as a nucleoside reverse transcriptase inhibitor, another non-nucleoside reverse transcriptase inhibitor or HIV protease inhibitor. When the active compound or its derivative or salt are administered in combination with another antiviral agent the activity may be increased over the parent compound. When the treatment is combination therapy, such administration may be concurrent or sequential with respect to that of the nucleoside derivatives. "Concurrent administration" as used herein thus includes administration of the agents at the same time or at different times.

It will be understood that references herein to treatment extend to prophylaxis as well as to the treatment of existing conditions, and that the treatment of animals includes the treatment of humans as well as other animals. Furthermore, treatment of a HIV infection, as used herein, also includes treatment or prophylaxis of a disease or a condition associated with or mediated by HIV infection, or the clinical symptoms thereof.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The compounds of formula I may be prepared by various methods known in the art of organic chemistry. The starting materials for the syntheses are either readily available from commercial sources or are known or may themselves be prepared by techniques known in the art. The following examples (infra) are given to enable those skilled in the art to more clearly understand and to practice the present invention. They should not be considered as limiting the scope of the invention, but merely as being illustrative and representative thereof.

EXAMPLE 1

5-Hydroxy-1H-pyrazole-3-carboxylic acid ethyl ester

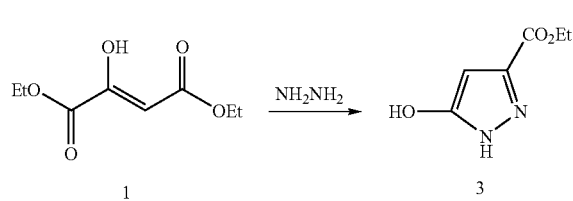

Diethyloxalacetate, sodium salt (14.53 g, 69.15 mmol) was dissolved in 100 mL of benzene and stirred for 20 min. To the solution was added 100 mL of acetic acid and the reaction mixture was stirred for a further 30 min. Hydrazine monohydrochloride (9.47 g, 138 mmol) was added and the reaction mixture was stirred for an additional 30 min. The reaction was brought to reflux at 100° C. for 24 h. The reaction was then removed from heat and cooled to room temperature and extracted with EtOAc and washed with 10% hydrochloric acid, saturated sodium bicarbonate solution, water and then brine. The solvent was removed in vacuo to yield an oily solid which was then triturated with a 2:1 mixture of diethyl ether:hexanes to yield 3 (10.00 g, 92%) as an off-white solid: LRMS (electrospray); m/z [M+H]$^+$=157.

EXAMPLE 2

5-(tert-Butyl-dimethyl-silanyloxy)-1H-pyrazole-3-carboxylic acid ethyl ester

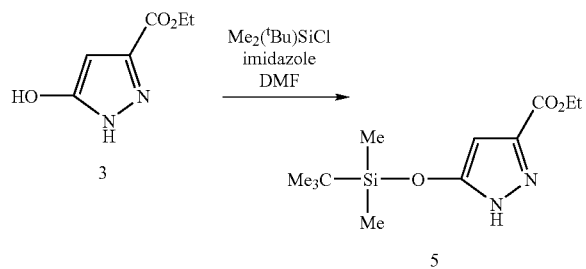

A solution of hydroxy pyrazole 3 (1.00 g, 6.40 mmol) in 10 mL of dimethylformamide was cooled to 0° C. and purged with nitrogen. 12.8 mL (12.8 mmol) of BDCS Silylation Reagent (Aldrich) was added and the reaction was stirred for 24 h at room temperature. The reaction was quenched by the addition of water and extracted with EtOAc. The combined organic layers were further washed with water and brine, dried with MgSO$_4$ and filtered. Excess solvent was removed in vacuo to yield a dark oil. The crude product was purified via silica gel chromatography with hexanes:EtOAc (9:1) to afford the desired silyl ether 5 (1.64 g, 94%): LRMS (electrospray); m/z [M+H]$^+$=271.

EXAMPLE 3

5-(tert-Butyl-dimethyl-silanyloxy)-1-(2,2,2-trifluoro-ethyl)-1H-pyrazole-3-carboxylic acid ethyl ester

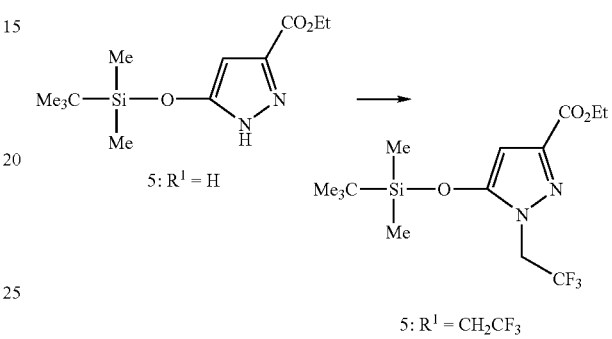

The silylenol ether 5 (R$^1$=H) (1.64 g, 6.06 mmol) was dissolved in 15 mL of dimethylformamide under nitrogen and cooled to 0° C. Sodium carbonate was then added to the reaction mixture and stirred for 15 min while purging with nitrogen. 2-Bromo-1,1,1-trifluoroethane (1.00 g, 6.06 mmol) was then added and the reaction mixture was stirred at room temperature for 24 h. The reaction was then brought to reflux for an additional 24 h. The reaction was quenched by the addition of water. The mixture was extracted with EtOAc and washed with saturated sodium bicarbonate solution, water and brine. The mixture was dried with MgSO$_4$, filtered, and the solvent removed in vacuo to yield an oil. The crude mixture was purified by silica gel column chromatography with an elution of hexanes:EtOAc (85:15) to afford 5 (R$^1$=CH$_3$; 1.84 g, 85%).

EXAMPLE 4

5-Hydroxy-1-(2,2,2-trifluoro-ethyl)-1H-pyrazole-3-carboxylic acid ethyl ester

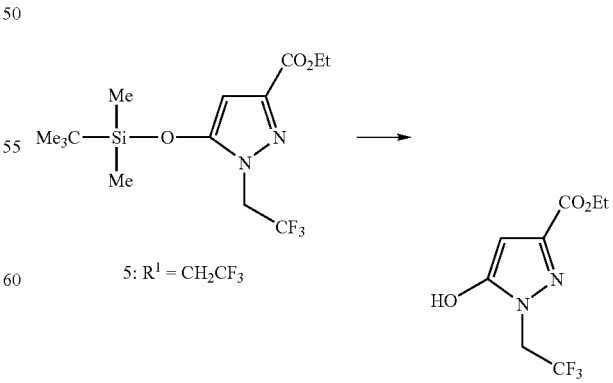

The silylenol ether 5 (1.84 g, 5.22 mmol) was dissolved in 10 mL of DCM and stirred under nitrogen. The mixture was cooled to 0° C. and stirred for an additional 15 min. Tetrabutylammonium fluoride hydrate (1.36 g, 5.22 mmol) was then added to the reaction vessel and allowed to stir for 24 h. The reaction was quenched by the addition of saturated sodium bicarbonate solution and extracted with DCM. The combined organic layers were further washed with water then brine, dried with MgSO$_4$ and filtered. The solvent was removed in vacuo to yield a pale yellow oil. The crude mixture was purified by silica gel chromatography with hexanes:EtOAc (3:1) to give the desired product 6 ($R^1$=CH$_2$CF$_3$; 1.14 g, 91%).

EXAMPLE 5

1-Ethyl-5-hydroxy-1H-pyrazole-3-carboxylic acid ethyl ester

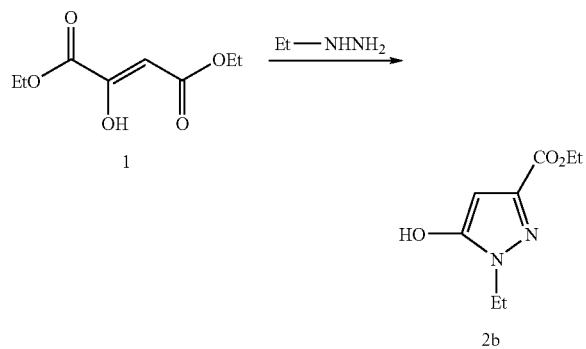

Acetic acid (100 mL) was added via a dropping funnel to a solution of diethyloxalacetate, sodium salt (12.8 g, 60.9 mmol) in 175 mL benzene at room temperature. After the addition was complete, a solution of ethyl hydrazine, oxalate salt (9.1 g, 60.9 mmol) in 40 mL of warm water was added dropwise with stirring. After being heated at reflux for 36 h, the reaction mixture was cooled to room temperature, poured into water and extracted with EtOAc. The combined organic layers were washed with brine and the solvent removed in vacuo to give crude product as a brown oily solid. This residue was then triturated with a 2:1 mixture of diethyl ether:hexanes to give 2b (7.7 g) as an off-white solid: LRMS (electrospray); m/z [M+H]$^+$=185.

EXAMPLE 6

5-Chloro-4-formyl-1-isopropyl-1H-pyrazole-3-carboxylic acid ethyl ester

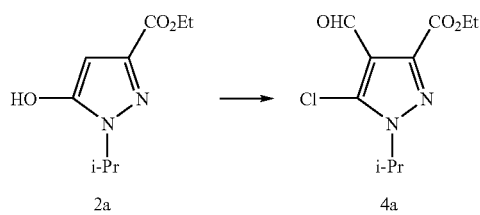

A round bottom flask containing 100 mL of 1,2-dichloroethane was cooled to 0° C. and purged with nitrogen. Dimethylformamide (14.75 g, 201 mmol) was added and allowed to stir for 5 min at 0° C. Phosphorus oxychloride (155 g, 1.0 mol) was added slowly while maintaining an internal temperature of 0° C. A solution of the hydroxy pyrazole (20.0 g, 100 mmol) dissolved in 100 mL of 1,2-dichloroethane was added slowly to the mixture of dimethylformamide and phosphorus oxychloride at 0° C. Upon the complete addition of the hydroxy pyrazole the reaction vessel was removed from the ice bath and stirred at room temperature for 30 min. Finally the reaction was heated to 110° C. for 24 h. The reaction mixture was removed from heat and brought to room temperature. Excess 1,2-dichloroethane and phosphorus oxychloride were removed in vacuo to yield a black oil. The oil was slowly dissolved in an excess of saturated sodium bicarbonate solution and stirred for an additional 6 h. The mixture was extracted with a 1:1 mixture of THF and EtOAc, and washed with water and then brine. The organic extracts were dried (MgSO$_4$) and evaporated to yield a dark oil. The product was purified by silica gel chromatography with hexanes:EtOAc (9:1) to afford the product (20.34 g, 80%;).

EXAMPLE 7

5-(3-Chloro-phenoxy)-4-formyl-1-isopropyl-1H-pyrazole-3-carboxylic acid ethyl ester

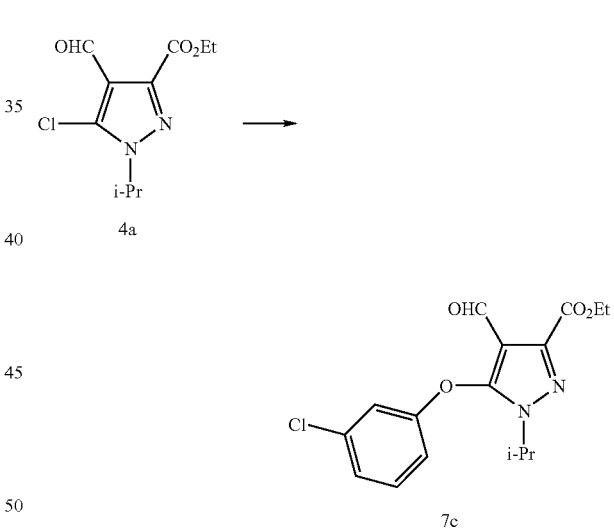

Sodium hydride (60% in mineral oil, 0.48 g, 12 mmol) was added portionwise to 3-chlorophenol (1.54 g, 12 mmol) in 40 mL of anhydrous dimethylformamide at room temperature. After the phenoxide solution stirred for 15 min, 4a (2.0 g, 8.2 mmol) was added in one portion and the reaction then heated at 110° C. under nitrogen for 1 h. The reaction mixture was then cooled to room temperature and then poured into 0.5 N sodium bisulfate solution. The crude product was extracted using a 1:1 mixture of hexanes:EtOAc and the combined organic layers washed with 0.1 N NaOH and brine, and the solvent removed in vacuo. The crude product was then purified by silica gel chromatography (10:1 then 5:1 hexanes:EtOAc) to yield 7c (2.3 g) as a white solid: LRMS (electrospray): m/z [M+H]$^+$=337.

EXAMPLE 8

5-(3,5-Dichloro-phenoxy)-4-(1-hydroxy-ethyl)-1-isopropyl-1H-pyrazole-3-carboxylic acid ethyl ester

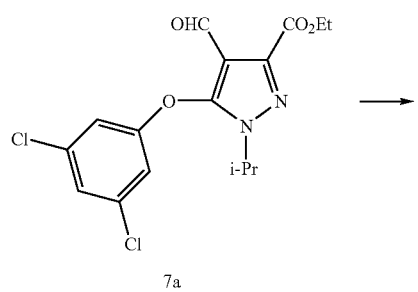

7a

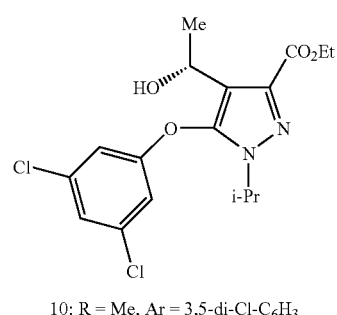

10: R = Me, Ar = 3,5-di-Cl-$C_6H_3$

Methyl magnesium bromide (3.0 M in THF, 0.9 mL, 2.7 mmol) was added slowly to a solution of the 7a in THF:diethyl ether (1:6, 30 mL) at −30° C. After the addition was complete, the reaction was stirred at 0° C. for 2 h. An additional 0.3 mL of the Grignard reagent solution was then added, stirring continued for an additional 1 h. The reaction quenched by adding saturated aqueous ammonium chloride. The product was extracted into EtOAc and the combined organic layers washed with brine. The crude product was purified by silica gel chromatography (10:1 hexanes:EtOAc) to give the title compound (0.93 g) as a colorless oil: LRMS (electrospray); m/z [M+Na]$^+$=409.

EXAMPLE 9

5-(3,5-Dichloro-phenoxy)-4-ethyl-1-isopropyl-1H-pyrazole-3-carboxylic acid ethyl ester

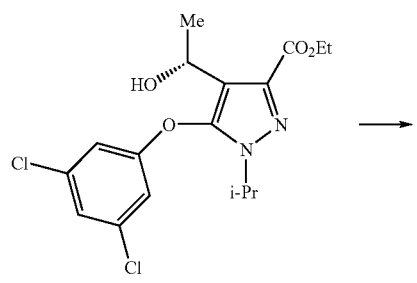

10: R = Me, Ar = 3,5-di-Cl-$C_6H_3$

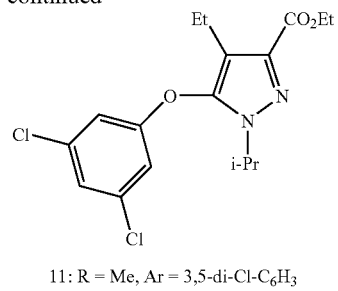

11: R = Me, Ar = 3,5-di-Cl-$C_6H_3$

To a solution of alcohol (0.61 g, 1.6 mmol) and trifluoroacetic acid (1.3 mL, 17 mmol) in 20 mL of DCM was added triethylsilane (0.28 mL, 1.7 mmol) at room temperature. After 2 h, an additional 0.28 mL triethylsilane was added and the reaction stirred overnight. A further 0.3 mL triethylsilane was then added and the reaction was complete after an additional 5 h. The solvent was removed in vacuo. The residue was taken up in EtOAc and washed with saturated sodium bicarbonate solution and brine. The crude product was purified by silica gel chromatography (20:1 hexanes:EtOAc) to give the title compound (0.55 g): LRMS (electrospray); m/z [M+H]$^+$=371.

EXAMPLE 10

[5-(3,5-Dichloro-phenoxy)-4-ethyl-1-isopropyl-1H-pyrazol-3-yl]-methanol

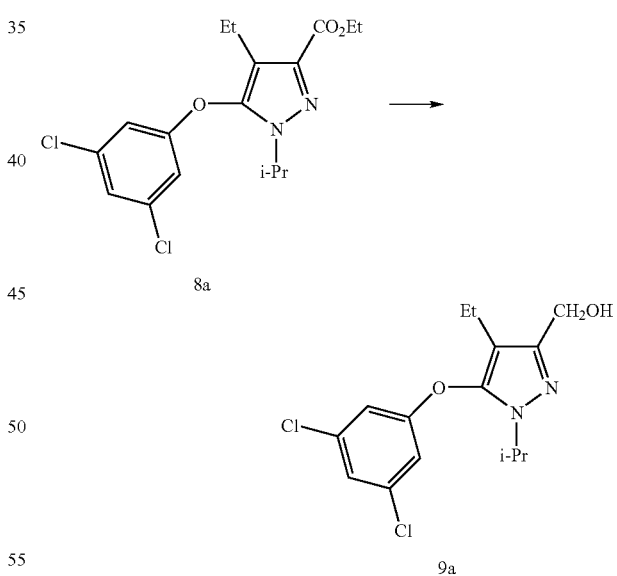

Lithium triethylborohydride (1.0 M in THF, 3.0 mL, 3.0 mmol) was added slowly to ester 8a (0.54 g, 1.5 mmol) in 10 mL of THF at −20° C. The reaction was stirred at −20° C. for 30 min, then at 0° C. for an additional 1 h. The reaction was then quenched by adding 4 mL of a 10% solution of acetic acid in EtOH. After 10 min, the solvents were removed in vacuo, the residue taken up in 1 M HCl and the product extracted into EtOAc. The combined organic layers were washed with saturated aqueous sodium bicarbonate and brine and the solvent removed in vacuo. Purification by silica gel chromatography (2:1 hexanes:EtOAc) gave 9a (0.42 g) as a white solid: LRMS (electrospray); m/z [M+H]$^+$=329.

EXAMPLE 11

3-Chloromethyl-5-(3,5-dichloro-phenoxy)-4-ethyl-1-isopropyl-1H-pyrazole

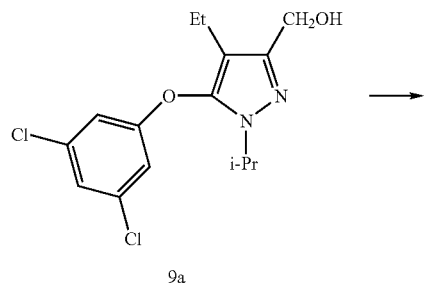

9a

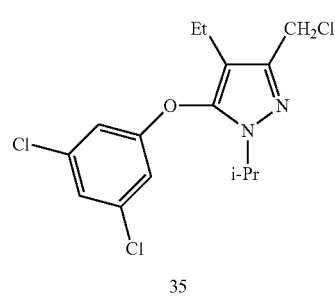

35

Thionyl chloride (0.13 mL, 1.8 mmol) was added dropwise to an ice-cold solution of 9a (0.35 g, 1.1 mmol) in 10 mL of DCM. After 1 h, the solvent was removed in vacuo, the residue treated with saturated aqueous sodium bicarbonate, and the product extracted into EtOAc. The combined organic layers were washed with brine and the solvent removed in vacuo to give 35 (0.37 g) in sufficient purity that it was not purified further: LRMS (electrospray); m/z [M+H]$^+$=347.

EXAMPLE 12

[5-(3,5-Dichloro-phenoxy)-4-ethyl-1-isopropyl-1H-pyrazol-3-yl]-acetonitrile

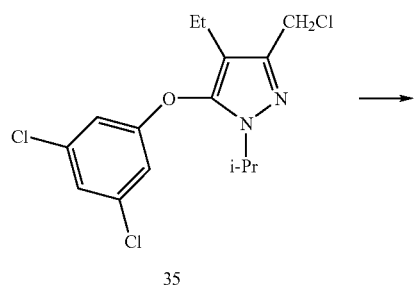

35

-continued

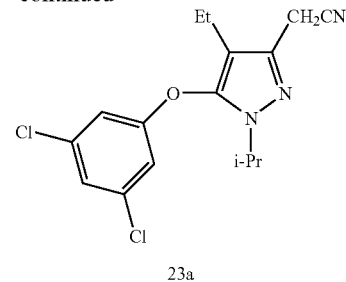

23a

A solution of 35 (0.37 g, 1.1 mmol) in 2 mL of dimethylsulfoxide was added to a stirring mixture of sodium cyanide (0.11 g, 2.2 mmol) in 10 mL of dimethylsulfoxide at room temperature. After 4 h the reaction mixture was poured into 0.1 N aqueous sodium hydroxide and the product extracted into EtOAc. The combined organic layers were diluted with an equal volume of hexanes then washed three times with water and then brine. The solvents were then removed in vacuo and purification by silica gel chromatography (8:1 then 5:1 hexanes:EtOAc) gave 23a (0.345 g): LRMS (electrospray); m/z [M+H]$^+$=338.

EXAMPLE 13

2-[5-(3,5-Dichloro-phenoxy)-4-ethyl-1-isopropyl-1H-pyrazol-3-yl]-ethylamine

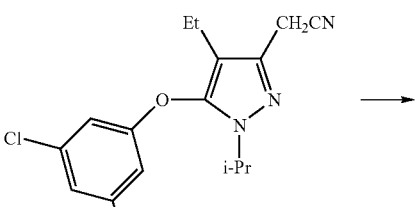

23a

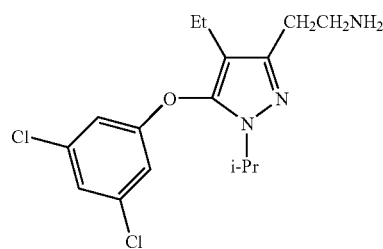

24a

Diisobutylaluminum hydride (1.5 M in toluene, 0.88 mL, 1.3 mmol) was added slowly to a solution of 23a (0.15 g, 0.44 mmol) in 5 mL of toluene at −10° C. Stirring was continued at −10° C. for 30 min, then sodium borohydride (0.10 g, 2.7 mmol) was added in one portion followed by the dropwise addition of 10 mL of MeOH. After the addition was complete, the cooling bath was removed and the reaction stirred at room temperature for 30 min. The reaction mixture was then poured into aqueous sodium potassium tartrate solution and extracted with ether. The combined ether layers were then washed with brine and dried over potassium carbonate. Purification by silica gel chromatography (95:5:0.5 DCM: MeOH: saturated aqueous ammonium hydroxide) gave 24a (0.11 g): LRMS (electrospray); m/z [M+H]$^+$=342.

EXAMPLE 14

[5-(3,5-Dichloro-phenoxy)-4-ethyl-1-isopropyl-1H-pyrazol-3-yl]-acetic acid

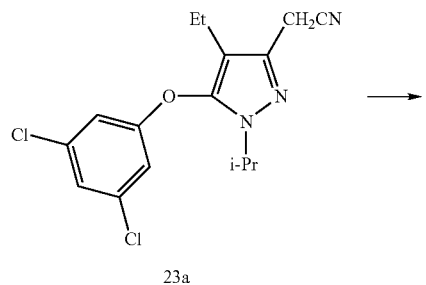

23a

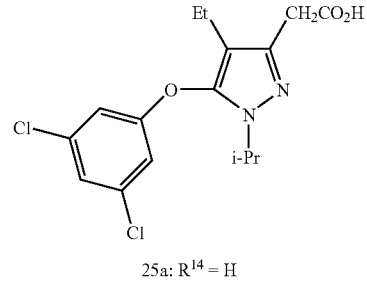

25a: R$^{14}$ = H

The nitrile 23a (0.19 g, 0.56 mmol) was heated at 100° C. for 1.5 h in a mixture of 3 mL of glacial acetic acid, 3 mL of water, and 6 mL of concentrated hydrochloric acid. The reaction mixture was poured into 50 mL of water and the product extracted into EtOAc. The combined organic layers were washed with brine and the solvent removed in vacuo to give 25a (0.19 g): LRMS (electrospray); m/z [M+H]$^+$=357.

EXAMPLE 15

[5-(3,5-Dichloro-phenoxy)-4-ethyl-1-isopropyl-1H-pyrazol-3-yl]-acetic acid methyl ester

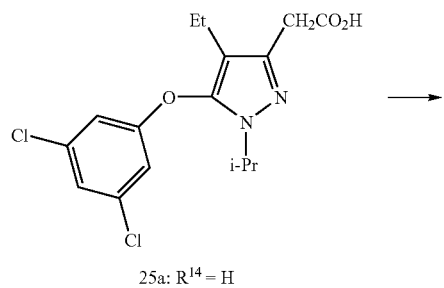

25a: R$^{14}$ = H

-continued

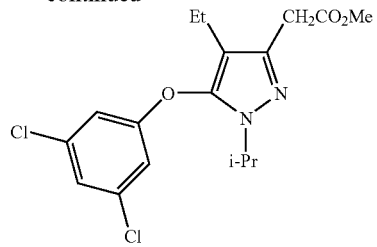

25a: R$^{14}$ = Me

A solution of 25a (R$^{14}$=H; 0.19 g, 0.53 mmol) in 10 mL of 3 M methanolic hydrogen chloride was stirred overnight at room temperature. The reaction was then concentrated in vacuo, and the residue taken up in EtOAc and washed with saturated sodium bicarbonate solution and brine. Removal of the solvent in vacuo gave 25a (R$^{14}$=Me; 0.19 g) which needed no further purification: LRMS (electrospray); m/z [M+H]$^+$=371.

EXAMPLE 16

2-[5-(3,5-Dichloro-phenoxy)-4-ethyl-1-isopropyl-1H-pyrazol-3-yl]-ethanol

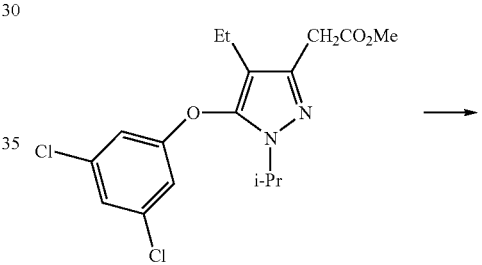

25a: R$^{14}$ = Me

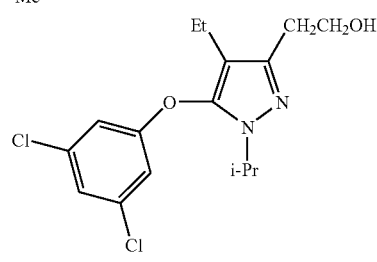

26a: R$^{13}$ = H

A solution of lithium triethylborohydride (1.0 M in THF, 1.5 mL, 1.5 mmol) was added slowly to a solution of 25a (0.19 g, 0.51 mmol) in 5 mL of THF at −20° C. Stirring was continued at −20° C. for 30 min then at 0° C. for 1 h. The reaction was then quenched by adding 5 mL of a 10% acetic acid in EtOH solution. After stirring for 30 min, the solvent was removed in vacuo and the residue taken up in 1 N HCl and the products (a mixture of aldehyde and alcohol) were extracted into EtOAc. The combined organic layers were washed with brine and the solvent removed in vacuo. The crude product mixture was then dissolved in 10 mL of MeOH and sodium borohydride (0.10 g, 2.6 mmol) was added in one portion at 0° C. Stirring was continued for 30 min then the reaction was quenched by adding 10 mL of saturated aqueous ammonium chloride. The mixture was diluted with 50 mL of water and the product extracted into EtOAc. Purification by silica gel chromatography (2:1 hexanes: EtOAc) gave 26a (0.14 g) as a colorless oil: LRMS (electrospray); m/z [M+H]$^+$=343.

EXAMPLE 17

Carbamic acid 5-(3,5-dichloro-phenoxy)-1-isopropyl-4-methyl-1H-pyrazol-3-ylmethyl ester

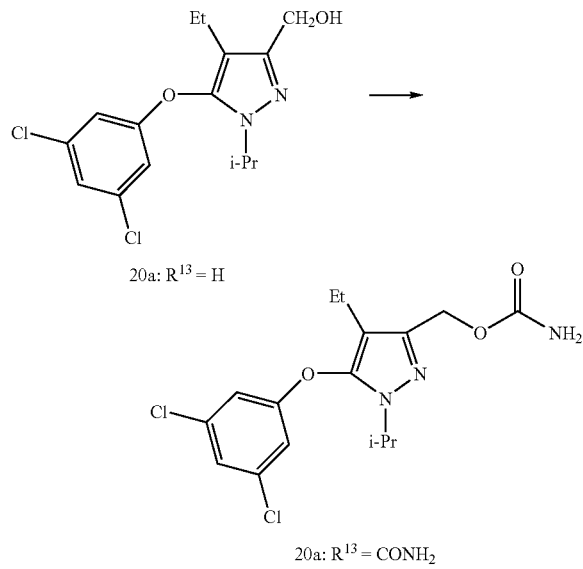

20a: R$^{13}$ = H

20a: R$^{13}$ = CONH$_2$

To a solution of 20a (R$^{13}$=H; 0.20 g, 0.64 mmol) in 5 mL of DCM at 0° C. was added trichloroacetylisocyanate (91 μL, 0.77 mmol) dropwise. After 30 min the solvent was removed in vacuo and the residue was taken up in 4 mL of MeOH and treated with 2 mL of water and 200 mg of potassium carbonate. The reaction was stirred at room temperature for 2 h. The reaction mixture was then poured into 50 mL of water and the product extracted into EtOAc. The combined organic layers were washed with brine and the solvent removed in vacuo. Purification by silica gel chromatography (2:1 hexanes:EtOAc) followed by recrystallization from DCM/hexanes gave 20a (R$^{13}$=CONH$_2$; 0.21 g) as a white solid: LRMS (electrospray); m/z [M+H]$^+$=358.

EXAMPLE 18

5-(3-Chloro-phenoxy)-4-hydroxymethyl-1-isopropyl-1H-pyrazole-3-carboxylic acid ethyl ester

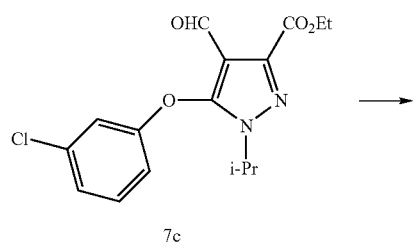

7c

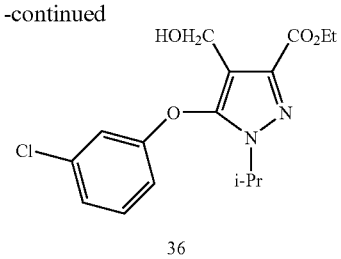

36

Sodium borohydride (80 mg, 2.1 mmol) was added in one portion to a solution of 7c (0.72 g, 2.1 mmol) in 20 mL of MeOH at 0° C. After stirring for 30 min, the reaction was quenched by adding 4 mL of saturated aqueous ammonium chloride and then the bulk of the solvents were removed in vacuo. The residue was taken up in water and the product extracted into EtOAc. The combined organic layers were washed with water and brine and the solvents removed in vacuo. Purification by silica gel chromatography (6:1 then 4:1 hexanes:EtOAc) gave the title compound 36 (0.64 g) as a colorless oil: LRMS (electrospray); m/z [M+Na]$^+$=361.

EXAMPLE 19

5-(3-Chloro-phenoxy)-4-iodomethyl-1-isopropyl-1H-pyrazole-3-carboxylic acid ethyl ester

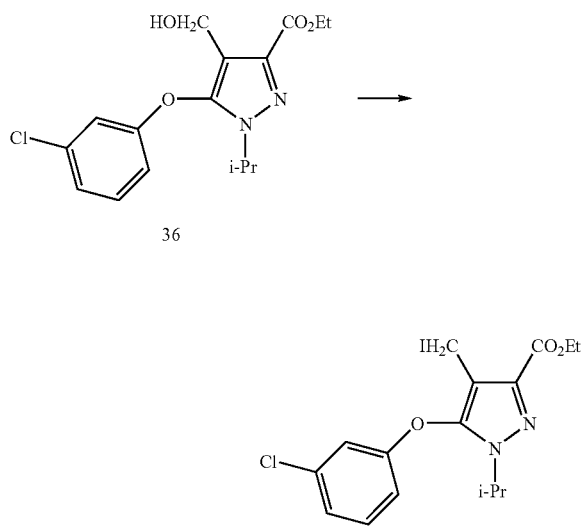

36

37

A solution of diphosphorus tetraiodide (0.62 g, 1.1 mmol) and 40 mL of toluene was heated in the dark at 85° C. for 10 min. A solution of 36 (0.62 g, 1.8 mmol) in 4 mL of toluene was then added in one portion and the mixture stirred for 10 min. The reaction was then quenched by adding 40 mL of 10% aqueous sodium bisulfite solution and the mixture stirred until it became colorless. The layers were then separated and the organic layer was washed with water and brine, dried over magnesium sulfate, and concentrated in vacuo. This crude product 37 was taken directly on to the next step.

EXAMPLE 20

5-(3-Chloro-phenoxy)-1-isopropyl-4-methyl-1H-pyrazol-3-yl]-methanol

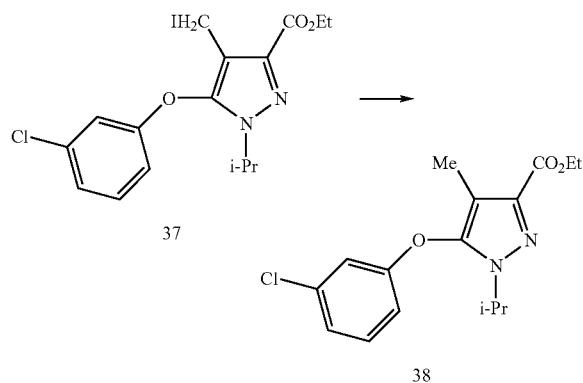

A solution of lithium triethylborohydride (1.0 M in THF, 5.4 mL, 5.4 mmol) was slowly added to the crude iodide 37 (1.8 mmol) in 10 mL of THF at −20° C. After 30 min, the reaction was warmed to 0° C. and stirred for 1 h. An additional 2.7 mL of lithium triethylborohydride solution was added and the reaction stirred for 30 min more. The reaction was then quenched by adding 5 mL of 10% acetic acid in EtOH and the reaction was concentrated in vacuo. The resulting residue was taken up in 1 N HCl and the product extracted into EtOAc. The combined organic layers were washed with saturated aqueous sodium bicarbonate and brine and the solvent was removed in vacuo. Purification by silica gel chromatography (2:1 hexanes:EtOAc) gave 38 (0.46 g) as a colorless oil: LRMS (electrospray); m/z [M+H]$^+$=281.

EXAMPLE 21

6-[5-(3-Chloro-phenoxy)-1-isopropyl-4-methyl-1H-pyrazol-3-ylmethyl]-2H-pyridazin-3-one

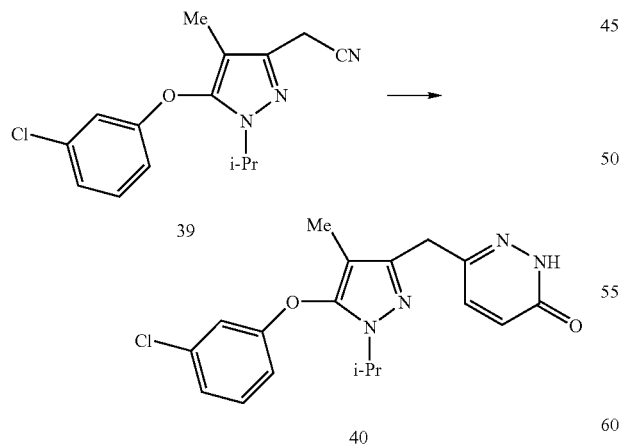

Sodium hydride (60% dispersion in mineral oil, 0.14 g, 3.5 mmol) was added in one portion to a solution of 39 (0.40 g, 1.4 mmol) and 3,6-dichloropyridazine (0.42 g, 2.8 mmol) in 10 mL of DMF at room temperature. The reaction was stirred for 1 h, then poured with vigorous stirring into 100 mL of 0.5 N aqueous sodium bisulfate. The resulting red oily solid was collected by filtration and washed with water. This solid was then dissolved into EtOAc and washed with brine and the solvent removed in vacuo. The residue was then taken up in a mixture of 4 mL of acetic acid, 8 mL of 12 N HCl and 4 mL of water and heated under argon at 100° C. for 1 h. The reaction mixture was then cooled and carefully added to aqueous potassium carbonate and the product extracted into EtOAc. Purification by preparative thin layer chromatography (95:5 DCM:MeOH) gave 40 (0.35 g) as a white solid: LRMS (electrospray); m/z [M+H]$^+$=359.

EXAMPLE 22

2-[5-(3-Chloro-phenoxy)-4-ethyl-1-isopropyl-1H-pyrazol-3-ylmethyl]-isoindole-1,3-dione

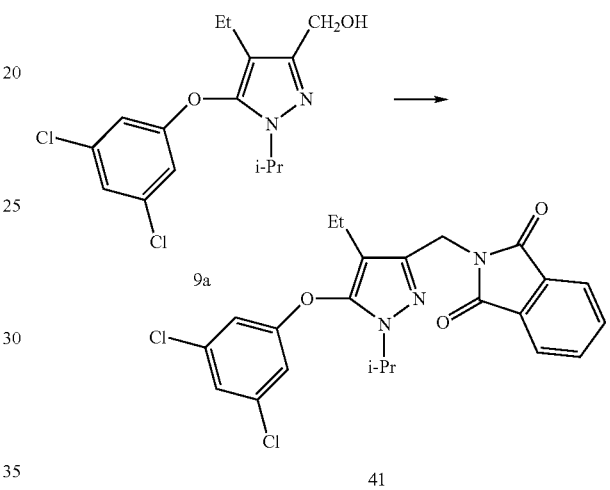

To a mixture of 9a (220 mg, 0.746 mmol), triphenylphosphine (391 mg, 1.49 mmol) and phthalimide (220 mg, 1.49 mmol) in THF (20 mL), was added diethyl azodicarboxylate (260 mg, 1.492 mmol) dropwise at room temperature under nitrogen. The resulting yellow solution was stirred under nitrogen at room temperature for 24 h. Methanol (3 mL) was added and all solvents were removed in vacuo. The residue was purified on silica gel with hexane:EtOAc (4:1) to give a white solid 41 (310mg, 98%): LRMS (electrospray); m/z [M+H]$^+$=424.

EXAMPLE 23

2-[5-(3-Chloro-phenoxy)-4-ethyl-1-isopropyl-1H-pyrazol-3-yl]-methylamine

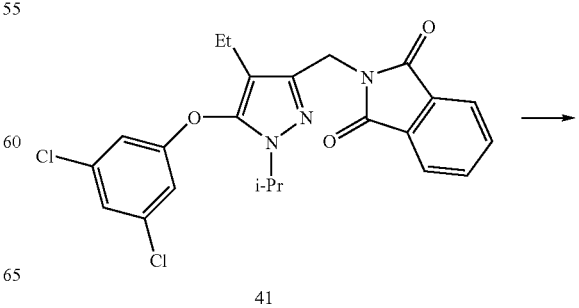

-continued

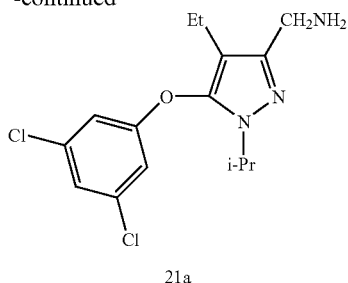

21a

To a solution of 32 (310 mg, 0.731 mmol) in MeOH (10 mL) and THF (10 mL), was added anhydrous hydrazine (243 mg, 0.24 mL, 7.31 mmol) at room temperature. The reaction mixture was heated at reflux under nitrogen for 2 h. The reaction was cooled to room temperature and a 10% NaOH solution (30 mL) was added to the reaction mixture. The crude product was extracted with DCM (4×25 mL). The solvents were removed in vacuo. The residue was purified on silica gel with EtOAc:MeOH (4:1) to give a pale yellow oil 21a (182 mg, 85%): LRMS (electrospray); m/z [M+H]$^+$= 294.

EXAMPLE 24

N-[5-(3,5-Dichloro-phenoxy)-4-ethyl-1-isopropyl-1H-pyrazol-3-ylmethyl]-formamide

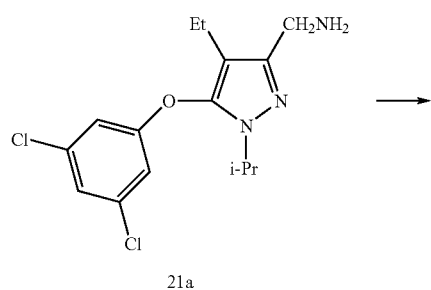

21a

→

Et, CH₂—N—H, O, H

22a: R$^{13}$ = COH

A solution of amine 21a (71 mg, 0.21 mmol) in ethyl formate (6 mL) was heated at reflux for 5 h. The solvent was then removed in vacuo. The residue was purified by silica gel chromatography with hexane/EtOAc (2:1) to give a white solid 22a (R$^{13}$=COH; 73 mg, yield 95%): LRMS (electrospray); m/z [M+H]$^+$=356.

EXAMPLE 25

N-[5-(3,5-Dichloro-phenoxy)-4-ethyl-1-isopropyl-1H-pyrazol-3-ylmethyl]acetamide

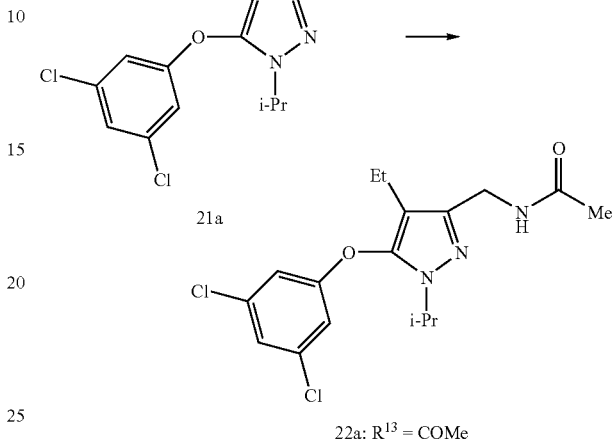

22a: R$^{13}$ = COMe

A solution of the amine 21a (71 mg, 0.22 mmol) in acetic anhydride (5 mL) was stirred at room temperature for 2.5 h. Methanol (10 mL) was added to the reaction mixture and the solvents were removed in vacuo. The residue was treated with 10% NaHCO₃ (20 mL) and stirred for 20 min. The crude product was extracted with DCM (3×20 mL). The organic phase was collected and washed with brine. The solvent was removed in vacuo. The residue was purified by silica gel chromatography with hexane:EtOAc (2:1) to give a white solid 22a (R$^{13}$=COMe; 70 mg, yield 87.5%): LRMS (electrospray); m/z [M+H]$^+$=370.

EXAMPLE 26

N-[5-(3,5-Dichloro-phenoxy)-4-ethyl-1-isopropyl-1H-pyrazol-3-ylmethyl]-methanesulfonamide

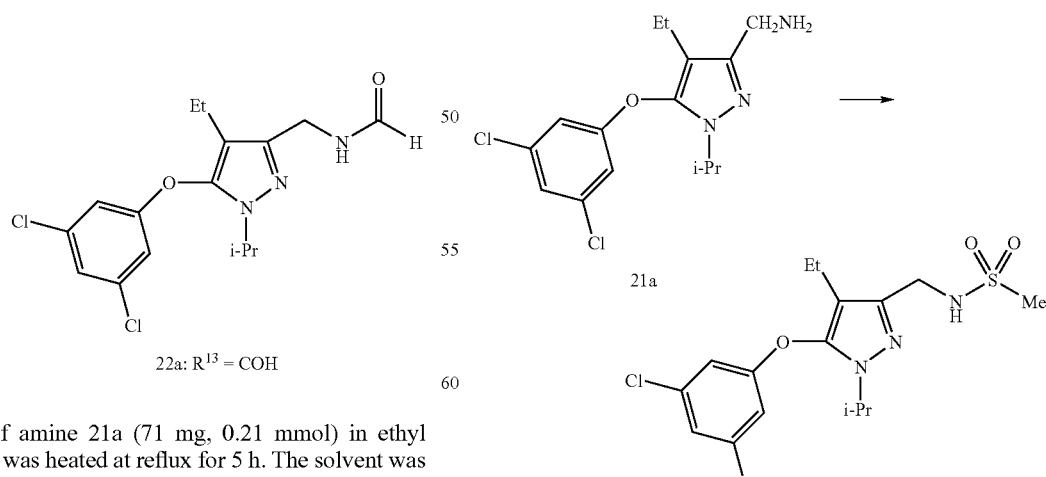

22a: R$^{13}$ = SO₂Me

To a solution of the 21a (83 mg, 0.25 mmol) and triethylamine (76 mg, 0.75 mmol) in anhydrous DCM (5 mL), was added methanesulfonyl chloride (41 mg, 0.35 mmol). The resulting yellow slurry was stirred under nitrogen at room temperature for 20 h. Water (10 mL) was added to the reaction. The crude product was extracted with DCM (3×10 mL). The organic layers were collected and washed with brine. The solvent was removed in vacuo. The residue was purified on silica gel with hexane:EtOAc (3:1) to give a white solid 22a ($R^{13}=SO_2Me$; 98 mg, yield 96.5%): LRMS (electrospray); m/z $[M+H]^+=406$.

EXAMPLE 27

[5-(3,5-Dichloro-phenoxy)-4-ethyl-1-isopropyl-1H-pyrazol-3-ylmethyl]-urea

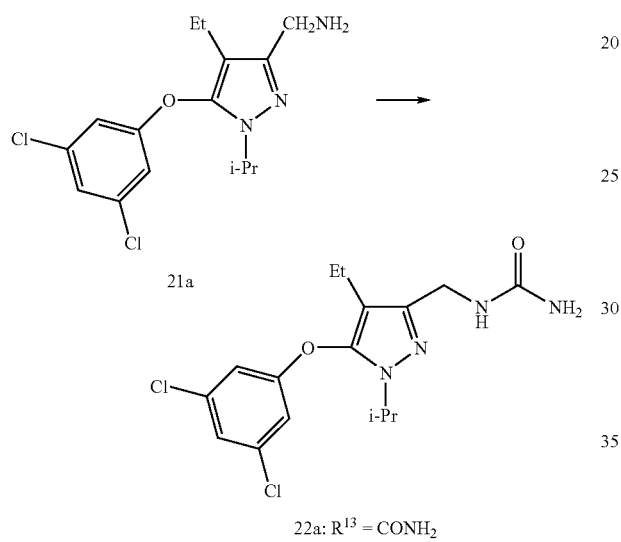

22a: $R^{13}$ = CONH$_2$

To a solution of the 21a (85 mg, 0.26 mmol) in THF (5 mL), was added trimethylsilyl isocyanate (53 mg, 0.39 mmol) in one portion. The reaction mixture was stirred at room temperature under nitrogen for 10 h. The reaction was diluted with MeOH (10 mL). All solvents were then removed in vacuo. The residue was purified on silica gel with hexane:EtOAc (2:1) to give a white solid 22a ($R^{13}$=CONH$_2$; 80mg, 83%): LRMS (electrospray); m/z $[M+H]^+=371$.

EXAMPLE 28

[5-(3-Chloro-phenoxy)-3-hydroxymethyl-1-isopropyl-1H-pyrazol-4-yl]-methanol

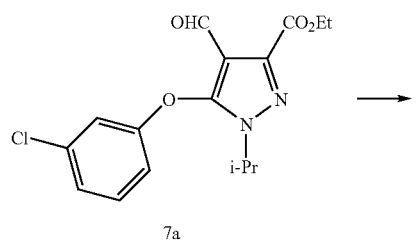

7a

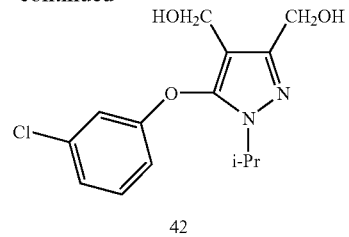

42

To a solution of the 7a (110 mg, 0.327 mmol) in THF (10 mL) cooled to −78° C., was added a solution of lithium aluminum hydride (1.0 M in THF, 0.72 mL, 0.72 mmol). The reaction was stirred under nitrogen at −78° C. for 30 min and then stirred at 0° C. for another 45 min. Methanol (0.5 mL) was added to quench the reaction. The resulting reaction mixture was stirred with a saturated sodium potassium tartrate solution (15 mL) for 2 h. The crude product was extracted with diethyl ether (4×25 mL) and the organic layers were collected and washed with brine. The solvents were removed in vacuo. The residue was purified on silica gel with hexane:EtOAc (1:2) to give 42 (95 mg, yield 97.8%): LRMS (electrospray); m/z $[M+H]^+=297$.

EXAMPLE 29

5-(3,5-Dichloro-phenoxy)-1-isopropyl-4-(2-methoxycarbonyl-vinyl)-1H-pyrazole-3-carboxylic acid ethyl ester

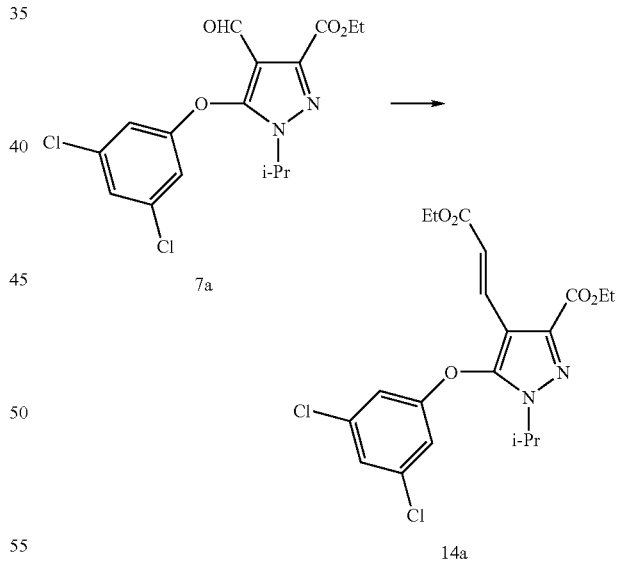

To a solution of the 7a (200 mg, 0.54 mmol) in THF (10 mL) at 0° C., was added methyl(triphenylphosphoranylidene)acetate (1.30 g, 3.89 mmol). The reaction was stirred under nitrogen at room temperature for 7 h. Water (40 mL) was added to the reaction mixture. The crude product was extracted with EtOAc (3×35 mL). The organic layers were collected and washed with brine. The solvents were removed in vacuo. The residue was purified on silica gel with hexane:EtOAc (4:1) to give the 14a (220 mg, yield 95%): LRMS (electrospray); m/z $[M+H]^+=427$.

EXAMPLE 30

5-(3,5-Dichloro-phenoxy)-1-isopropyl-4-(2-methoxycarbonyl-ethyl)-1H-pyrazole-3-carboxylic acid ethyl ester

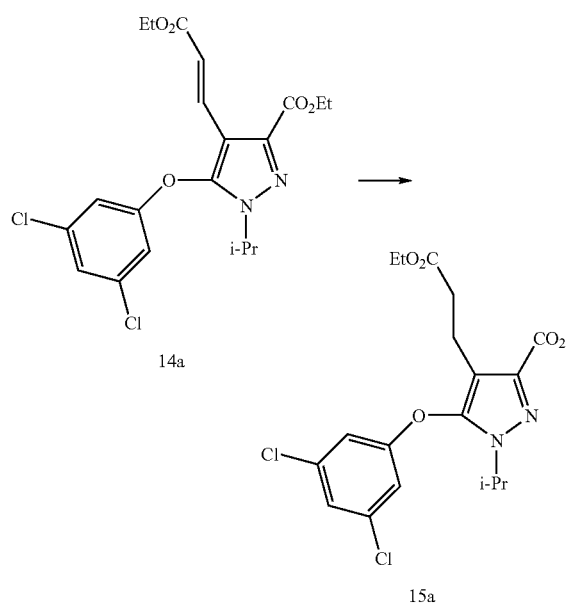

To a mixture of pre-dried magnesium turnings (50 mg, 2.10 mmol) and anhydrous MeOH (30 mL) at 0° C., was added a solution of 14 (180 mg, 0.42 mmol) in MeOH (2 mL). Gas evolution was observed. The resulting reaction mixture was stirred at 0° C. for 5 h and then at room temperature for 10 h. The reaction mixture was filtered through CELITE®. The filtrate was collected and treated with 10% sodium bisulfate solution. The crude product was extracted with EtOAc (3×25 mL). The organic layers were collected and washed with brine. The solvent was removed in vacuo. The residue was purified on silica gel with hexane:EtOAc (4:1) to give the product 15a as a colorless oil (157 mg, yield 90%): LRMS (electrospray); m/z [M+H]$^+$= 429.

EXAMPLE 31

3-[5-(3,5-Dichloro-phenoxy)-3-hydroxymethyl-1-isopropyl-1H-pyrazol-4-yl]-propan-1-ol

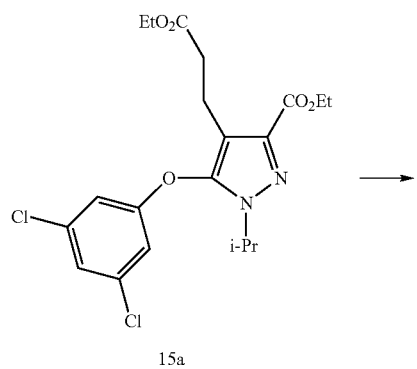

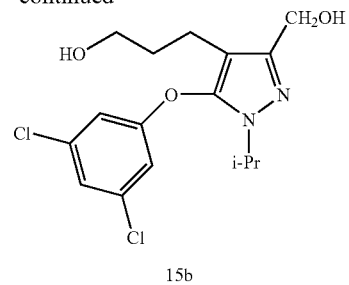

To a solution of the 15a (100 mg, 0.24 mmol) in THF (15 mL) at −40° C., was slowly added a solution of lithium triethylborohydride (1.0 M in THF, 1.25 mL, 1.25 mmol). The reaction solution was stirred under nitrogen at −40° C. for 10 minutes and then stirred at 0° C. for another 45 min. The reaction mixture was warmed up to room temperature and then stirred with 1 N HCl (20 ML) for 30 min. The crude product was extracted with diethyl ether (3×25 mL). The organic layers were collected and washed with brine. The solvents were removed in vacuo. The residue was purified on silica gel with hexane:EtOAc (1:1) to give the product 15b (52 mg, yield 60%): LRMS (electrospray); m/z [M+H]$^+$=359.

EXAMPLE 32

3-(2,4-Diethyl-5-hydroxymethyl-2H-pyrazol-3-yloxy)-benzonitrile

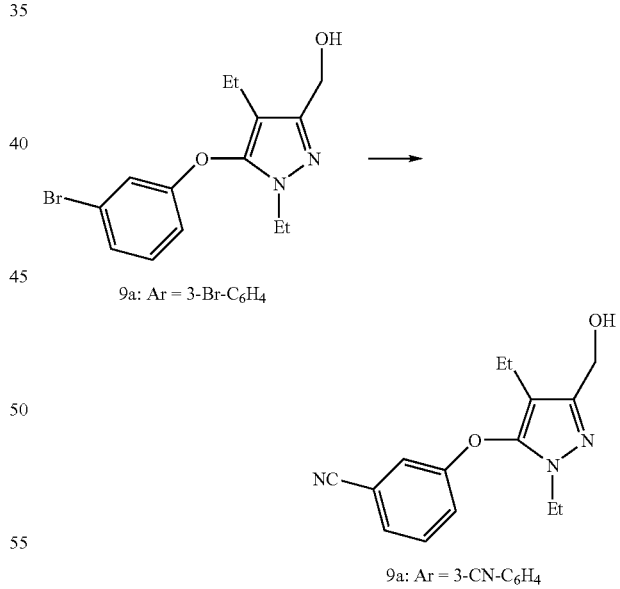

To a solution aryl bromide (96 mg, 0.30 mmol) in dimethylformamide (8 mL), was added tetrakis(triphenylphosphine)palladium(0) (173 mg, 0.15 mmol) and zinc cyanide (32 mg, 0.27 mmol) at room temperature. The resulting mixture was heated at 90° C. under argon for 6 h. The reaction mixture was poured into saturated sodium bicarbonate (50 mL) and the crude product was extracted into EtOAc (3×30 mL). The organic layers were collected and washed with brine. The solvents were removed in vacuo.

The residue was purified on silica gel with hexane:EtOAc (1:1) to give the title compound (50 mg, 61.5%): LRMS (electrospray); m/z [M+H]⁺=272.

EXAMPLE 33

5-(3,5-Dichloro-phenoxy)-4-hydroxymethyl-1-isopropyl-1H-pyrazole-3-carboxylic acid ethyl ester

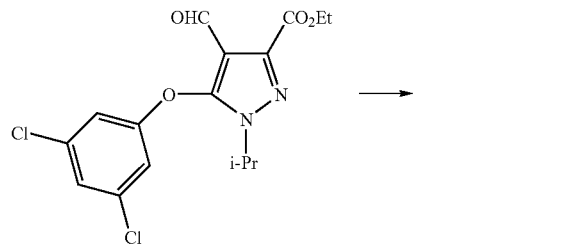

7a

42

To a solution of 7a (559 mg, 1.51 mmol) in THF (5 mL) and MeOH (15 mL) at 0° C., was added sodium borohydride (58 mg, 1.52 mmol) in one portion. The reaction mixture was stirred under nitrogen at 0° C. for 30 min. Saturated ammonium chloride solution (25 mL) was added to quench the reaction. The organic phase was collected. The aqueous phase was extracted with EtOAc (3×20 mL). All organic extracts were combined, washed with brine and concentrated in vacuo. The residue was purified on silica gel with hexane:EtOAc (4:1) to give the alcohol 42 (494 mg, yield 87%): LRMS (electrospray); m/z [M+H]⁺=373.

EXAMPLE 34

5-(3,5-Dichloro-phenoxy)-1-isopropyl-4-methoxymethyl-1H-pyrazole-3-carboxylic acid ethyl ester

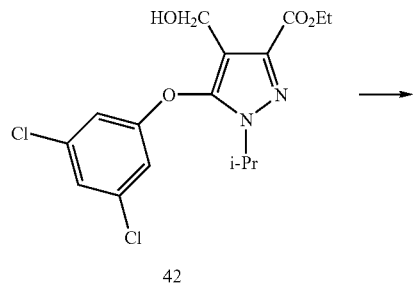

42

-continued

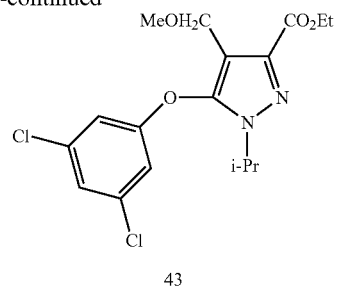

43

To a solution of 42 (87 mg, 0.233 mmol) in anhydrous dimethylformamide (5 mL) at 0° C., was added sodium hydride (60% dispersion in mineral oil, 12 mg, 0.280 mmol). The reaction mixture was stirred under nitrogen at 0° C. for 30 min. Methyl iodide (50 mg, 0.35 mmol) was added to the reaction solution at 0° C. The resulting reaction mixture was stirred under nitrogen at room temperature for 2 h. 10% sodium bisulfate solution (10 mL) was added to quench the reaction. The crude product was extracted with EtOAc (3×10 mL). The organic layers were collected, washed with brine and the solvent was removed in vacuo. The residue was purified on silica gel with hexane:EtOAc (6:1) to give 43 (50 mg, yield 56%): LRMS (electrospray); m/z [M+H]⁺= 387.

EXAMPLE 35

[5-(3,5-Dichloro-phenoxy)-1-isopropyl-4-methoxymethyl-1H-pyrazol-3-yl]-methanol

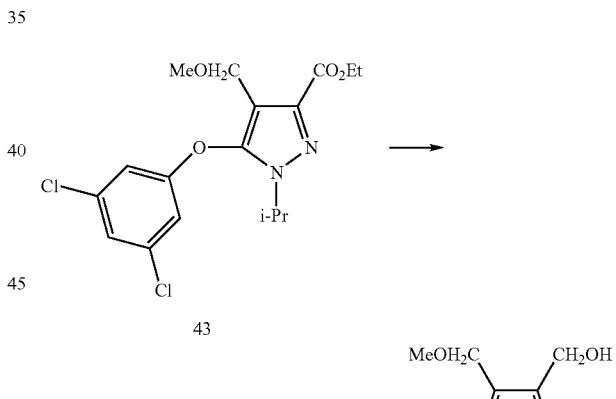

43

44

To a solution of 43 (47 mg, 0.12 mmol) in THF (15 mL) at −40° C., was slowly added lithium triethylborohydride (1.0 M in THF, 0.25 mL, 0.25 mmol). The reaction solution was stirred under nitrogen at −40° C. for 10 min and then stirred at 0° C. for 45 min. The reaction mixture was warmed up to room temperature and was then treated with 1 N hydrochloric acid (20 mL) for 30 minutes. The crude product was extracted with diethyl ether (3×25 mL). The organic layers were collected, washed with brine and the solvents were removed in vacuo. The residue was purified on silica gel with hexane:EtOAc (1:1) to 44 (26 mg, yield 63%): LRMS (electrospray); m/z [M+H]⁺=345.

EXAMPLE 36

5-[5-(3,5-Dichloro-phenoxy)-4-ethyl-1-isopropyl-1H-pyrazol-3-ylmethyl]-2H-tetrazole

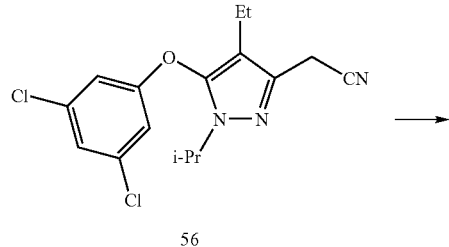

56

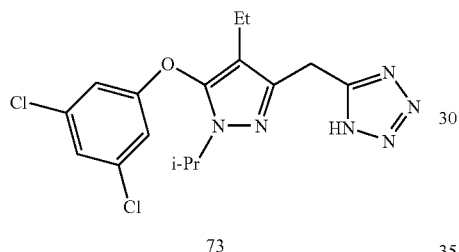

73

To a solution of nitrile (56; 0.065 g, 0.192 mmol) in 3 mL of xylenes was added azidotributyltin (0.058 mL, 0.221 mmol) and the reaction mixture heated at 130° C. for 12 h. The reaction mixture was then concentrated in vacuo and the resulting residue partitioned between EtOAc and aqueous ammonium chloride. The organic layer was dried over magnesium sulfate, filtered and then concentrated in vacuo. The crude product was purified by flash chromatography on silica gel (1:1 hexane:EtOAc then 9:1 EtOAc:MeOH) to yield the desired product (73; 3.4 mg, 5%): LRMS (electrospray) m/z (MH)=381.

EXAMPLE 37

1-[5-(3,5-Dichloro-phenoxy)-4-ethyl-1-isopropyl-1H-pyrazol-3-yl]-propan-2-on

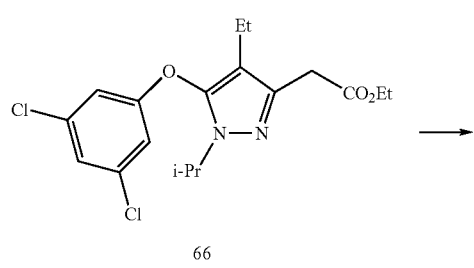

66

-continued

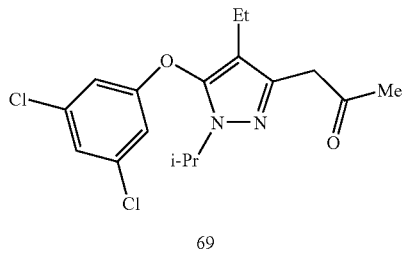

69

To a solution of the ester (66; 0.054 g, 0.140 mmol) in 5 mL of THF at 0° C. under an argon atmosphere was added methylmagnesium bromide solution (1 M in diethyl ether, 1.26 mL, 1.26 mmol). The reaction was allowed to warm to room temperature and then stirred overnight. The reaction was quenched by the dropwise addition of water followed by acidification with 1 N aqueous hydrochloric acid. The product was extracted into EtOAc, dried over magnesium sulfate, and the solvents removed in vacuo. Purification by flash chromatography silica gel (3:1 hexane:EtOAc) gave the product as an oil (8 mg, 16%): LRMS (electrospray) m/z (MH)=355.

EXAMPLE 38

1-[5-(3,5-Dichloro-phenoxy)-4-ethyl-1-isopropyl-1H-pyrazol-3-yl]-propan-2-ol

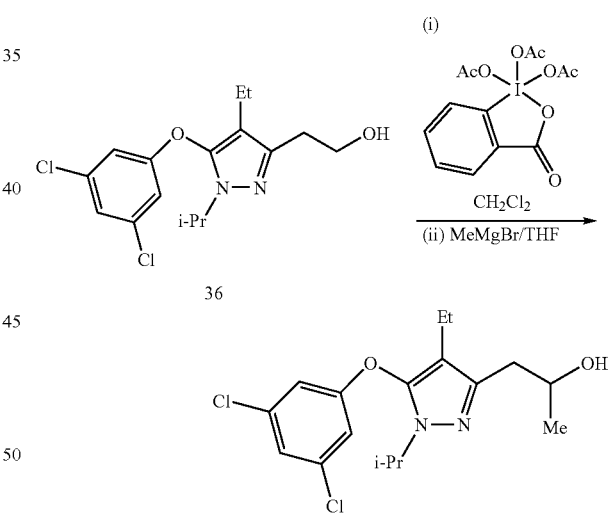

To a solution of alcohol (36; 0.080 g, 0.233 mmol) in 7 mL of DCM was added dropwise a solution of the Dess-Martin periodinane (1,1,1-triacetoxy-1,1-dihydro-1,2-benziodoxol-3(1H)-one; 0.09 g, 0.233 mmol) in 0.7 mL of DCM. After 30 min, a solution of water (0.005 mL, 0.256 mmol) in 5 mL in DCM was added and the reaction was allowed to stir overnight at room temperature. The reaction was partitioned between DCM and 10% aqueous sodium bisulfite/sodium carbonate. The organic layer was dried over magnesium sulfate and concentrated in vacuo. The crude aldehyde product was dissolved in THF, cooled to −24° C., and then methylmagnesium bromide (1 M in THF, 0.26 mL, 0.26 mmol) was added dropwise. After stirring for 72 h, the reaction was quenched by the dropwise addition of water and the resulting mixture was concentrated in vacuo. The residue was partitioned between EtOAc and water and the organic layer was dried over magnesium sulfate. Purification by flash chromatography on silica gel (7:3 hexane:EtOAc) gave the secondary alcohol 81 as an oil (11.4 mg, 14%).

EXAMPLE 39

2-[5-(3,5-Dichloro-phenoxy)-1,4-diethyl-1H-pyrazol-3-yl]-N-phenyl-acetamide

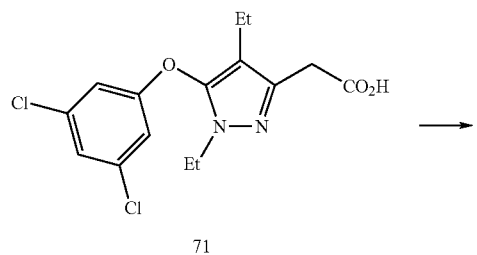

71

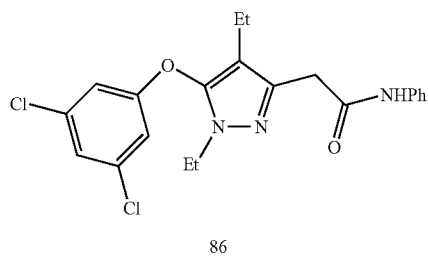

86

To a solution of the carboxylic acid (71; 0.15 g, 0.44 mmol) in 5 mL of THF was added 1,1'-carbonyldiimidazole (0.70 g, 0.44 mmol) and this mixture was heated at 50° C. for 30 min. Aniline (0.040 mL, 0.44 mmol) was added and the reaction mixture was maintained at 50° C. for an additional 3 h and then was stirred at room temperature overnight. The reaction mixture was then poured into 30 mL of EtOAc and this solution was washed with 1 N hydrochloric acid, saturated sodium bicarbonate, and brine. The solvent was then removed in vacuo and crude product was purified by preparative thin layer chromatography on silica gel (4:1 hexane:EtOAc) to yield the amide 86 as a white solid (0.174 g, 95%): mp 112.2-115.9° C.; LRMS (electrospray) m/z (MH)=418.

EXAMPLE 40

5-(3,5-Dichloro-phenoxy)-1,3,4-triethyl-1H-pyrazole

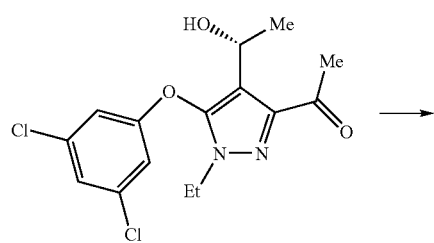

-continued

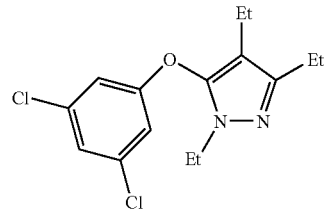

89

A solution of keto alcohol (0.16 g, 0.52 mmol) in 0.5 mL of triethylsilane and 0.5 mL of trifluoroacetice acid was stirred at 35° C. overnight. The reaction was concentrated in vacuo and the resulting crude product purified by preparative thin layer chromatography on silica gel (10:1 hexane:EtOAc) to yield the 89 as an oil (94 mg, 64%): LRMS (electrospray) m/z (MH$^+$)=313.

EXAMPLE 41

5-(3,5-Dichloro-phenoxy)-4-ethyl-1-isopropyl-3-pyrazol-1-ylmethyl-1H-pyrazole

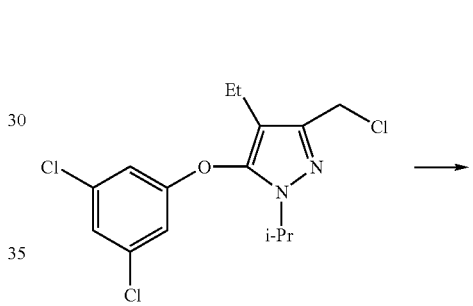

35

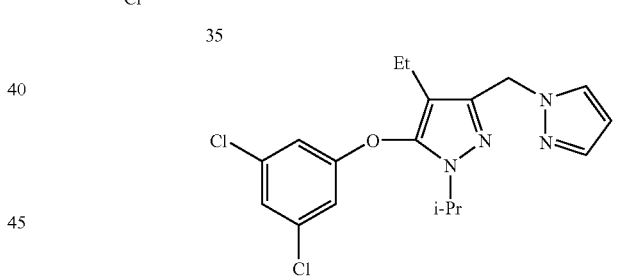

68

A 10 mL single neck round bottom was purged with nitrogen. The chloromethyl pyrazole (0.100 g, 0.288 mmol) was added to the reaction vessel and dissolved in 1 mL of dimethylformamide. Potassium carbonate and pyrazole (0.029 g, 0.431 mmol) were then sequentially added to the reaction vessel. The reaction was stirred for 24 h and then partitioned between water and EtOAc. The combined organic extracts were washed with water and brine, dried over sodium sulfate, and filtered. The solution was concentrated in vacuo to yield the crude product, which was purified by flash chromatography on silica gel (85:15 hexanes:EtOAc) to yield the desired product (68; 90%): LRMS m/z(M+)=379.

The corresponding imidazole derivative 67 was prepared by an analogous procedure substituting imidazole for pyrazole in Example 41. The desired product was isolated in 83% yield: LRMS m/z(M$^+$)=379.

EXAMPLE 42

3-[5-(3,5-Dichloro-phenoxy)-4-ethyl-1-isopropyl-1H-pyrazol-3-ylmethyl]-1H-pyrimidine-2,4-dione

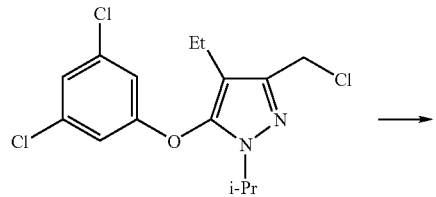

35

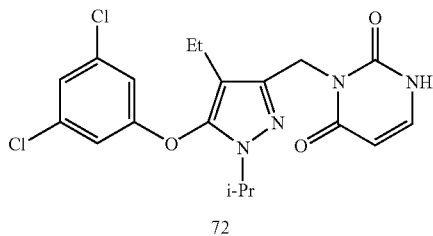

72

A 10 mL single neck round bottom flask was purged with nitrogen. The chloromethyl pyrazole (0.100 g, 0.288 mmol) was added to the reaction vessel and dissolved in 1 mL of dimethylformamide. Potassium carbonate was then added to the reaction vessel followed by uracil (0.050 g, 0.43 mmol). The reaction was stirred for 24 h and then partitioned between water and EtOAc. The combined organic extracts were washed with water and brine, dried over sodium sulfate, and filtered. The solution was concentrated in vacuo and the crude product, was purified by flash chromatography on silica gel (9:1 hexanes:EtOAc) to yield 72 in 85% yield: LRMS m/z(M$^+$)=423.

EXAMPLE 43

5-(3,5-Dichloro-phenoxy)-4-ethyl-1-isopropyl-1H-pyrazol-3-yl]-thiophen-2-yl-methanol

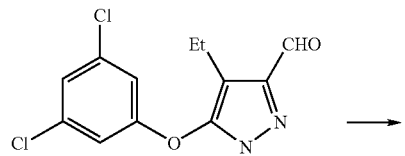

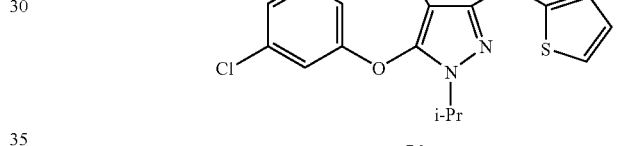

91

A 100 mL three-neck round bottom was purged with nitrogen. The flask was charged with magnesium flakes (0.074 g, 3.067 mmol) and heated and purged under nitrogen. Tetrahydrofuran (5 mL) and 2-iodothiophene (0.500 g, 2.384 mmol) were then added to the reaction vessel and heated. When the magnesium was consumed an aliquot of (0.61 ml, 0.611 mmol) was added to THF solution of aldehyde (0.200 g, 0.611 mmol) at 0° C. The reaction was allowed to warm to room temperature then cooled to 0° C. The reaction was quenched upon the addition of saturated ammonium chloride and partitioned between water and EtOAc. The combined EtOAc extracts were washed with ammonium chloride and saturated brine. The EtOAc solution was dried over sodium sulfate and filtered. The solution was concentrated in vacuo and the crude product purified by flash chroamatography on silica gel chromatography (80:20 hexanes:EtOAc) to afford 91 in 75% yield: LRMS M$^+$=411.

EXAMPLE 44

5-(3,5-Dichloro-phenoxy)-4-ethyl-1-isopropyl-3-thiophen-2-ylmethyl-1H-pyrazole

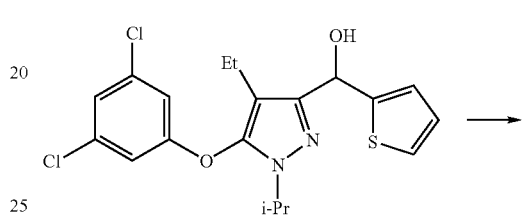

91

76

A solution of hydroxymethyl thiophene 91 (0.00 g, 2.431 mmol) and 3 mL of trifluoroacetic acid was cooled to 0° C. Triethylsilane (0.58 ml, 3.65 mmol) was added and the reaction stirred at 0° C. under a nitrogen atmosphere. The reaction was allowed to warm to room temperature and stirred for an additional 24 h. The reaction was cooled to 0° C. and quenched by slow addition of saturated sodium bicarbonate. The reaction was extracted with EtOAc and the combined EtOAc extracts were washed with saturated sodium bicarbonate, water and brine. The EtOAc solution was dried over sodium sulfate and filtered. The solution was concentrated in vacuo and the crude product was purified by flash chromatography on silica gel (90:10 hexanes:EtOAc) to yield 76 in 90% yield: LRMS M$^+$=395.

EXAMPLE 45

5-(3,5-Dichloro-phenoxy)-1,4-diethyl-1H-pyrazole-3-carbaldehyde

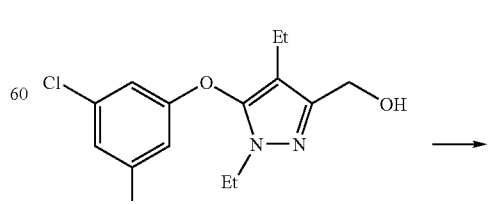

17

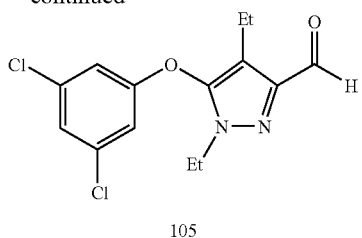

105

Solid tetrapropylammonium perruthenate (118 mg, 0.33 mmol) was added in one portion to a stirred mixture of the alcohol (17; 2.12 g, 6.72 mmol), N-methylmorpholine N-oxide (1.18 g, 10.1 mmol) and 4 Å molecular sieves (3.36 g) in DCM (66 mL) and acetonitrile (8 mL) at room temperature under argon. The reaction was stirred at room temperature for 1.5 h. The reaction mixture was filtered through CELITE® and the filtrate was concentrated in vacuo. The crude product was purified flash chromatography on silica gel (4:1 hexane:EtOAc) to afford 1.79 g (85%) of 105 as a pale yellow oil:LRMS (electrospray) m/z(MH)=313.

EXAMPLE 46

5-(3,5-Dichloro-phenoxy)-1,4-diethyl-3-(1H-imidazol-2-ylmethyl)-1H-pyrazole

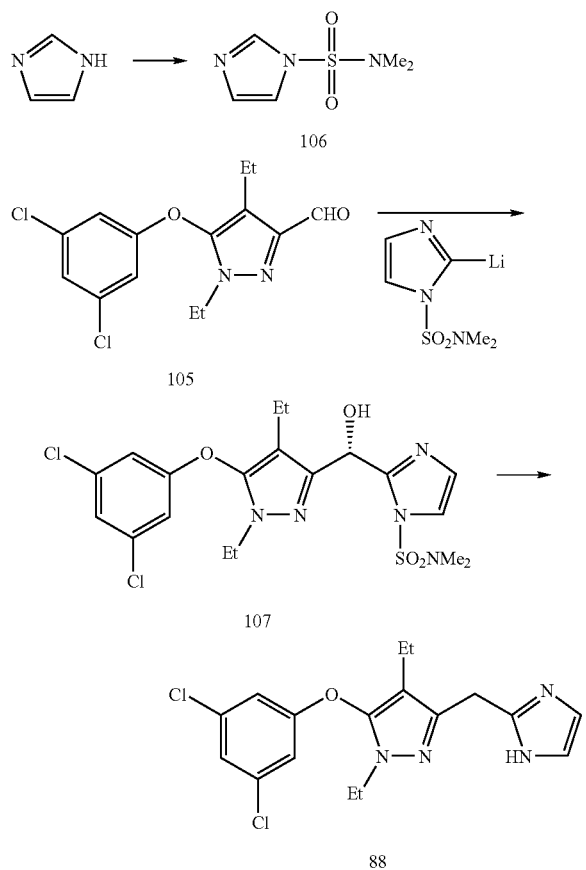

Step 1
Dimethylchlorosulphonamide (3.8 g, 26.5 mmol) was stirred with imidazole (2.0 g, 29.4 mmol) and triethylamine (2.97 g, 29.4 mmol) in benzene (35 mL) at room temperature for 16 h. The mixture was filtered and the solid was washed with benzene (50 mL). The combined filtrate was concentrated in vacuo. The crude product was purified by flash chromatography on silica gel(4:1 hexane:EtOAc) to afford the sulphonamide 106 as colorless oil (3.6 g, 69%).

Step 2
To a solution of the imidazolyl sulphonamide (106; 146 mg, 0.834 mmol) in THF (8 mL) at −78° C. was added dropwise n-butyllithium (1.6 M in hexane, 0.521 mL, 0.834 mmol). The reaction mixture was stirred at −78° C. under argon for 45 min. A solution of the aldehyde 105 (201 mg, 0.642 mmol) in THF (1 mL) was then added slowly. The resulting reaction mixture was allowed to warm up to room temperature and stirred for 19 h. The reaction was quenched with saturated aqueous ammonium chloride (10 mL). The crude carbinol 107 was extracted with EtOAc (3×10 mL). The combined filtrates were dried over magnesium sulfate, filtered and evaporated. The crude product was purified by flash chromatography on silica gel (4:1 hexane:EtOAc) to afford 88 as a pale yellow oil (156 mg, 50%).

Step 3
The carbinol 107 was mixed with trifluoroacetic acid (1.0 mL) and triethylsilane (0.6 mL) at room temperature. The reaction mixture was heated at reflux for 3 h. The reaction mixture was cooled to room temperature and the trifluoroacetic acid and triethylsilane were removed in vacuo. The residue was purified by flash chromatography on silica gel (5% MeOH in DCM) to afford 88 as a white solid (90 mg, 80%); LRMS (electrospray): m/z(MH)=365; mp 145-148° C.

EXAMPLE 47

5-(3,5-Dichloro-phenoxy)-1,4-diethyl-3-(3H-imidazol-4-ylmethyl)-1H-pyrazole

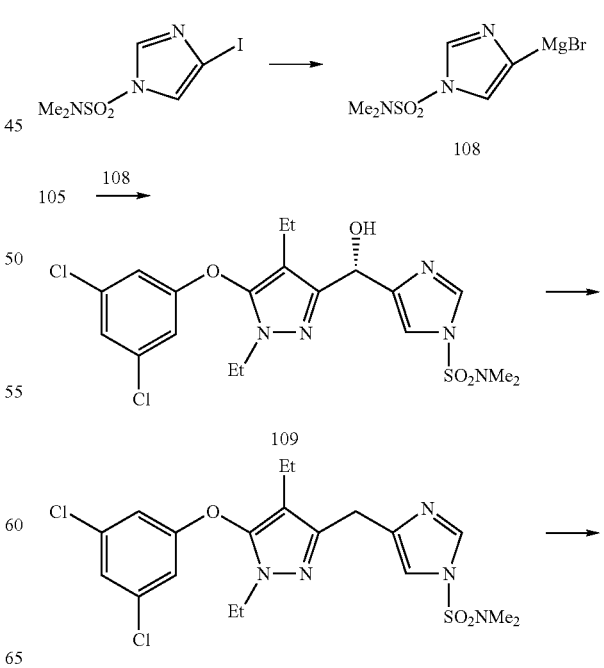

-continued

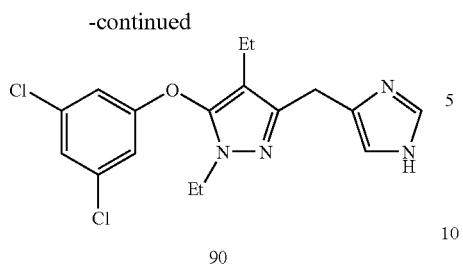

90

-continued

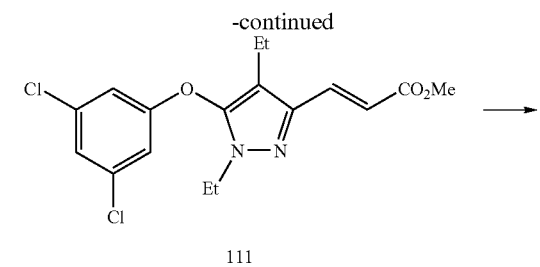

111

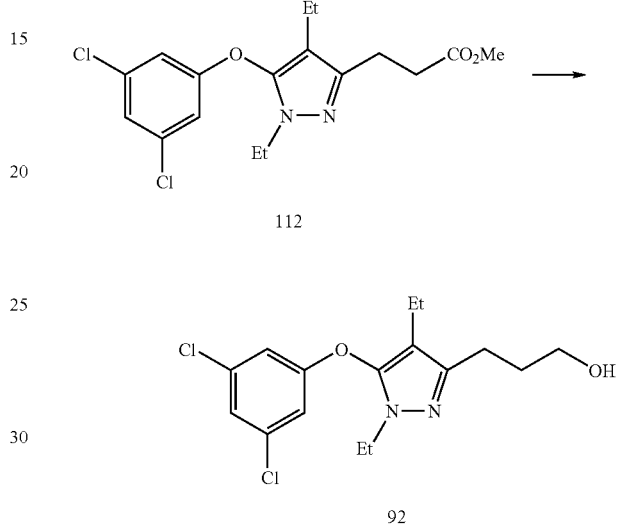

Step 1

To a solution of N,N-dimethyl-4-iodo-1H-imidazole-1-sulfonamide (193 mg, 0.64 mmol) in DCM (3 mL) was added ethyl magnesium bromide (3 M in diethyl ether, 0.18 mL, 0.60 mmol) at room temperature under argon. The reaction mixture was stirred at room temperature for 30 minutes. A solution of the aldehyde (100 mg, 0.32 mmol) in DCM (0.7 mL) was then added to the above formed Grignard reagent dropwise at room temperature. The reaction mixture was stirred at room temperature for 16 h. The reaction was quenched with saturated aqueous ammonium chloride solution (10 mL). The crude carbinol was extracted with EtOAc (3×10 mL). The combined EtOAc extracts were dried over magnesium sulfate, filtered and evaporated. The crude product was purified by flash chromatography on silica gel 5% MeOH in DCM) to afford the carbinol 109 as colorless oil, (120 mg, 76.8%).

Step 2

The carbinol 109 was dissolved in trifluoroacetic acid (1.0 mL) and triethylsilane (0.4 mL) at room temperature. The mixture was refluxed at 80° C. for 3 h. The crude desoxy derivative 110 was isolated after the evaporation of volatile reagents in vacuo.

Step 3

The crude N-protected desoxy derivative 110 was contacted with hydrochloric acid (1 M). The reaction mixture was heated at reflux for 3 h and then stirred at room temperature for 48 h. Saturated sodium bicarbonate solution was added to the reaction mixture until it reached pH 8. The crude product was extracted with EtOAc (3×10 mL). The combined extracts were washed with water (1×10 mL) and brine (1×10 mL) and the solvent removed in vacuo. The crude product was purified by flash chromatography on silica gel (5% MeOH in DCM) to afford 90 as a white solid (60 mg, 67% over two steps): LRMS(electrospray) m/z (MH)=365; mp 142-145.2° C.

EXAMPLE 48

3-[5-(3,5-Dichloro-phenoxy)-1,4-diethyl-1H-pyrazol-3-yl]-propan-1-ol

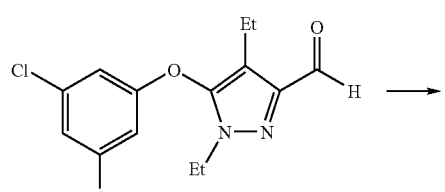

105

To a solution of 105 (102 mg, 0.326 mmol) in THF (10 mL) was added methyl (triphenylphosporanylidene)acetate (1.09 g, 3.26 mmol) at room temperature under argon. The resulting mixture was stirred at room temperature for 24 h and then concentrated in vacuo. The α,β-unsaturated ester 111 was purified flash chromatography on silica gel (5:1 hexane/EtOAc) to afford 111 as a white solid (107 mg, 88.9%).

A solution of the 111 in MeOH (1.0 mL) was added to a stirred mixture of magnesium powder (42 mg, 1.74 mmol) and MeOH (15 mL) at 0° C. The reaction was kept at 0° C. for 3 h and then warmed to room temperature for 16 h. The reaction mixture was poured into 1 M aqueous sodium bisulfate (20 mL). The crude product was extracted with EtOAc (3×10 mL). The EtOAc was removed in vacuo and the crude product was purified by flash chromatography on silica gel (5:1 hexane:EtOAc) to afford 112 as a colorless oil (75 mg, 70%).

To a solution of 112 (75 mg, 0.202 mmol) in THF (10 mL) was added lithium triethylborohydride (1 M in THF, 0.606 mL, 0.606 mmol) at −30° C. over 5 min. The reaction mixture was warmed to 0° C. and stirred for 3 h. The reaction mixture was poured into 2 N hydrochloric acid (50 mL) and the THF was removed in vacuo. The resulting solution was stirred at room temperature for 6 h. The crude product was extracted into DCM (4×10 mL). The combined extracts were dried over magnesium sulfate, filtered and evaporated. The crude product was purified by flash chromatography over silica gel (2:1 hexane:EtOAc) to afford the carbinol 92 as colorless oil (58 mg, 85%): LRMS(electrospray): m/z (MH)=342.

EXAMPLE 49

5-[5-(3,5-Dichloro-phenoxy)-1,4-diethyl-1H-pyrazol-3-ylmethyl]-4-methyl-2,4-dihydro-[1,2,4]triazol-3-one

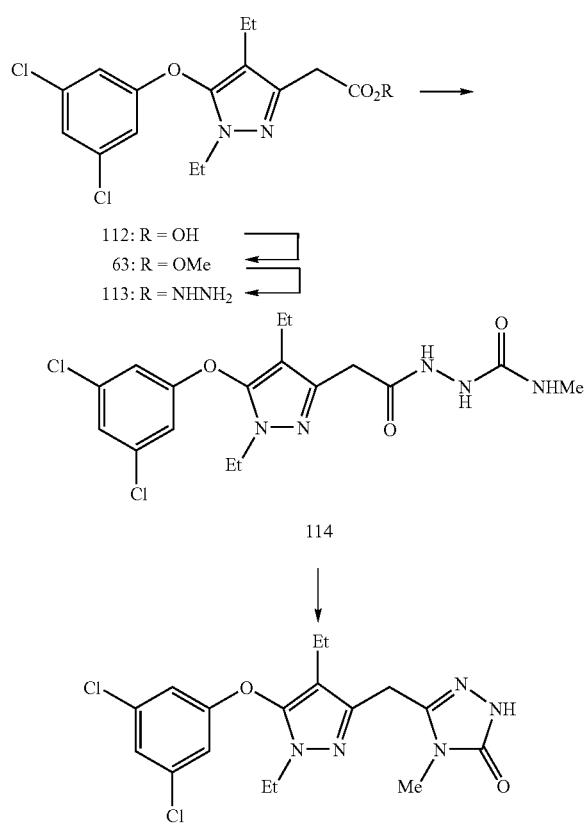

Step 1

To a solution of 112 (100 mg, 0.292 mmol) in MeOH (25 mL) was added three drops of concentrated sulfuric acid. The reaction mixture was refluxed for 3 h and then the bulk of the MeOH was removed in vacuo. Saturated aqueous sodium bicarbonate solution was added to the residue until it reached pH 8. The crude product was extracted with EtOAc (3×10 mL). Removal of the solvent in vacuo gave the crude methyl ester 63 as colorless oil 102 mg (97.8%).

Step 2

To a solution of 63 in absolute EtOH (20 mL) was added hydrazine monohydrate (2 mL). The reaction mixture was heated at reflux for 4 h. The EtOH was removed in vacuo and the resulting residue was dissolved in EtOAc (20 mL). This mixture was washed with water (3×10 mL) and brine (1×10 mL) and dried over magnesium sulfate. The solvent was removed in vacuo the crude hydrazide (113; 95 mg, 93.1%) was used without further purification.

Step 3

To a solution of the 113 (95 mg, 0.27 mmol) in THF (8 mL) was added methyl isocyanate (25 mg, 0.40 mmol) at room temperature. The reaction mixture was stirred at room temperature under argon for 16 h. The reaction was quenched by adding MeOH (10 mL) was and the volatile reagents were removed in vacuo. The crude product 114 was used without further purification.

Step 4

A solution of 114 in MeOH (25 mL) was deoxygenated by bubbling argon through for 20 min. Potassium hydroxide (149 mg, 2.66 mmol) was added to this solution and the resulting mixture was refluxed for 19 h. The reaction mixture was poured into 20 mL of 10% aqueous sodium bisulfate and the crude product was then extracted into EtOAc (3×10 mL). The combined extracts were evaporated and purified by flash chromatography on silica gel (5% MeOH in DCM) to afford 93 as a white solid (89 mg, 77% over 4 steps):LRMS (electrospray) m/z(MH)=396.

EXAMPLE 50

5-(3,5-Dichloro-phenoxy)-1,4-diethyl-3-(2H-pyrazol-3-ylmethyl)-1H-pyrazole

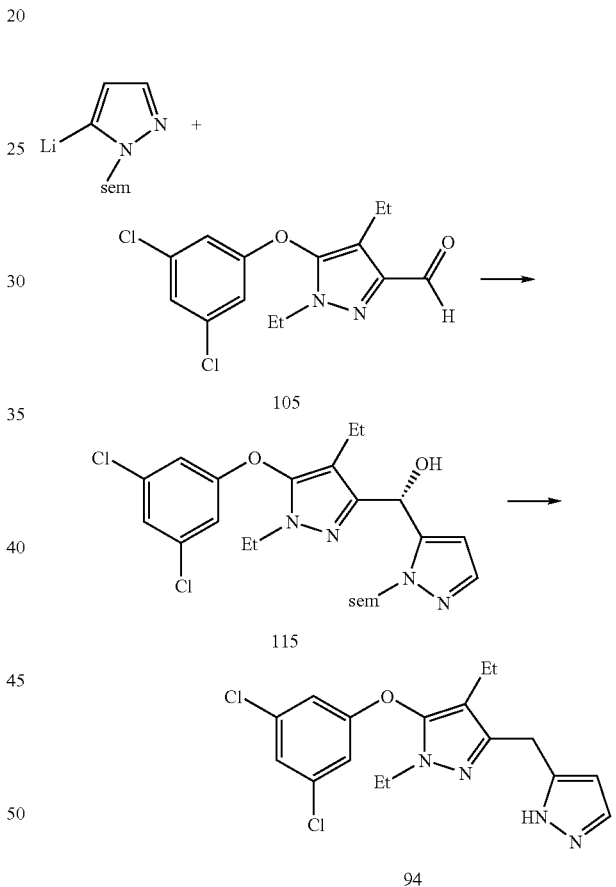

To a solution of the above SEM-protected (SEM=2-(trimethylsilyl)ethoxymethyl) pyrazole (190 mg, 0.958 mmol) in THF (5 mL) at −78° C. was added dropwise a solution of n-butyllithium (1.6 M in hexane, 0.56 mL, 0.896 mmol). The reaction mixture was stirred at −78° C. under argon for 45 min. A solution of 105 in THF (1 mL) was added slowly and the resulting reaction mixture was stirred at −78° C. for 2 h. Saturated ammonium chloride solution (10 mL) was added to quench the reaction and the crude carbinol 115 was extracted with EtOAc (3×10 mL). The combined extracts were evaporated and purified by flash chromatography over silica gel (4:1 hexane:EtOAc) to afford 115 as a pale yellow oil (112 mg, 68%).

The carbinol (115; 112 mg, 0.219 mmol) was mixed with diphosphorus tetraiodide (124 mg, 0.219 mmol) at room temperature. The reaction mixture was stirred at 80° C. for 30 m. The reaction mixture was cooled to room temperature and was stirred vigorously with 10% aqueous sodium bisulfite (20 mL) until the organic layer became colorless. The crude product was extracted with EtOAc (3×10 mL) and the solvent removed in vacuo. The residue was purified by flash chromatography on silica gel (5% MeOH in DCM) to afford 96 as a pale yellow oil (68 mg, 85%).

EXAMPLE 51

3-Chloro-5-[2,4-diethyl-5-(2-hydroxy-ethyl)-2H-pyrazol-3-yloxy]-benzonitrile

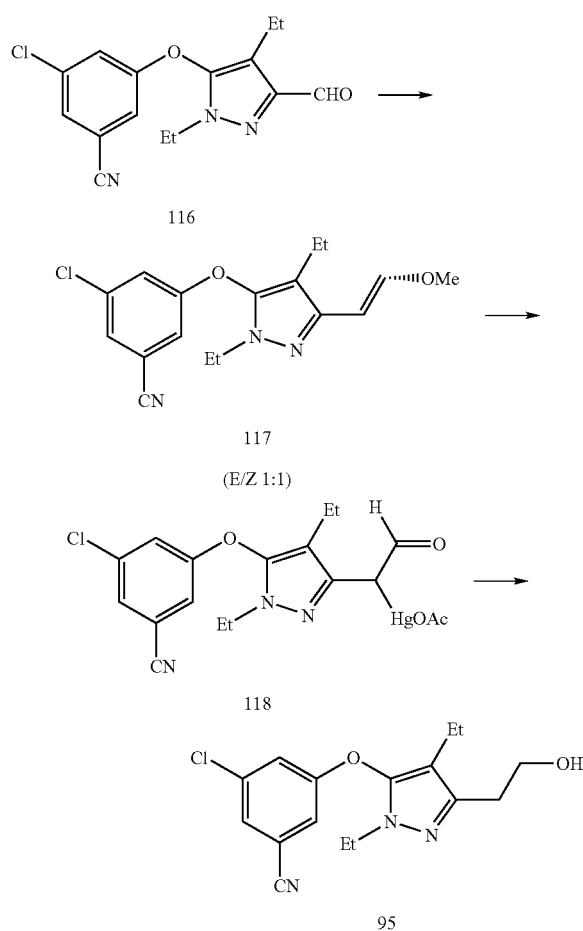

Step 1

To a solution of (methoxymethyl)triphenylphophonium chloride (928 mg, 2.7 mmol) in THF (15 mL) was added potassium bis(trimethylsilyl)amide (0.5 M in toluene, 5.4 mL, 2.7 mmol) at −78° C. over 10 min. The resulting reddish slurry was stirred at −78° C. for 20 min, then a solution of the aldehyde (116; 82 mg, 0.27 mmol) in THF (1.5 mL) was added slowly over 10 min. The reaction mixture was allowed to warm to room temperature and then stirred for 16 h. Acetic acid (5 mL) was added to the reaction mixture and then the mixture was adjusted to pH 7 with 10% aqueous sodium bicarbonate. The crude product was extracted with EtOAc (3×20 mL) and the solvent then removed in vacuo. Purification of the crude product by flash chromatography on silica gel (4:1 hexane:EtOAc) afforded the 1:1 mixture of the enol ethers 117 (74 mg, 83%).

Step 2

To a solution of 117 (74 mg, 0.223 mmol) in acetonitrile (5 mL) and water (5 mL), was added mercury(II) acetate powder (92 mg, 0.29 mmol) in one portion at room temperature. The reaction was complete within 1.5 h. The acetonitrile was removed from the reaction mixture in vacuo to give an aqueous solution of the mercury adduct 118.

Step 3

Ethanol (5 mL) was added to the above aqueous solution of 118 followed by the addition of sodium borohydride (34 mg, 0.90 mmol) at 0° C. The turbid reaction mixture was stirred at 0° C. for 1.5 h. The reaction mixture was then poured into 20 mL of 10% aqueous sodium bisulfate and the resulting mixture then neutralized by adding saturated aqueous sodium bicarbonate. The crude product was extracted with EtOAc (3×10 mL) and crude product purified by flash chromatography on silica gel (4:1 hexane:EtOAc) to afford 97 as a colorless oil (60 mg, 84.3% over two steps):LRMS (electrospray)m/z (MH)=319.

EXAMPLE 52

5-(3,5-Dichloro-phenoxy)-4-ethyl-1-isopropyl-3-methoxymethyl-1H-pyrazole

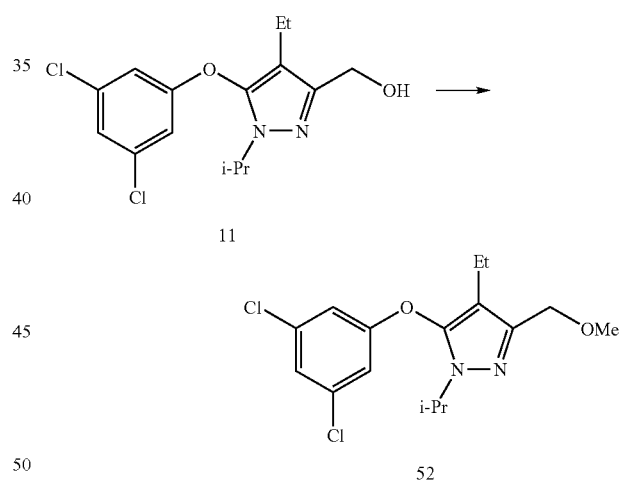

To a solution of 11 (150 mg, 0.456 mmol) in N,N-dimethylformamide (5 mL) was added sodium hydride (60% dispersion in mineral oil, 22 mg, 0.547 mmol) at room temperature. The reaction mixture was stirred until no more bubbles were observed. Methyl iodide (97 mg, 0.684 mmol) was then added to the reaction mixture and this was stirred at room temperature for 20 min. The reaction mixture was poured into 20 mL of 10% aqueous sodium bisulfate. The crude product was extracted with EtOAc (3×10 mL) and the combined organic layers were washed with water (2×10 mL) and then brine (1×10 mL). The solvent was removed in vacuo and crude product purified by flash chromatography on silica gel (5:1 hexane:EtOAc) to afford pure 52 product as colorless oil (110 mg, 70%):LRMS (electrospray) m/z (MH)=343.

EXAMPLE 53

HIV Reverse Transcriptase Assay: Inhibitor IC$_{50}$ Determination

HIV-1 RT assay was carried out in 96-well Millipore MultiScreen MADVNOB50 plates using purified recombinant enzyme and a poly(rA)/oligo(dT)$_{16}$ template-primer in a total volume of 50 μL. The assay constituents were 50 mM Tris/HCl, 50 mM NaCl, 1 mM EDTA, 6 mM MgCl$_2$, 5 μM dTTP, 0.15 μCi [$^3$H] dTTP, 5 μg/ml poly (rA) pre annealed to 2.5 μg/ml oligo (dT)$_{16}$ and a range of inhibitor concentrations in a final concentration of 10% DMSO. Reactions were initiated by adding 4 nM HIV-1 RT and after incubation at 37° C. for 30 min, they were stopped by the addition of 50 μl ice cold 20% TCA and allowed to precipitate at 4° C. for 30 min. The precipitates were collected by applying vacuum to the plate and sequentially washing with 3×200 μl of 10% TCA and 2×200 μl 70% EtOH. Finally, the plates were dried and radioactivity counted in a Packard Top-Counter after the addition of 25 μl scintillation fluid per well. IC$_{50}$'s were calculated by plotting % inhibition versus log$_{10}$ inhibitor concentrations. Representative IC$_{50}$ data has been included in Table 2.

Antiviral Assay Method:

Anti-HIV antiviral activity was assessed using an adaptation of the method of Pauwels et al. {Pauwels et al., 1988, J Virol Methods 20:309-321 }. The method is based on the ability of compounds to protect HIV-infected T lymphoblastoid cells (MT4 cells) from cell-death mediated by the infection. The endpoint of the assay was calculated as the concentration of compound at which the cell viability of the culture was preserved by 50% ('50% inhibitory concentration', IC$_{50}$). The cell viability of a culture was determined by the uptake of soluble, yellow 3-[4,5-dimethylthiazol-2-yl]-2,5-diphenyltetrazolium bromide (MTT) and its reduction to a purple insoluble formazan salt. After solubilization, spectrophotometric methods were employed to measure the amount of formazan product.

MT4 cells were prepared to be in logarithmic-phase growth and a total of 2×10$^6$ cells infected with the HXB2-strain of HIV at a multiplicity of 0.0001 infectious units of virus per cell in a total volume of between 200-500 microliters. The cells were incubated with virus for one hour at 37° C. before removal of virus. The cells are then washed in 0.01 M phosphate buffered saline, pH 7.2 before being resuspended in culture medium for incubation in culture with serial dilutions of test compound. The culture medium used was RPMI 1640 without phenol red, supplemented with penicillin, streptomycin, L-glutamine and 10% fetal calf serum (GM10).

Test compounds were prepared as 2 mM solutions in dimethylsulfoxide (DMSO). Four replicate, serial 2-fold dilutions in GM10were then prepared and 50 microliters amounts placed in 96-well plates over a final nanomolar concentration range of 625-1.22. Fifty microliters GM10 and 3.5×10$^4$ infected cells were then added to each well. Control cultures containing no cells (blank), uninfected cells (100% viability; 4 replicates) and infected cells without compound (total virus-mediated cell death; 4 replicates) were also prepared. The cultures were then incubated at 37° C. in a humidified atmosphere of 5% CO$_2$ in air for 5 days.

A fresh solution of 5 mg/mL MTT was prepared in 0.01 M phosphate buffered saline, pH 7.2 and 20 microliters added to each culture. The cultures were further incubated as before for 2 hours. They were then mixed by pipetting up and down and 170 microliters of Triton X-100 in acidified isopropanol (10% v/v Triton X-100 in 1:250 mixture of concentrated HCl in isopropanol). When the formazan deposit was fully solubilized by further mixing, the absorbance (OD) of the cultures was measured at 540 nm and 690 nm wavelength (690 nm readings were used as blanks for artifacts between wells). The percent protection for each treated culture was then calculated from the equation:

$$\% \text{ Protection} = \frac{(OD \text{ drug-treated cultures}) - (OD \text{ untreated virus control cultures})}{(OD \text{ uninfected cultures}) - (OD \text{ untreated virus control cultures})} \times 100\%$$

The IC$_{50}$ can be obtained from graph plots of percent protection versus log$_{10}$ drug concentration.

In both assays, compounds of formulas I range in activity from an IC$_{50}$ of about 0.5 to about 10000 nM or 0.5 to about 5000 nM, with preferred compounds having a range of activity from about 0.5 to about 750 nM, more preferably about 0.5 to 300 nM, and most preferably about 0.5 to 50 nM.

TABLE 2

| Cpd No. | IC$_{50}$(μM) RTI | IC$_{50}$(μM) Antiviral |
|---|---|---|
| 36 | 0.0383 | — |
| 40 | 0.6483 | — |
| 22 | 1.56 | — |
| 17 | 1.66 | 0.0401 |
| 48 | 1.07 | — |

EXAMPLE 54

Pharmaceutical Compositions

Composition for Oral Administration

| Ingredient | % wt./wt. |
|---|---|
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

Composition for Oral Administration

| Ingredient | % wt./wt. |
|---|---|
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as MeOH. The formulation is then dried and formed into tablets (containing about 20 mg of active compound) with an appropriate tablet machine.

| Composition for Oral Administration | |
|---|---|
| Ingredient | Amount |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

| Parenteral Formulation (IV) | |
|---|---|
| Ingredient | % wt./wt. |
| Active ingredient | 0.25 g |
| Sodium Chloride | q.s. to make isotonic |
| Water for injection to | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

| Suppository Formulation | |
|---|---|
| Ingredient | % wt./wt. |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

| Topical Formulation | |
|---|---|
| Ingredients | grams |
| Active compound | 0.2–2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025-0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50-100 microliters of formulation per actuation. A typical dosing schedule is 2-4 sprays every 4-12 hours.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

What is claimed is:

1. A compound according to formula I

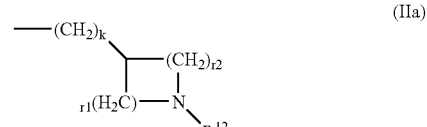

(IIa)

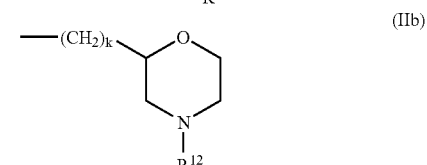

(IIb)

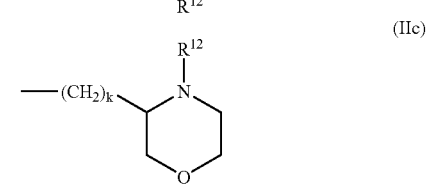

(IIc)

wherein $R^1$ is selected from the group consisting of $C_{1-6}$alkyl, $C_{1-6}$haloalkyl, $C_{3-6}$alkenyl, $C_{3-6}$alkynyl, $C_{3-7}$cycloalkyl, $C_{1-3}$alkoxy-$C_{1-3}$alkyl, phenyl and benzyl, wherein, said phenyl and said benzyl optionally substituted with one to three substituents independently selected from the group consisting of $C_{1-6}$alkyl, $C_{1-6}$-haloalkyl, $C_{1-6}$alkoxy, $C_{1-6}$haloalkoxy, $C_{1-6}$alkylthio, nitro, halogen and cyano;

$R^2$ is phenyl optionally substituted with one to three groups independently selected from the group consisting of halogen, cyano, $C_{1-6}$alkyl, $C_{1-6}$alkoxy, $C_{1-6}$alkoxycarbonyl, and $CONR^6R^7$;

$R^3$ is substituted $C_{1-6}$alkyl, substituted $C_{1-3}$alkoxy-$C_{1-3}$alkyl, substituted $C_{3-6}$alkenyl, $C_{3-7}$ cycloalkyl, optionally substituted $C_{1-6}$alkoxy, $(CH_2)_nR^5$, $CH(OH)R^5$, —$(CH_2)_o$—O—$(CH_2)_pR^5$, $NR^6R^7$, $C(=Y)Z$ or —$X(C=Y)Z$;

wherein,
said alkyl, said $C_{1-3}$ alkoxy-$C_{1-3}$ alkyl and said alkenyl are substituted by —OH, —$NR^6R^7$, —$C(=Y)Z$, —$X(C-Y)Z$, CN, —$S(O)_q$—$C_{1-6}$ alkyl; —$SO_2NR^6R^7$, —$SO_2NHNH_2$, or —$NR^6SO_2$—$C_{1-6}$ alkyl;

said alkoxy is optionally substituted by —OH, —$NR^6R^7$, —$C(=Y)Z$, —$X(C=Y)Z$, —$S(O)_q$—$C_{1-6}$alkyl; —$SO_2NR^6R^7$ or —$SO_2NHNH_2$;

$R^3$ is a phenyl optionally substituted with halo,—$OR^6$, —$NR^6R^7$, —$C(=O)Z$, —$X(C=O)Z$;

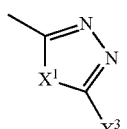

(IIIa)

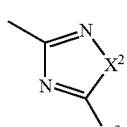

(IIIb)

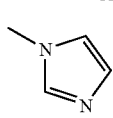

(IIIc)

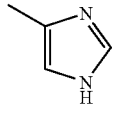

(IIId)

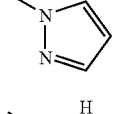

(IIIe)

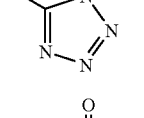

(IIIf)

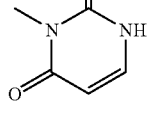

(IIIg)

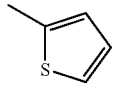

(IIIh)

wherein $R^4$ is $C_{1-6}$alkyl, $C_{2-6}$alkenyl, $C_{2-6}$alkynyl; wherein, said alkyl, said alkenyl and said alkynyl are optionally substituted by —OH, —$OR^6$, —$NR^8R^9$, —$C(=Y)Z$, —$X(C=Y)Z$, —$S(O)_q$—$C_{1-6}$alkyl, —$SO_2$ or —$SO_2NHNH_2$;

n, o, p and q are as defined below;

$R^6$, $R^7$, $R^8$ and $R^9$ taken independently are selected from the group consisting of hydrogen, $C_{1-6}$alkyl, $C_{1-6}$hydroxyalkyl, $C_{1-3}$alkoxy-$C_{1-3}$alkyl $C_{1-3}$alkylamino-$C_{1-3}$alkyl and $C_{1-3}$ dialkylamino-$C_{1-3}$alkyl X, and Y are independently O or $NR^6$;

Z is hydrogen, hydroxyl, $C_{1-6}$alkoxy, $NR^6R^{13}$, $C_{1-6}$alkyl, $C_{1-3}$alkoxy-$C_{1-3}$alkyl wherein $R^{13}$ is $R^7$ or phenyl optionally substituted with one to three groups independently selected from the group consisting of halogen, cyano, $C_{1-3}$alkyl, $C_{1-3}$haloalkyl and $C_{1-3}$alkoxy;

n is 0 to 3;

o and p are independently 0 to 4 and o+p≦5;

q is 0 to 2; and, acid addition salts, hydrates and solvates thereof.

2. A compound according to claim 1 wherein:
$R^1$ is selected from the group consisting of $C_{1-6}$alkyl, $C_{1-6}$haloalkyl, $C_{3-7}$cycloalkyl, $C_{1-3}$alkoxy-$C_{1-3}$alkyl and optionally-substituted phenyl; and
$R^4$ is $C_{1-6}$ alkyl said alkyl optionally substituted by —OH, —$OR^6$, —$NR^8R^9$, —$C(=Y)Z$ or —$X(C—Y)Z$.

3. A compound according to claim 2 wherein $R^3$ is substituted $C_{1-6}$ alkyl.

4. A compound according to claim 2 wherein $R^3$ is —$(CH_2)_nNR^6R^7$, —$(CH_2)_nC(=O)Z$ or —$(CH_2)_nXC(=O)Z$.

5. A pharmaceutical composition comprising a therapeutically effective quantity of a compound of formula I

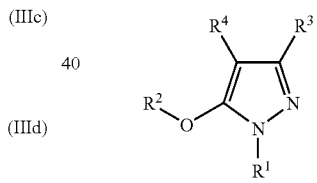

I wherein
$R^1$ is selected from the group consisting of $C_{1-6}$ alkyl, $C_{1-6}$haloalkyl, $C_{3-6}$alkenyl, $C_{3-6}$ alkynyl, $C_{3-7}$cycloalkyl, $C_{1-3}$alkoxy-$C_{1-3}$alkyl, phenyl and benzyl, wherein, said phenyl and said benzyl optionally substituted with one to three substituents independently selected from the group consisting of $C_{1-6}$alkyl, $C_{1-6}$haloalkyl, $C_{1-6}$ alkoxy, $C_{1-6}$haloalkoxy, $C_{1-6}$alkylthio, nitro, halogen and cyano;

$R^2$ is phenyl optionally substituted with one to three groups independently selected from the group consisting of halogen, cyano, $C_{1-6}$alkyl, $C_{1-6}$alkoxy, $C_{1-6}$ alkoxycarbonyl, and $CONR^6R^7$;

$R^3$ is substituted $C_{1-6}$ alkyl, substituted $C_{1-3}$alkoxy-$C_{1-3}$ alkyl, substituted $C_{3-6}$alkenyl, $C_{3-7}$cycloalkyl, optionally substituted $C_{1-6}$alkoxy, —$(CH_2)_nR^5$, —$CH(OH)R^5$, —$(CH_2)_o$—O—$(CH_2)_pR^5$, —$NR^6R^7$, —$C(=Y)Z$, or—$X(C=Y)Z$;

wherein,
said alkyl, said $C_{1-3}$alkoxy-$C_{1-3}$alkyl and said alkenyl are substituted by —OH, —$NR^6R^7$, —$C(=Y)Z$, —X(C=Y)Z, CN, —S(O)$_q$—C$_{1-6}$alkyl, —SO$_2$NR$^6$R$^7$, —SO$_2$NHNH$_2$, or —NR$^6$SO$_2$—C$_{1-6}$alkyl;

said alkoxy is optionally substituted by —OH, —NR$^6$R$^7$, —C(=Y)Z, —X(C=Y)Z, —S(O)$_q$—C$_{1-6}$ alkyl; —SO$_2$NR$^6$R$^7$ or —SO$_2$NHNH$_2$;

R$^5$ is a phenyl optionally substituted with halo, —OR$^6$, —NR$^6$, R$^7$, —C(=O)Z, —X(C=O)Z;

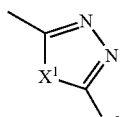

(IIIa)

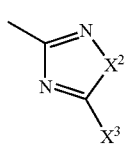

(IIIb)

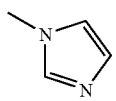

(IIIc)

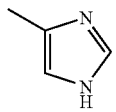

(IIId)

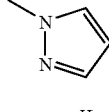

(IIIe)

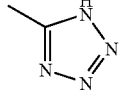

(IIIf)

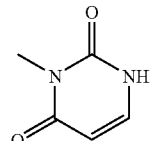

(IIIg)

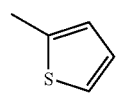

(IIIh)

R$^4$ is C$_{1-6}$alkyl, C$_{2-6}$alkenyl, C$_{2-6}$alkynyl; wherein, said alkyl, said alkenyl and said alkynyl are optionally substituted by —OH, —OR$^6$, —NR$^8$R$^9$, —C(=Y)Z, —X(C=Y)Z, —S(O)$_q$—C$_{1-6}$alkyl, —SO$_2$NR$^6$R$^7$ or —SO$_2$NHNH$_2$;

n, o, p and q are as defined below;

R$^6$, R$^7$, R$^8$ and R$^9$ taken independently are hydrogen, C$_{1-6}$alkyl, C$_{1-6}$hydroxyalkyl, C$_{1-3}$ alkoxy-C$_{1-3}$alkyl C$_{1-3}$alkylamino-C$_{1-3}$alkyl or C$_{1-3}$dialkylamino-C$_{1-3}$alkyl X, and Y are independently O or NR$^6$;

Z is hydrogen, hydroxyl, C$_{1-6}$alkoxy, NR$^6$R$^{13}$, C$_{1-6}$alkyl, C$_{1-3}$alkoxy-C$_{1-3}$alkyl wherein R$^{13}$ is R$^7$ or phenyl optionally substituted with one to three groups independently selected from the group consisting of halogen, cyano, C$_3$alkyl, C$_{1-3}$haloalkyl and C$_{1-3}$alkoxy;

n is 0 to 3;

o and p are independently 0 to 4 and o+p≧5;

q is 0 to 2;

acid addition salts, hydrates and acid addition salts, hydrates and solvates thereof, in admixture with at least one pharmaceutically acceptable carrier or diluent sufficient upon administration in a single or multiple dose regimen for treating diseases mediated by human immunodeficiency virus or for inhibiting HIV.

* * * * *